US012582791B2

(12) United States Patent
Bearne et al.

(10) Patent No.: US 12,582,791 B2
(45) Date of Patent: Mar. 24, 2026

(54) PATIENT INTERFACE

(71) Applicant: Fisher & Paykel Healthcare Limited, Auckland (NZ)

(72) Inventors: Peter David Alexander Bearne, Auckland (NZ); Blair Raymund Dadson Murphy, Auckland (NZ); Kirstin Elizabeth Middelkoop, Auckland (NZ); Fadi Karim Moh'd Mashal, Auckland (NZ); Michael John Henri Cox, Auckland (NZ); Sophie Kathryn Randles, Auckland (NZ); Mark Arvind McLaren, Auckland (NZ); Ronan Leahy, Auckland (NZ); Roheet Patel, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 791 days.

(21) Appl. No.: 17/662,150

(22) Filed: May 5, 2022

(65) Prior Publication Data

US 2023/0086237 A1 Mar. 23, 2023

Related U.S. Application Data

(63) Continuation of application No. 15/526,686, filed as application No. PCT/IB2015/058766 on Nov. 13, 2015, now Pat. No. 11,351,323.
(Continued)

(51) Int. Cl.
*A61M 16/06* (2006.01)
*A61M 16/08* (2006.01)

(52) U.S. Cl.
CPC .... *A61M 16/0683* (2013.01); *A61M 16/0616* (2014.02); *A61M 16/0622* (2014.02); *A61M 16/0825* (2014.02); *A61M 2207/00* (2013.01)

(58) Field of Classification Search
CPC .......... A61M 16/0683; A61M 16/0622; A61M 16/0605; A61M 16/0633; A61M 16/0825;
(Continued)

(56) References Cited

U.S. PATENT DOCUMENTS 443,191 A 12/1890 Illing
804,272 A 11/1905 Schwarz
(Continued)

FOREIGN PATENT DOCUMENTS

DE 3719009 12/1988
DE 102006057763 A1 2/2008
(Continued)

*Primary Examiner* — Joseph D. Boecker
*Assistant Examiner* — Brian T Khong
(74) *Attorney, Agent, or Firm* — VIA LLP

(57) ABSTRACT

A patient interface can have features improving the comfort of use by reducing the perceived pressure of a nose-contacting cushion of the patient interface against the nose. The patient interface can have rigid headgear connection elements connectable to a frame of the respiratory interface. The rigid headgear connection elements can be shaped to reduce the force of the cushion against the nose. Headgear for a patient interface can also have features improving the stability of headgear of the head. The headgear can have a relatively rigid framework and a relatively pliable overlay covering the framework. The framework can have apertures defining a front portion to be positioned below or near the cheekbones, a rear portion to be positioned over the sides of the head around the ears, and a top portion to extend upward along the head towards the crown.

31 Claims, 67 Drawing Sheets

Related U.S. Application Data

(60) Provisional application No. 62/214,802, filed on Sep. 4, 2015, provisional application No. 62/079,915, filed on Nov. 14, 2014.

(58) Field of Classification Search
CPC .............. A61M 16/0816; A61M 16/06; A61M 16/0616
See application file for complete search history.

(56) References Cited

U.S. PATENT DOCUMENTS

| | | | |
|---|---|---|---|
| 1,229,050 A | 6/1917 | Donald |
| 1,445,010 A | 2/1923 | Feinberg |
| 2,228,218 A | 1/1941 | Schwartz |
| 2,317,608 A | 4/1943 | Heidbrink |
| 2,353,643 A | 7/1944 | Bulbulian |
| 2,403,046 A | 7/1946 | Bulbulian |
| 2,414,405 A | 1/1947 | Bierman et al. |
| 2,444,417 A | 7/1948 | Beirman |
| 2,540,567 A | 2/1951 | Bennet |
| 2,742,039 A | 4/1956 | Bloom |
| 2,867,812 A | 1/1959 | Roth et al. |
| 2,875,757 A | 3/1959 | Galleher |
| 2,931,356 A | 4/1960 | Hermann |
| 3,027,617 A | 4/1962 | Norman |
| 3,040,741 A | 6/1962 | Raymond |
| 3,092,105 A | 6/1963 | Gabb |
| 3,117,574 A | 1/1964 | Replogle |
| 3,170,463 A | 2/1965 | Duggan |
| 3,234,939 A | 2/1966 | Morton |
| 3,234,940 A | 2/1966 | Morton |
| 3,292,618 A | 12/1966 | Davis et al. |
| 3,295,529 A | 1/1967 | Corrigall et al. |
| 3,315,674 A | 4/1967 | Bloom et al. |
| 3,330,273 A | 7/1967 | Bennett |
| 3,330,274 A | 7/1967 | Bennett |
| 3,530,031 A | 9/1970 | Loew |
| 3,599,635 A | 8/1971 | Ansite |
| 3,752,157 A | 8/1973 | Malmin |
| 4,384,577 A | 5/1983 | Huber et al. |
| 4,470,413 A | 9/1984 | Warncke |
| 4,603,692 A | 8/1986 | Montesi |
| 4,674,136 A | 6/1987 | Kestrabel-Hart |
| 4,675,919 A | 6/1987 | Heine et al. |
| 4,764,989 A | 8/1988 | Bourgeois |
| 4,947,488 A | 8/1990 | Ashinoff |
| 4,960,121 A | 10/1990 | Nelson et al. |
| 5,005,571 A | 4/1991 | Dietz |
| 5,323,516 A | 6/1994 | Hartmann |
| 5,441,046 A | 8/1995 | Starr et al. |
| 5,513,634 A | 5/1996 | Jackson |
| 5,517,986 A | 5/1996 | Starr et al. |
| 5,540,223 A | 7/1996 | Starr et al. |
| 5,560,354 A | 10/1996 | Berthon-Jones et al. |
| 5,570,684 A | 11/1996 | Behr |
| 5,570,689 A | 11/1996 | Starr et al. |
| 5,724,965 A | 3/1998 | Handke et al. |
| 5,832,918 A | 11/1998 | Pantino |
| 5,896,857 A | 4/1999 | Hely et al. |
| 5,934,276 A | 8/1999 | Fabro et al. |
| 6,016,804 A | 1/2000 | Gleason et al. |
| 6,119,694 A | 9/2000 | Correa et al. |
| 6,123,071 A | 9/2000 | Berthon-Jones et al. |
| 6,292,985 B1 | 9/2001 | Grunberger |
| 6,338,342 B1 | 1/2002 | Fecteau et al. |
| 6,341,382 B1 | 1/2002 | Ryvin et al. |
| 6,371,110 B1 | 4/2002 | Peterson et al. |
| 6,374,826 B1 | 4/2002 | Gunaratnam et al. |
| 6,422,238 B1 | 7/2002 | Lithgow |
| 6,467,483 B1 | 10/2002 | Kopacko et al. |
| 6,470,886 B1 | 10/2002 | Jestrabek-Hart |
| 6,491,034 B1 | 12/2002 | Gunaratnam et al. |
| 6,536,435 B1 | 3/2003 | Fecteau et al. |
| 6,584,975 B1 | 7/2003 | Taylor |
| 6,598,271 B2 | 7/2003 | Nire |
| 6,606,767 B2 | 8/2003 | Wong |
| 6,647,597 B2 | 11/2003 | Reiter |
| 6,651,663 B2 | 11/2003 | Barnett et al. |
| 6,823,869 B2 | 11/2004 | Raje et al. |
| 6,851,428 B2 | 2/2005 | Dennis |
| 6,907,882 B2 | 6/2005 | Ging et al. |
| 6,990,691 B2 | 1/2006 | Klotz et al. |
| 7,063,088 B1 | 6/2006 | Christopher |
| 7,152,602 B2 | 12/2006 | Bateman et al. |
| 7,210,481 B1 | 5/2007 | Lovell et al. |
| 7,296,575 B1 | 11/2007 | Radney |
| 7,318,437 B2 | 1/2008 | Gunaratnam et al. |
| 7,353,826 B2 | 4/2008 | Sleeper et al. |
| 7,509,958 B2 | 3/2009 | Amarasinghe et al. |
| 7,762,254 B2 | 7/2010 | Ho |
| 7,793,987 B1 | 9/2010 | Busch et al. |
| 7,810,497 B2 | 10/2010 | Pittman et al. |
| 7,942,148 B2 | 5/2011 | Davidson et al. |
| 7,958,893 B2 | 6/2011 | Lithgow |
| 7,975,694 B2 | 7/2011 | Ho |
| 7,992,560 B2 | 8/2011 | Burton et al. |
| 8,028,699 B2 | 10/2011 | Ho et al. |
| 8,042,538 B2 | 10/2011 | Ging et al. |
| 8,042,539 B2 | 10/2011 | Chandran et al. |
| 8,042,542 B2 | 10/2011 | Ging et al. |
| 8,132,270 B2 | 3/2012 | Lang et al. |
| 8,136,523 B2 | 3/2012 | Rudolph |
| 8,136,524 B2 | 3/2012 | Ging et al. |
| 8,146,596 B2 | 4/2012 | Smith et al. |
| 8,196,583 B2 | 6/2012 | Radney |
| 8,251,066 B1 | 8/2012 | Ho et al. |
| 8,286,636 B2 | 10/2012 | Gunaratnam et al. |
| 8,297,285 B2 | 10/2012 | Henry et al. |
| 8,342,181 B2 | 1/2013 | Selvarajan et al. |
| 8,439,035 B2 | 5/2013 | Dantanarayana et al. |
| 8,490,623 B2 | 7/2013 | Berthon-Jones et al. |
| 8,490,624 B2 | 7/2013 | Ho et al. |
| 8,550,084 B2 | 10/2013 | Ng et al. |
| 8,596,271 B2 | 12/2013 | Matula, Jr. et al. |
| 8,622,057 B2 | 1/2014 | Ujhazy et al. |
| 8,636,005 B2 | 1/2014 | Gradon |
| 8,636,007 B2 | 1/2014 | Rummery et al. |
| 8,646,449 B2 | 2/2014 | Bowsher |
| 8,733,358 B2 | 5/2014 | Lithgow et al. |
| 8,757,157 B2 | 6/2014 | Price et al. |
| 8,770,190 B2 | 7/2014 | Doherty et al. |
| 8,800,563 B2 | 8/2014 | Doherty et al. |
| 8,856,975 B2 | 10/2014 | Lang et al. |
| 8,931,484 B2 | 1/2015 | Melidis et al. |
| 8,950,404 B2 | 2/2015 | Formica et al. |
| 8,985,117 B2 | 3/2015 | Gunaratnam et al. |
| 9,010,330 B2 | 4/2015 | Barlow et al. |
| 9,032,955 B2 | 5/2015 | Lubke et al. |
| 9,044,564 B2 | 6/2015 | Dravitzki et al. |
| 9,067,033 B2 | 6/2015 | Davidson et al. |
| 9,149,593 B2 | 10/2015 | Dravitzki et al. |
| 9,155,857 B2 | 10/2015 | Lalonde |
| 9,211,388 B2 | 12/2015 | Swift et al. |
| 9,220,860 B2 | 12/2015 | Davidson et al. |
| 9,265,909 B2 | 2/2016 | Ho et al. |
| 9,387,302 B2 | 7/2016 | Dravitzki et al. |
| 9,480,809 B2 | 11/2016 | Guney et al. |
| 9,539,403 B2 | 1/2017 | Eves et al. |
| 9,901,701 B2 | 2/2018 | Gunaratnam et al. |
| 10,130,785 B2 | 11/2018 | Dravitzki et al. |
| 10,201,678 B2 | 2/2019 | Guney et al. |
| 11,351,323 B2 | 6/2022 | Beane et al. |
| 2002/0096178 A1 | 7/2002 | Ziaee |
| 2003/0196655 A1 | 10/2003 | Ging et al. |
| 2004/0083534 A1 | 5/2004 | Ruiz |
| 2004/0107547 A1 | 6/2004 | Chung |
| 2004/0112377 A1 | 6/2004 | Amarasinghe et al. |
| 2004/0182398 A1 | 9/2004 | Sprinkle |
| 2004/0221850 A1 | 11/2004 | Ging |
| 2005/0028822 A1 | 2/2005 | Sleeper et al. |
| 2005/0056286 A1 | 3/2005 | Huddart et al. |
| 2005/0098183 A1 | 5/2005 | Nash et al. |
| 2006/0042629 A1 | 3/2006 | Geist |

(56) References Cited

U.S. PATENT DOCUMENTS

| | | |
|---|---|---|
| 2006/0174892 A1 | 8/2006 | Leksutin et al. |
| 2006/0283461 A1* | 12/2006 | Lubke .............. A61M 16/0605 |
| | | 128/201.19 |
| 2007/0246043 A1 | 10/2007 | Kwok et al. |
| 2008/0083412 A1 | 4/2008 | Henry et al. |
| 2008/0190432 A1 | 8/2008 | Blochlinger et al. |
| 2009/0032026 A1 | 2/2009 | Price |
| 2009/0044808 A1 | 2/2009 | Guney et al. |
| 2009/0114229 A1 | 5/2009 | Frater et al. |
| 2009/0173349 A1 | 7/2009 | Hernandez et al. |
| 2010/0000543 A1 | 1/2010 | Berthon-Jones et al. |
| 2010/0000544 A1 | 1/2010 | Blaszezykiewiez et al. |
| 2010/0083961 A1 | 4/2010 | McAuley et al. |
| 2010/0132717 A1 | 6/2010 | Davidson et al. |
| 2010/0307502 A1 | 12/2010 | Rummery et al. |
| 2010/0313891 A1 | 12/2010 | Veliss et al. |
| 2010/0319700 A1* | 12/2010 | Ng .................... A61M 16/0066 |
| | | 128/206.28 |
| 2011/0000492 A1 | 1/2011 | Veliss et al. |
| 2011/0072553 A1 | 3/2011 | Ho |
| 2011/0146685 A1 | 6/2011 | Allan et al. |
| 2011/0197341 A1 | 8/2011 | Formica et al. |
| 2011/0253143 A1 | 10/2011 | Ho et al. |
| 2011/0265796 A1 | 11/2011 | Amarasinghe et al. |
| 2011/0315143 A1 | 12/2011 | Frater |
| 2012/0138061 A1* | 6/2012 | Dravitzki .......... A61M 16/0683 |
| | | 128/205.25 |
| 2012/0138063 A1 | 6/2012 | Eves et al. |
| 2012/0152255 A1 | 6/2012 | Barlow et al. |
| 2012/0167892 A1 | 7/2012 | Matula, Jr. |
| 2012/0216819 A1 | 8/2012 | Raje et al. |
| 2012/0304999 A1 | 12/2012 | Swift et al. |
| 2012/0325219 A1 | 12/2012 | Smith |
| 2013/0000648 A1 | 1/2013 | Madaus et al. |
| 2013/0008446 A1 | 1/2013 | Carroll et al. |
| 2013/0008449 A1* | 1/2013 | Busch .............. A61M 16/0683 |
| | | 128/206.21 |
| 2013/0139822 A1 | 6/2013 | Gibson et al. |
| 2013/0152937 A1 | 6/2013 | Jablonski |
| 2013/0199537 A1 | 8/2013 | Formica et al. |
| 2013/0213400 A1 | 8/2013 | Barlow et al. |
| 2013/0220327 A1 | 8/2013 | Barlow et al. |
| 2013/0263858 A1 | 10/2013 | Ho et al. |
| 2013/0306077 A1 | 11/2013 | Greenberg |
| 2013/0327336 A1 | 12/2013 | Burnham et al. |
| 2014/0026888 A1 | 1/2014 | Matula, Jr. et al. |
| 2014/0034057 A1 | 2/2014 | Todd et al. |
| 2014/0053844 A1 | 2/2014 | Rummery et al. |
| 2014/0069433 A1 | 3/2014 | Walker et al. |
| 2014/0094669 A1 | 4/2014 | Jaffe et al. |
| 2014/0096774 A1 | 4/2014 | Olsen et al. |
| 2014/0166018 A1 | 6/2014 | Dravitsky et al. |
| 2014/0166019 A1 | 6/2014 | Ho et al. |
| 2014/0174444 A1 | 6/2014 | Darkin et al. |
| 2014/0174447 A1 | 6/2014 | Ho et al. |
| 2014/0190486 A1 | 7/2014 | Dunn et al. |
| 2014/0209098 A1 | 7/2014 | Dunn et al. |
| 2014/0261412 A1 | 9/2014 | Guney et al. |
| 2014/0261434 A1 | 9/2014 | Ng et al. |
| 2014/0261440 A1 | 9/2014 | Chodkowski |
| 2014/0283822 A1 | 9/2014 | Price et al. |
| 2014/0283826 A1 | 9/2014 | Murray et al. |
| 2014/0283831 A1 | 9/2014 | Foote et al. |
| 2014/0283841 A1 | 9/2014 | Chodkowski et al. |
| 2014/0283842 A1* | 9/2014 | Bearne .............. A61M 16/0666 |
| | | 128/206.24 |
| 2014/0283843 A1 | 9/2014 | Eves et al. |
| 2014/0305439 A1 | 10/2014 | Chodkowski et al. |
| 2014/0311494 A1 | 10/2014 | Gibson et al. |
| 2014/0360503 A1 | 12/2014 | Franklin et al. |
| 2015/0028519 A1 | 1/2015 | Lang et al. |
| 2015/0059759 A1 | 3/2015 | Frater et al. |

| | | |
|---|---|---|
| 2015/0083124 A1 | 3/2015 | Chodkowski et al. |
| 2015/0083136 A1 | 3/2015 | Grashow et al. |
| 2015/0105590 A1 | 4/2015 | Xiao |
| 2015/0128952 A1 | 5/2015 | Matula, Jr. et al. |
| 2015/0128953 A1 | 5/2015 | Formica et al. |
| 2015/0196726 A1 | 7/2015 | Skipper et al. |
| 2015/0246199 A1 | 9/2015 | Matula, Jr. et al. |
| 2015/0290415 A1 | 10/2015 | Dunn |
| 2016/0045700 A1 | 2/2016 | Amarasinghe et al. |
| 2016/0074613 A1 | 3/2016 | Davidson et al. |
| 2016/0082214 A1* | 3/2016 | Barlow ............. A61M 16/0622 |
| | | 128/206.24 |
| 2017/0056611 A1 | 3/2017 | Frater et al. |
| 2017/0136200 A1 | 5/2017 | Matula, Jr. |
| 2017/0304577 A1 | 10/2017 | Bearne et al. |
| 2018/0008452 A1 | 1/2018 | Wade |
| 2018/0099113 A1 | 4/2018 | Bell et al. |
| 2018/0169367 A1 | 6/2018 | Chodkowski et al. |
| 2018/0250486 A1 | 9/2018 | Amarasinghe et al. |

FOREIGN PATENT DOCUMENTS

| | | |
|---|---|---|
| DE | 202014104150 U1 | 9/2014 |
| EP | 1163923 | 12/2001 |
| EP | 1972357 A1 | 9/2008 |
| EP | 2060294 B1 | 5/2009 |
| EP | 2303379 | 4/2011 |
| EP | 1152787 A1 | 11/2011 |
| EP | 2452716 | 5/2012 |
| EP | 2470246 | 7/2012 |
| EP | 2501425 | 9/2012 |
| FR | 2390116 | 12/1978 |
| GB | 472897 | 9/1937 |
| GB | 521282 | 5/1940 |
| GB | 960115 A | 6/1964 |
| GB | 1072741 A | 6/1967 |
| GB | 2385533 | 8/2003 |
| WO | WO 1999006116 | 2/1999 |
| WO | WO 2000050122 A1 | 8/2000 |
| WO | WO 2001062326 | 8/2001 |
| WO | WO 2002007806 | 1/2002 |
| WO | WO 2002047749 | 6/2002 |
| WO | WO 2003013657 | 3/2003 |
| WO | WO 2003039637 | 5/2003 |
| WO | WO 2003076020 | 9/2003 |
| WO | WO 2004041325 | 5/2004 |
| WO | WO 2004071565 | 8/2004 |
| WO | WO 2005032634 | 4/2005 |
| WO | WO 2005118042 | 12/2005 |
| WO | WO 2008030831 | 3/2008 |
| WO | WO 2008063923 | 5/2008 |
| WO | WO 2009026627 | 3/2009 |
| WO | WO 2009/059353 | 5/2009 |
| WO | WO 2009/148956 A2 | 12/2009 |
| WO | WO 2010/066004 | 6/2010 |
| WO | WO 2010073142 | 7/2010 |
| WO | WO 2012/045127 | 4/2012 |
| WO | WO 2012040791 | 4/2012 |
| WO | 2013064950 A1 | 5/2013 |
| WO | WO 2013066195 | 5/2013 |
| WO | WO 2013175409 | 11/2013 |
| WO | 2014015382 A1 | 1/2014 |
| WO | WO 2014025267 A1 | 2/2014 |
| WO | WO 2014045245 A | 3/2014 |
| WO | WO 2014110622 A1 | 7/2014 |
| WO | WO 2014165906 | 10/2014 |
| WO | WO 2014175753 A1 | 10/2014 |
| WO | WO 2015006826 | 1/2015 |
| WO | WO 2015068067 | 5/2015 |
| WO | WO 2015070289 | 5/2015 |
| WO | WO 2015092621 | 6/2015 |
| WO | WO 2015161345 | 10/2015 |
| WO | WO 2016041008 | 3/2016 |
| WO | WO 2016041019 | 3/2016 |

* cited by examiner

40' APPROX

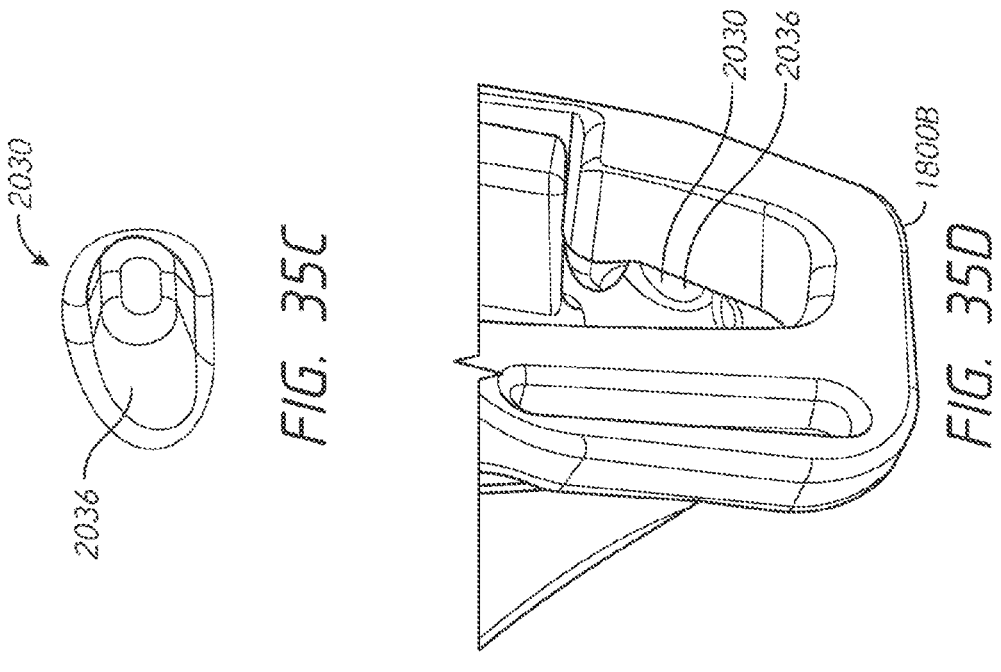
*FIG. 35C*
*FIG. 35D*
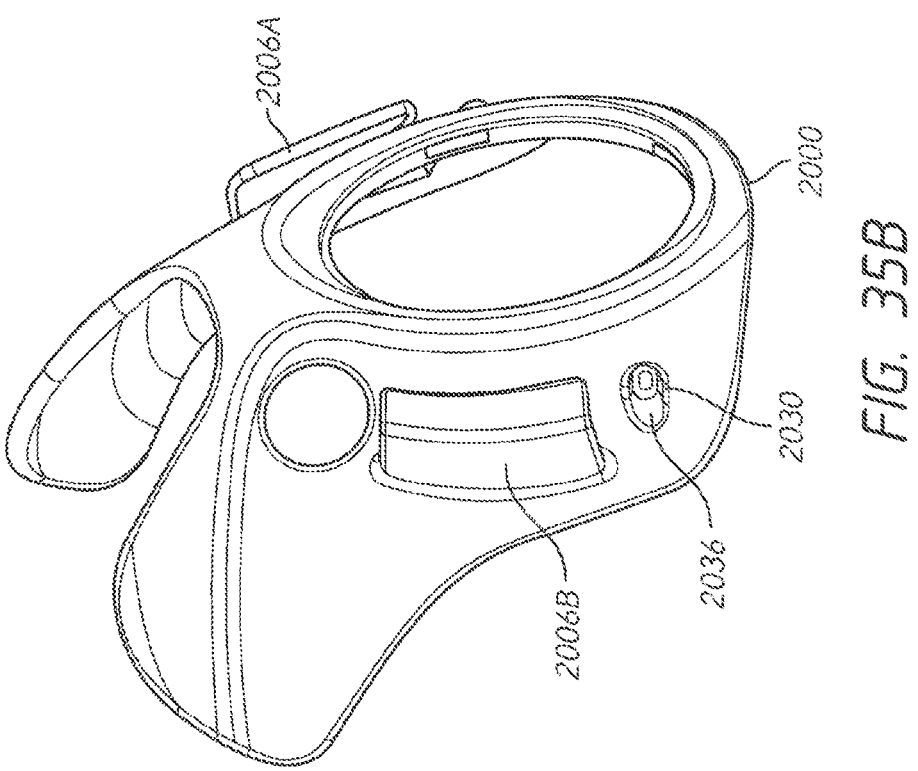
*FIG. 35B*

PATIENT INTERFACE

INCORPORATION BY REFERENCE

Any and all applications for which a foreign or domestic priority claim is identified in the Application Data Sheet as filed with the present application are hereby incorporated by reference herein and made a part of the present disclosure. Any applications identified herein or appended hereto are also incorporated by reference.

BACKGROUND

Technical Field

The present disclosure generally relates to patient interfaces.

Description of the Related Art

In patients suffering from obstructive sleep apnea (OSA), muscles that normally keep the upper airway open relax during slumber to the extent that the airway is constrained or completely closed off, a phenomenon often manifesting itself in the form of snoring. When this occurs for a period of time, the patient's brain typically recognizes the threat of hypoxia and partially wakes the patient in order to open the airway so that normal breathing may resume. The patient may be unaware of these waking episodes, which may occur as many as several hundred times per session of sleep. This partial awakening may significantly reduce the quality of the patient's sleep, over time potentially leading to a variety of symptoms, including excessive daytime sleepiness, chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that will reduce the frequency and/or duration of apneas, hypopneas, and/or flow limitations. The therapy is often implemented by using a positive airway pressure device to deliver a pressurized stream of air through a conduit to a patient through a patient interface or mask positioned on the face of the patient.

SUMMARY

A patient interface for use with PAP therapy or other respiratory therapies involving the administration of gas can comprise headgear that helps to retain the patient interface on the face of a user. The headgear generally interfaces with a frame that serves as a channel through which gas is delivered to the patient. The headgear comprises one or more straps that pass around the user's head. The headgear used preferably allows the frame and/or a cushion or sealing surface attached to the frame to be applied to the head of the user with a degree of force such that a therapeutically effective seal is obtained without compromising the comfort of fit to the user. Additionally, once properly fitted to the user's head, the headgear preferably is reasonably stable or resistant to movement or sliding. Headgear with one or more of the above qualities is desired.

Certain features, aspects and advantages of at least one of the configurations disclosed herein include the realization that a patient interface can have features that improve the comfort of use of a patient interface, particularly when a nose-contacting portion of the patient interface is urged towards the nose. The patient interface can have rigid headgear connection elements connectable to the frame of the respiratory interface. The rigid headgear connection elements can be shaped to reduce the force of the cushion against the nose. Additionally, certain features, aspects and advantages of at least one of the configurations disclosed herein include the realization that headgear for a patient interface can have features that can improve the stability of the headgear on the head. The headgear can have a relatively rigid framework and a relatively pliable or soft overlay covering the framework. The rigid framework can have apertures defining a front portion to be positioned below or near the cheekbones, a rear portion to be positioned over the sides of the head around the ears, and a top portion to extend upward along the head towards the crown.

Thus, in accordance with certain features, aspects and advantages of at least one of the configurations disclosed herein, a patient interface is disclosed. The patient interface can comprise a frame adapted to be positioned away from the face of a user, the frame comprising a side aperture configured to accept a headgear connection element, wherein at least a portion of a wall of the frame defining the side aperture comprises a depressed portion adapted to hold the headgear connection element, and wherein the depressed portion extends into the frame towards the face of the user.

In some configurations, the depressed portion extends towards the middle of the frame.

In some configurations, the depressed portion is skewed such that the depressed portion extends towards the middle of the frame in a direction offset from the horizontal.

In some configurations, the side aperture is positioned within the outer perimeter of the frame.

In some configurations, the side aperture extends through the frame in a direction towards the face of the user.

In some configurations, a gases passageway adapted to channel gases to the user is defined through the frame.

In some configurations, the frame is adapted to interface with a cushion module adapted to be placed on the face of the user.

Additionally, in accordance with certain features, aspects and advantages of at least one of the configurations disclosed herein, a patient interface is disclosed. The patient interface comprises a frame adapted to be positioned away from the face of a user, the frame comprising a side aperture configured to accept a headgear connection element, and a headgear connection element extending from the frame, the headgear connection element that contacts and provides a resistive force against the head of the user; wherein the headgear connection element comprises a progressive feedback element adapted to apply increasing levels of force to the head of the user as the headgear connection element is urged towards the head of the user.

In some configurations, the progressive feedback element comprises a cantilever element. In some such configurations, the headgear connection element has an aperture and the cantilever element comprises a cantilever extension that projects outwardly from a wall defining the aperture in the headgear connection element.

In some configurations, the progressive feedback element comprises a resilient cushion adapted to contact the head of the user. In some such configurations, all of the force transmitted by the progressive feedback element to the head of the user is transmitted through the cushion.

In some configurations, a substantially linear relationship exists between the force exerted by the progressive feedback element and the force with which the headgear connection element is urged towards the head of the user. In some configurations, a substantially non-linear relationship exists between the force exerted by the progressive feedback element and the force with which the headgear connection element is urged towards the head of the user.

In some configurations, the progressive feedback element is positioned on the headgear connection element such that the progressive feedback element applies force to the cheeks of the user. In some such configurations, the progressive feedback element only applies force to the cheeks of the user.

In some configurations, the progressive feedback element is positioned at or about the middle of the headgear connection element.

Additionally, in accordance with certain features, aspects and advantages of at least one of the configurations disclosed herein, a headgear connection element is disclosed. The headgear connection element comprises a first end adapted to interface with headgear, a second end adapted to interface with a frame of a patient interface, and a body extending between the first and second ends substantially along a first axis. The second end comprises a projection comprising a first portion extending along a second axis substantially transverse to the first axis and a second portion extending from the first portion in a direction substantially parallel to the first axis, the projection adapted to protrude through the frame of the patient interface.

In some configurations, the first portion is substantially mushroom-shaped.

In some configurations, the first portion is lower in cross-sectional area than the second portion.

In some configurations, the body curves inwardly in a direction towards the frame. In some such configurations, the body curves inwardly into a depressed region at or near the second end, wherein the projection extends outwardly from the depressed region.

In some configurations, the headgear connection element may further comprise a progressive feedback element adapted to apply increasing levels of force to the head of the user as the headgear connection is urged towards the head of the user. In some such configurations, the progressive feedback element comprises a cantilever element. The cantilever element can comprise a cantilever extension that projects outwardly from a wall defining an aperture in the headgear connection element. In some configurations, the progressive feedback element can comprise a cushion adapted to be placed on the head of the user. All of the force transmitted by the progressive feedback element may be transmitted through the cushion. In some configurations, a substantially linear relationship exists between the force exerted by the progressive feedback element and the force with which the headgear connection element is urged towards the head of the user. In other configurations, a substantially non-linear relationship exists between the force exerted by the progressive feedback element and the force with which the headgear connection element is urged towards the head of the user. In some configurations, the progressive feedback element may be positioned such that the progressive feedback element applies force to the cheeks of the user. In some configurations, the progressive feedback element may be positioned at, about or near the middle of the body.

Additionally, in accordance with certain features, aspects and advantages of at least one of the configurations disclosed herein, a headgear connection element is disclosed. The headgear connection element comprises a first end adapted to interface with headgear, a second end adapted to interface with a frame of a patient interface, and a body extending between the first and second ends; wherein the first end comprises a slot defined between the body and a pair of legs positioned at an edge of the first end, the slot comprising a gap through which a headgear strap is inserted and looped around the pair of legs.

In some configurations, the pair of legs comprises a bottom leg of a first length and a top leg of a second length. The first length may be greater than the second length.

In some configurations, a protrusion extends outwardly from an inside edge of the bottom leg and towards the body.

In some configurations, the headgear connection element may comprise one or more of the features of the headgear connection elements described above or elsewhere in this disclosure.

Additionally, in accordance with certain features, aspects and advantages of at least one of the configurations disclosed herein, a headgear assembly is disclosed. The headgear assembly comprises a framework adapted to face away from the head, the framework comprising apertures defining a front portion adapted to be positioned below or near the cheekbones, a rear portion adapted to be positioned over the sides of the head around the ears, and a top portion adapted to extend upward along the head towards the crown. The headgear assembly also comprises an overlay attached to the framework and adapted to contact the head. The overlay may be constructed at least in part from a material having a lower modulus of elasticity, lower flexural modulus, and/or greater softness than the framework.

In some configurations the framework further comprises a crown portion adapted to be positioned over the crown of the head.

In some configurations, the overlay may be joined directly to the framework.

In some configurations, the overlay may be shaped such that the overlay covers the entire framework.

In some configurations, the overlay may occlude only the apertures defining the front and top portions.

In some configurations, the aperture defining the rear portion is substantially polygonal. In some such configurations, the aperture defining the rear portion is substantially hexagonal.

In some configurations, the aperture defining the front portion is substantially trapezoidal.

In some configurations, the aperture defining the top portion is substantially triangular or trapezoidal.

In some configurations, the overlay comprises air apertures configured to increase the breathability of the overlay.

Additionally, in accordance with certain features, aspects and advantages of at least one of the configurations disclosed herein, an overlay for a headgear assembly is disclosed. The overlay comprises a front portion adapted to be positioned below or near the cheekbones, an aperture defining a rear portion adapted to be positioned over the sides of the head around the ears, and a top portion adapted to extend upward along the head towards the crown.

In some configurations, the overlay comprises air apertures configured to increase the breathability of the overlay. In some such configurations, the air apertures are positioned only on the front and top portions of the overlay. In some such configurations, the air apertures are arranged in a triangle-like pattern on the top portion of the overlay. In some such configurations, the air apertures are arranged in a rectangle-like pattern on the front portion of the overlay. In some such configurations, the air apertures are substantially circular. In other such configurations, the air apertures may be substantially polygonal.

In some configurations, the overlay further comprises a back support portion extending outwardly from a section of the rear portion distal from the front portion, the back support portion having a smaller width than the section of the rear portion from which the back support portion extends.

Additionally, in accordance with certain features, aspects and advantages of at least one of the configurations disclosed herein, a headgear assembly is disclosed. The headgear assembly comprises left and right frameworks adapted to face away from the head, the frameworks comprising apertures defining front portions adapted to be positioned below or near the cheekbones, rear portions adapted to be positioned over the sides of the head around the ears, and top portions adapted to extend upward along the head towards the crown; left and right overlays adapted to contact the head, the left and right overlays joined to the left and right frameworks and shaped such that they match the shapes of the frameworks; wherein the overlays are constructed at least in part from a material having a lower modulus of elasticity, lower flexural modulus and/or greater softness than the frameworks.

In some configurations, the frameworks and/or overlays are connected by a back panel or section adapted to support the back of the head. In some such configurations, the back panel is configured to be substantially placed only over the occipital portion of the skull. In some such configurations, the width of the back panel is lower at or around the middle of the back panel than at the edges. In some such configurations, the back panel comprises a lower modulus of elasticity and/or higher breathability than the frameworks and/or overlays. In some such configurations, the back panel tapers in width from the sections linked to the frameworks and/or overlays towards a minimum width at or near the middle of the back panel.

In some configurations, the left and right overlays are configured to occlude only the apertures defining the front and top portions of the frameworks.

In some configurations, the apertures defining the rear portions of the frameworks are substantially polygonal. In some such configurations, the apertures defining the rear portions of the frameworks are substantially hexagonal.

In some configurations, the apertures defining the front portions of the frameworks are substantially trapezoidal.

In some configurations, the apertures defining the top portions of the frameworks are substantially triangular or trapezoidal.

In some configurations, the overlays comprise air apertures configured to increase the breathability of the overlays. In some such configurations, the air apertures are positioned only on the front and top portions of the overlays. In some such configurations, the air apertures are arranged in triangle-like patterns on the front portions of the overlays. In some such configurations, the air apertures are arranged in rectangle-like patterns on the front portions of the overlays. In some such configurations, the air apertures are substantially circular. In some other such configurations, the air apertures are substantially polygonal.

Additionally, in accordance with certain features, aspects and advantages of at least one of the configurations disclosed herein, a headgear assembly for securing a user interface onto a head of a user is disclosed. The headgear assembly comprises ear loop portions configured to be positioned on right and left sides of the head and surrounding ears of the user. Crown straps are attached to the ear loop portions and extend upwards from the ear loop portions. The crown straps overlap over a crown of the head of the user and fasteners connect the crown straps. Top straps are attached to the ear loop portions, extend forward towards the user interface, and are connected to the user interface. Bottom straps are positioned below the top straps, attached to the ear loop portions, extend horizontally with respect to the user toward the user interface, and are connected to the user interface. In some configurations, a back panel connects the ear loop portions together.

In some configurations, the top straps extend at an angle relative to the bottom straps in a lengthwise direction towards the bottom straps.

In some configurations, the angle is within a range of 0 to 25 degrees.

In some configurations, the angle is 12 degrees.

In some configurations, an angle between a lengthwise direction of the crown strap and a lengthwise direction of the top straps is within a range of 100 to 150 degrees.

In some configurations, the angle between a lengthwise direction of the crown strap and a lengthwise direction of the top straps is equal to 118 degrees.

In some configurations, a segment of the ear loop portion connecting the crown strap to the top strap is tangent to the crown strap.

In some configurations, the segment of the ear loop portion connecting the crown strap to the top strap is tangent to the top strap.

In some configurations, the fasteners are spaced apart at an increment distance along a length of the crown straps.

In some configurations, the increment distance is 23.5 mm.

In some configurations, the fasteners further include male elements positioned on one crown strap and female elements positioned on the other crown strap. The male elements are connected to the female elements to fasten the crown straps together.

In some configurations, the female elements further include through-holes that extend through the crown strap. The male elements further include protrusions that protrude from the crown strap. The through-holes and the protrusions have corresponding shapes.

In some configurations, the user interface further includes slots through which the top and bottom straps are connected. The slots have at least one of a height or a width that is narrower than a height or a width of the top and bottom straps.

In some configurations, the height of the upper slot is greater than the height of the lower slot.

Additionally, in accordance with certain features, aspects and advantages of at least one of the configurations disclosed herein, a headgear assembly for a patient interface is disclosed. The headgear assembly includes ear loops configured to be positioned on left and right sides of the head of a user and to surround the ears and crown straps attached to the ear loops and extending upwards from the ear loops. The crown straps overlap over a crown of the head of the user and one or more fasteners connect the crown straps. The headgear assembly further includes top straps attached to the ear loops, extending forwardly towards the user interface, and connected to the user interface, and bottom straps positioned below the top straps, attached to the ear loops, extending horizontally with respect to the user toward the user interface, and connected to the user interface, wherein the top straps extend at an angle relative to the bottom straps in a lengthwise direction towards the bottom straps.

In some configurations, the angle is between 0 degrees and 25 degrees.

In some configurations, the angle is 12 to 15 degrees.

In some configurations, an angle between a lengthwise direction of the crown strap and a lengthwise direction of the top straps is within 100 to 150 degrees.

In some configurations, the angle between the lengthwise direction of the crown strap and the lengthwise direction of the top straps is 115 to 118 degrees.

In some configurations, a segment of each ear loop connecting the crown strap to the top strap is tangent to the crown strap.

In some configurations, the fasteners are spaced apart an increment distance along a length of the crown straps.

In some configurations, the increment distance is between 22 and 24 mm.

In some configurations, the fasteners include male elements positioned on one crown strap and female elements positioned on the other crown strap, the male elements are connected to the female elements to fasten the crown straps together.

In some configurations, the female elements include through-holes that extend through the crown strap, and the male elements include protrusions that protrude from the crown strap, wherein the through-holes and protrusions have corresponding shapes.

In some configurations, at least the ear loops and crown straps include a rigid frame, the rigid frame providing structure and support to the ear loops and crown straps.

In some configurations, the ear loops and crown straps include overlay layers sandwiching the rigid frame such that the rigid frame is disposed between two overlay layers, the overlay layers providing a comfortable user contacting side.

In some configurations, the overlay layers have at least one of a lower modulus of elasticity, a lower flexural modulus, or a greater softness than the rigid frame.

In some configurations, the overlay layers are formed from a fabric material.

In some configurations, the rigid frame includes a top and bottom strap connecting segment that is a portion of the rigid frame that connects the top and bottom straps. The top and bottom strap connecting segment is positioned along the cheekbones of the user.

In some configurations, the rigid frame includes segments that extend from positions adjacent the ear and/or cheek and are connected to the crown strap to transmit loads to the crown strap.

In some configurations, the headgear includes a back panel that is connected to the ear loops, the back panel extending along a rear of the user's head.

In some configurations, the back panel includes a contoured section of the bottom edge such that the back panel rests above the neck and bears on the base of the skull.

In some configurations, the back panel is formed from a soft and stretchable material.

Additionally, in accordance with certain features, aspects and advantages of at least one of the configurations disclosed herein, a patient interface is disclosed. In some configurations, the patient interface includes an interface frame, a cushion module removably connected to the interface frame. The cushion module includes a shell and a soft cushion that is connected to the shell, the cushion module having an under nose sealing portion and an oral sealing portion. The patient interface also includes a headgear assembly removably connected to the interface frame. The headgear assembly includes a headgear frame. The headgear frame includes a plurality of segments that extend around the ears, along the cheekbone and along the crown. The headgear assembly also includes an overlay, the overlay having two layers, the headgear frame being disposed between the two layers of the overlay, and the overlay being formed from a softer material than the headgear frame.

In some configurations, the headgear assembly also includes ear loops that extend around the ear.

In some configurations, the headgear assembly also includes crown straps that extend along the top of the user's head and are removably connectable to each other.

In some configurations, the headgear assembly also includes fasteners that connect the crown straps together.

In some configurations, a segment of the ear loops connecting the crown strap to the top strap is tangent to the crown strap.

In some configurations, the fasteners are spaced apart at an increment distance along a length of the crown straps.

In some configurations, the increment distance is between 22 and 24 mm.

In some configurations, the fasteners further include male elements positioned on one crown strap and female elements positioned on another crown strap, the male elements are connected to the female elements to fasten the crown straps together.

In some configurations, the female elements further include through-holes that extend through the crown strap. The male elements further include protrusions that protrude from the crown strap, wherein the through-holes and protrusions have corresponding shapes.

In some configurations, the headgear assembly also includes a back panel that is connected to the ear loops, the back panel extending along a rear of the user's head.

In some configurations, the back panel includes a contoured section of the bottom edge such that the back panel rests above the neck and bears on the base of the skull.

In some configurations, the back panel is formed from a soft and stretchable material.

In some configurations, the patient interface also includes one or more clips to removably couple the headgear assembly to the interface frame. The clips include a female fixation element configured to engage with a male fixation element on the mask frame.

In some configurations, the female fixation element is a cut-out portion in the body of the clip.

In some configurations, the interface frame includes a ridge portion that extends upwardly from the interface frame and is received by the female fixation element.

In some configurations, the clip includes one or more magnetic elements that are spaced apart from each other and are aligned along a vertical axis with respect to the user.

In some configurations, the interface frame includes corresponding magnetic elements to interface with the magnetic elements of the clip to retain the clip on the interface frame.

Additionally, in accordance with certain features, aspects and advantages of at least one of the configurations disclosed herein, a patient interface is disclosed. In some configurations, the patient interface includes a frame, and a cushion module, the cushion module being removably connected to the frame. The cushion module includes left and right upper cushion ridges shaped and configured to extend along the sides of the nose. The cushion module also includes a nasal recess with a nasal opening. The nasal recess is configured to receive a portion of the nose and the nasal recess is configured to create a seal with the underside of the nose, and a pair of headgear connection elements that extend outwardly from the frame. The headgear connection elements are shaped to extend across at least a portion of the patient's cheeks. The headgear connection elements are arranged to interface with and removably couple to a headgear assembly.

In some configurations, each headgear connection element includes a projection at the end that connects to the frame. The projection includes a substantially mushroom shaped element that is configured to protrude through an opening in the frame to couple the headgear connection element to the frame.

In some configurations, the headgear connection element includes an arcuate shaped body that extends upwardly toward from the connection between the frame and the headgear connection element.

In some configurations, the headgear connection element includes a slot positioned at a free end of the headgear connection element, the free end being distal to the connection between the frame and the headgear connection element.

In some configurations, the slot is defined by a pair of legs and configured to receive a strap portion of the headgear assembly.

In some configurations, the headgear connection element includes a progressive feedback element that is configured to provide a force against the user's face commensurate with the fit of the patient interface.

In some configurations, the progressive feedback element is configured to provide a resistive force against the user's face to indicate the tightness of the headgear.

In some configurations, the frame further includes a pair of upper frame ridges that are configured to prevent the cushion module from over inflating.

In some configurations, the patient interface further includes a headgear assembly having ear loops that extend around the ear.

In some configurations, the headgear assembly includes crown straps that extend along the top of the user's head and are removably connectable to each other.

In some configurations, the headgear assembly includes fasteners that connect the crown straps together.

In some configurations, a segment of each ear loop that connects the crown strap to the top strap is tangent to the crown strap.

In some configurations, the fasteners are spaced apart at an increment distance along a length of the crown straps.

In some configurations, the headgear assembly includes a frame having a plurality of segments that extend around the ears, along the cheekbone and along the crown. The headgear assembly includes an overlay having two layers. The frame is disposed between the two layers of the overlay. The overlay is formed from a softer material than the frame.

In some configurations, the fasteners include male elements positioned on one crown strap and female elements positioned on the other crown strap. The male elements are connected to the female elements to fasten the crown straps together.

In some configurations, the female elements include through-holes that extend through the crown strap. The male elements include protrusions that protrude from the crown strap. The through-holes and protrusions have corresponding shapes.

In some configurations, the headgear assembly includes a back panel that is connected to the ear loops. The back panel extends along a rear of the user's head.

In some configurations, the back panel includes a contoured section of the bottom edge such that the back panel rests above the neck and bears on the base of the skull.

Additionally, in accordance with certain features, aspects and advantages of at least one of the configurations disclosed herein, a patient interface is disclosed. In some configurations, the patient interface includes a frame adapted to be positioned away from the face of a user. The frame includes a post protruding from the frame in a direction away from the face of a user. The post has a through-hole extending through the post. The patient interface also includes a headgear connection element. The headgear connection element includes an opening extending through the headgear connection element, and an insertion portion extending from the headgear connection element in a direction towards the opening. The post is positioned within the opening of the headgear connection element and the insertion portion is positioned within the through-hole of the post to connect the headgear connection element to the frame.

In some configurations, the insertion portion has a raised portion that protrudes from the insertion portion on a portion of the insertion portion that is positioned outside of the through-hole when the insertion portion is positioned within the through-hole, the raised portion configured to contact the post and retain the headgear connection element connected to the frame.

In some configurations, the frame includes an alignment portion protruding from the frame in a direction away from the face of a user. The headgear connection element includes an alignment recess positioned on a side of the headgear connection element that faces the frame, wherein the alignment portion is positioned within the alignment recess when the insertion portion is positioned within the through-hole of the post.

In some configurations, the opening has a post receiving portion that has a shape which corresponds with the shape of the post. The post receiving portion contacts the post to prevent rotation of the headgear connection element relative to the post.

In some configurations, the opening has tapered regions adjacent to and angled toward the post receiving portion to guide the post into engagement with the insertion portion.

BRIEF DESCRIPTION OF THE DRAWINGS

Specific embodiments and modifications thereof will become apparent to those skilled in the art from the detailed description herein having reference to the figures that follow, of which:

FIG. 35B shows a front perspective view of the mask frame of FIG. 31A to illustrate a locator guide.

FIG. 35C shows a close-up view of the locator guide.

FIG. 35D shows a close-up view of the connection element engaged with the locator guide.

DETAILED DESCRIPTION

Figure 1:
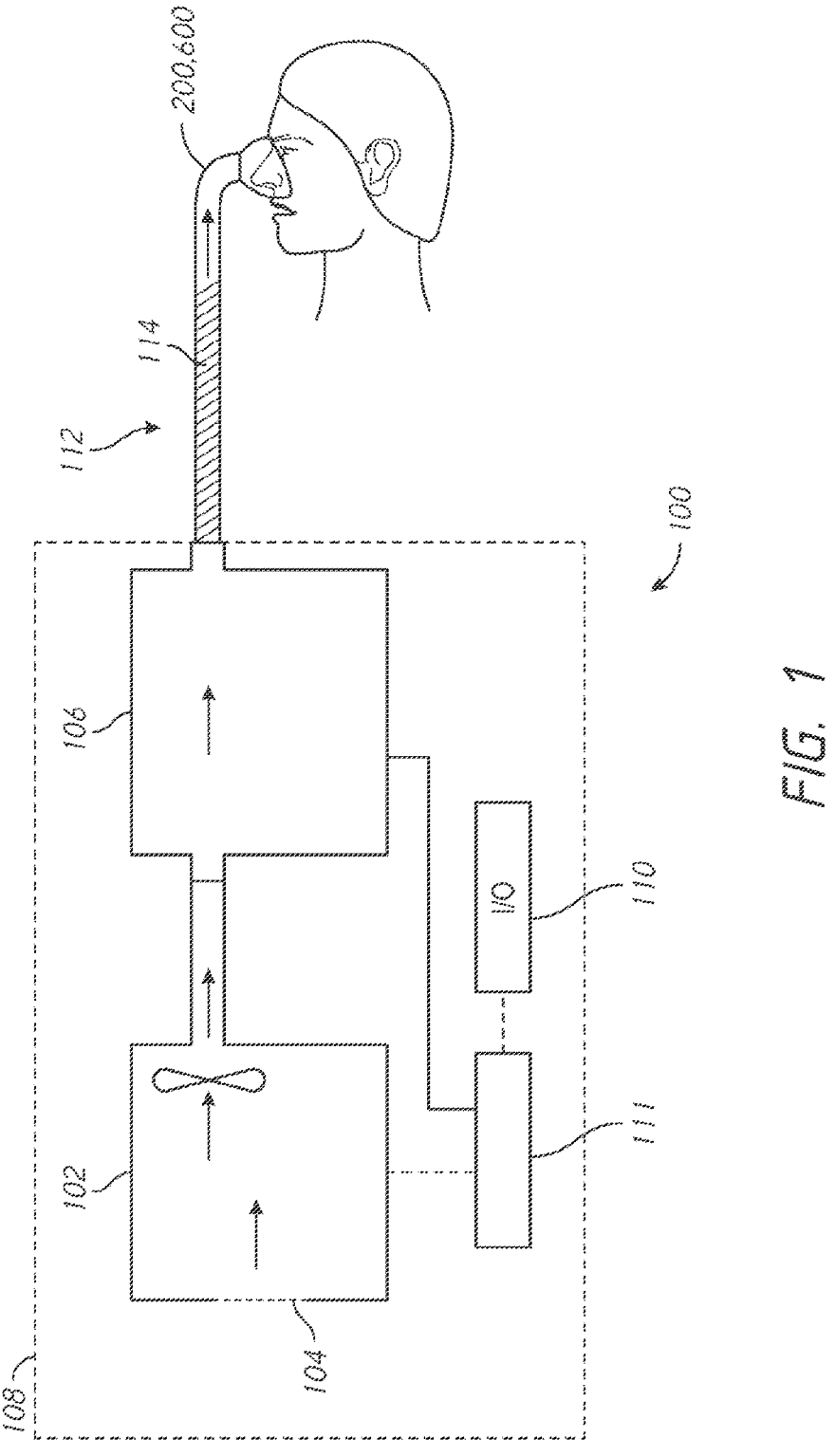
FIG. 1 shows a schematic diagram of a respiratory therapy system.

With reference to the non-limiting exemplary configuration illustrated in FIG. 1, a respiratory therapy system 100 is shown. The respiratory therapy system 100 comprises a flow generator 102. The flow generator 102 comprises a PAP device. The flow generator 102 receives gases from a gases inlet 104 and propels them to a humidifier 106. The flow generator 102 and humidifier 106 may be part of an integrated flow delivery system or may share a housing 108. The humidifier 106 heats and humidifies the gases. Heated and humidified gases are passed from a humidifier outlet to a gases conduit 112. The gases conduit 112 comprises a heater 114. The heater 114 reduces or prevents the condensation of moisture along the walls of the gases conduit 112. Gases are passed from the gases conduit 112 to a patient interface 200, 600 through which they are delivered to a patient. The respiratory therapy system 100 comprises a controller 111 that controls the operation of the flow generator 102. The controller 111 also controls the operation of the humidifier 106. The respiratory therapy system 100 comprises an input/output (I/O) module 110. The I/O module 110 comprises a way for a user to interact with and set parameters for the flow generator 102 and/or humidifier 106 as well as receive information regarding the operation of the respiratory therapy system 100 and/or its components. The I/O module 110 may comprise, for example, buttons, knobs, dials, switches, levers, touch screens, speakers, displays and/or other input or output elements. In some configurations, the humidifier 106 may not be present. In some configurations, the gas conduit 112 may not have a heater 114. In some configurations, the flow generator 102 may comprise elements other than PAP devices, including but not limited to high flow therapy devices or ventilation devices.

Figure 2A:
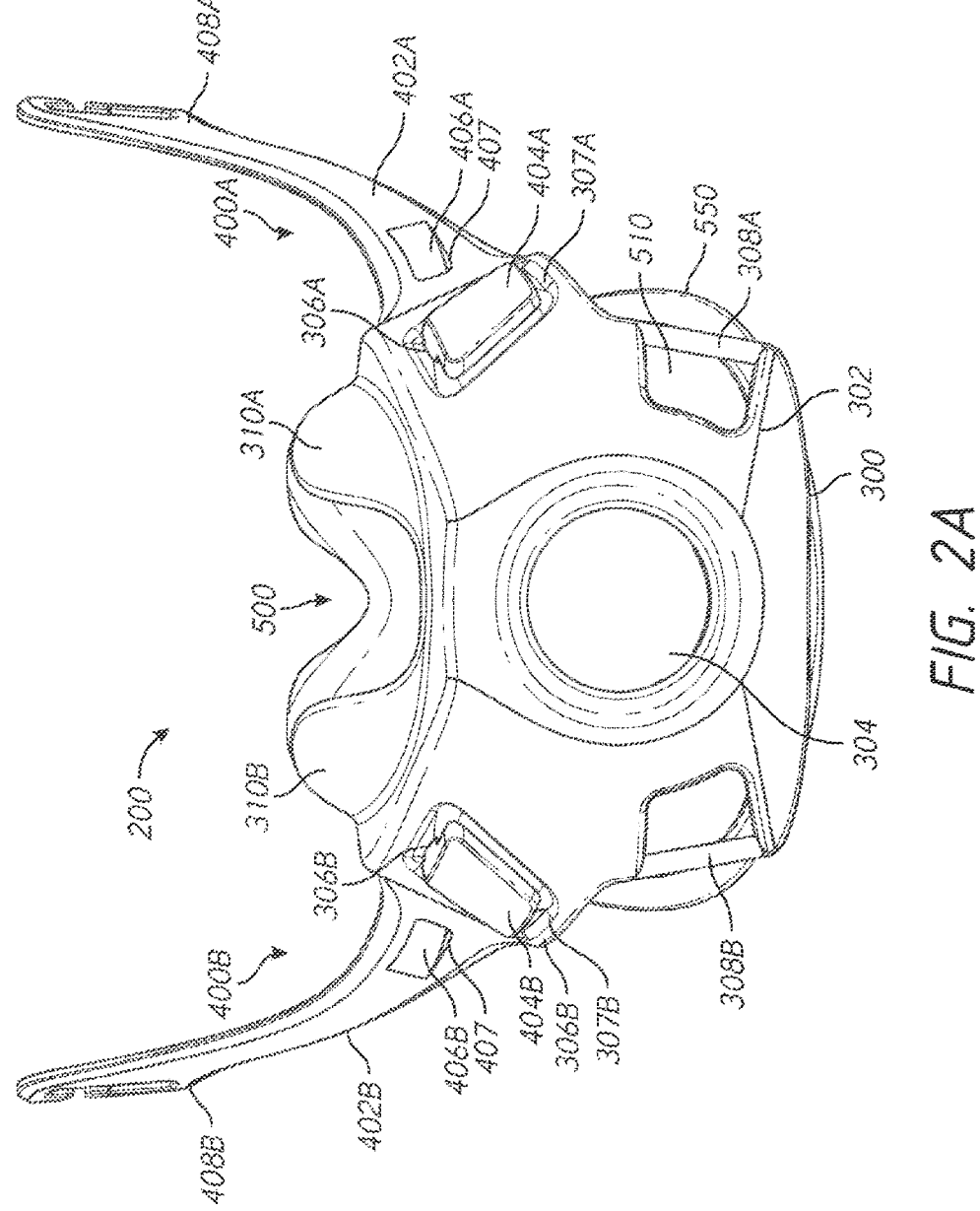
FIG. 2A shows a front plan view of a first patient interface.
Figure 2B:
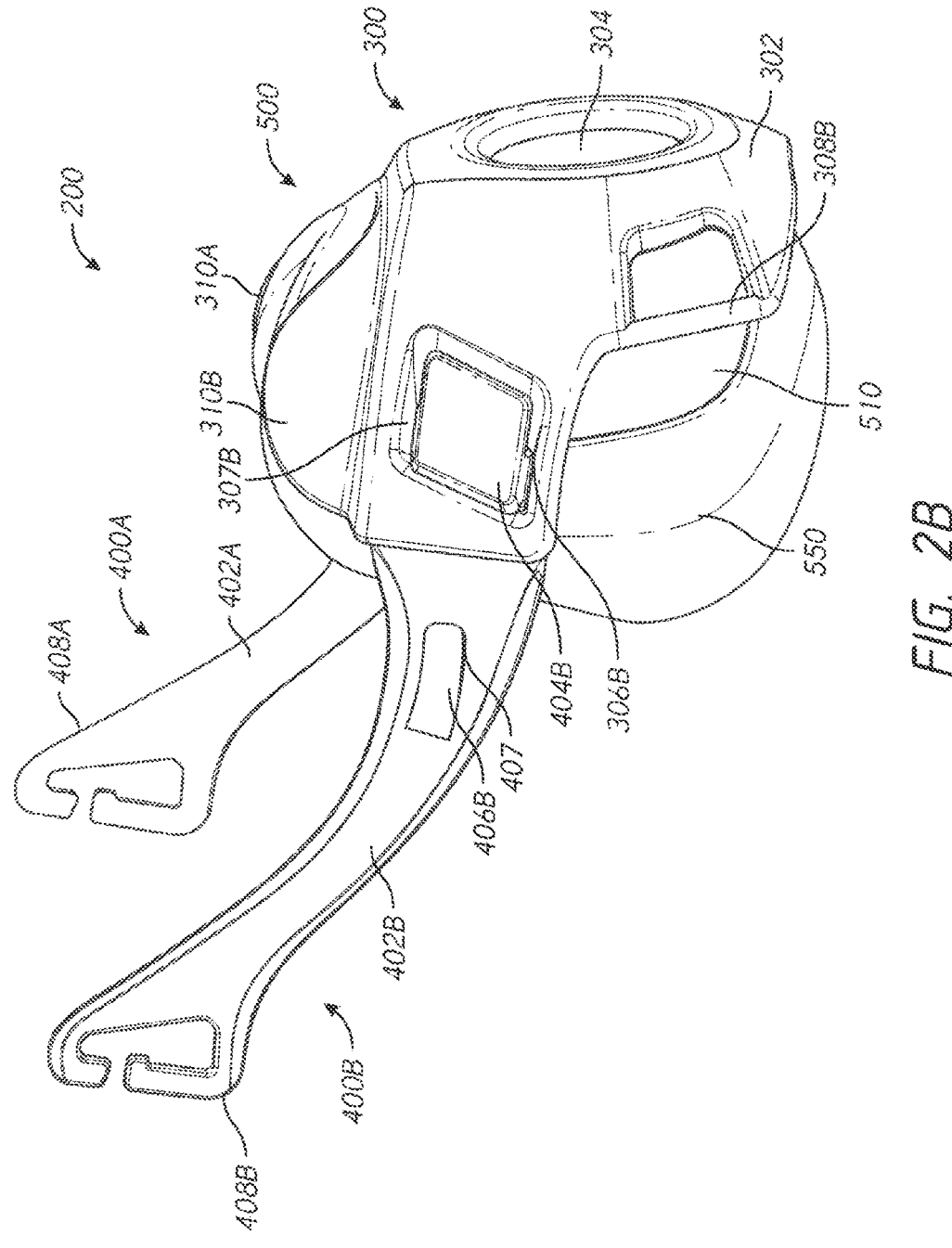
FIG. 2B shows a side plan view of the patient interface of FIG. 2A.
Figure 2C:
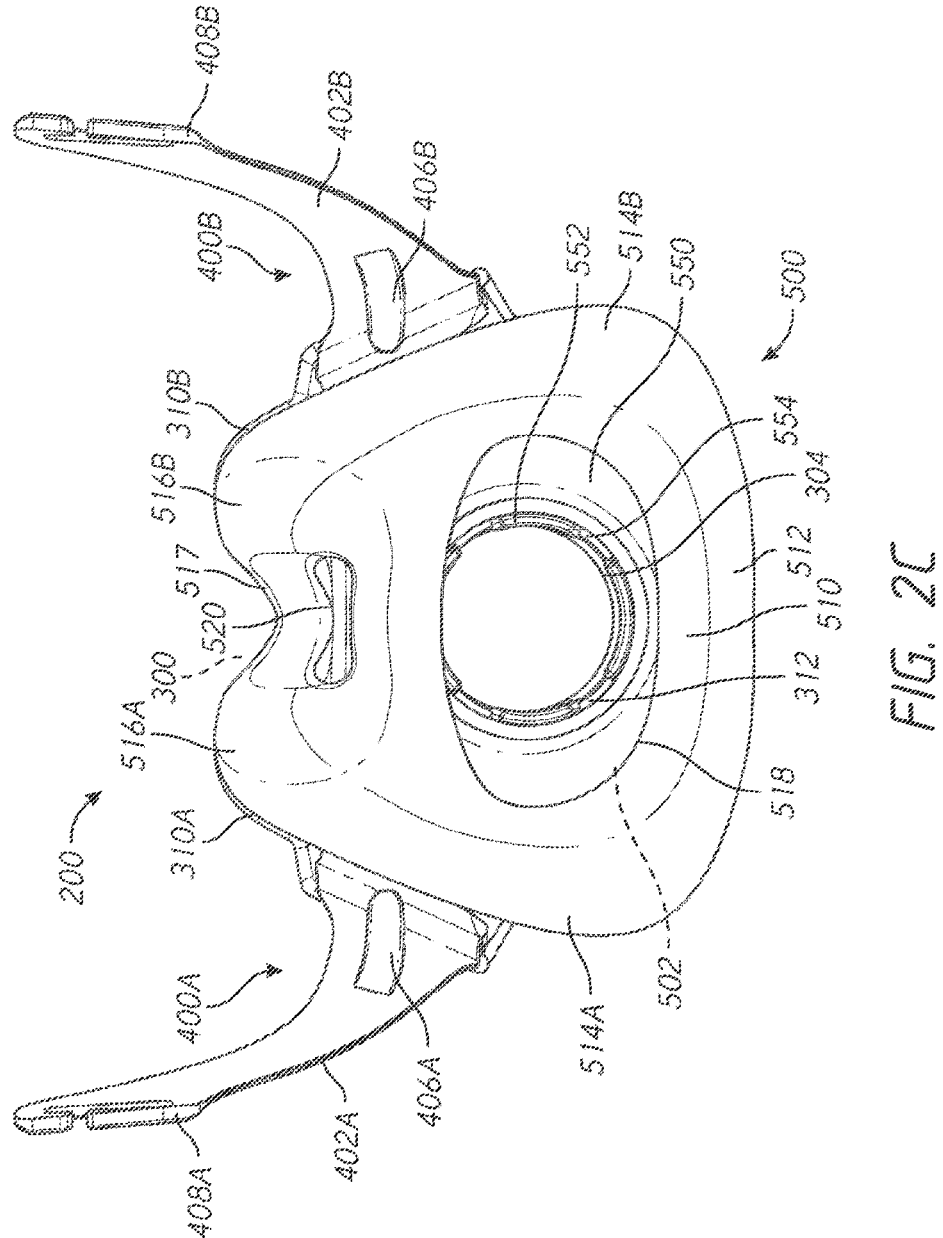
FIG. 2C shows a rear plan view of the patient interface of FIG. 2A.
Figure 2D:
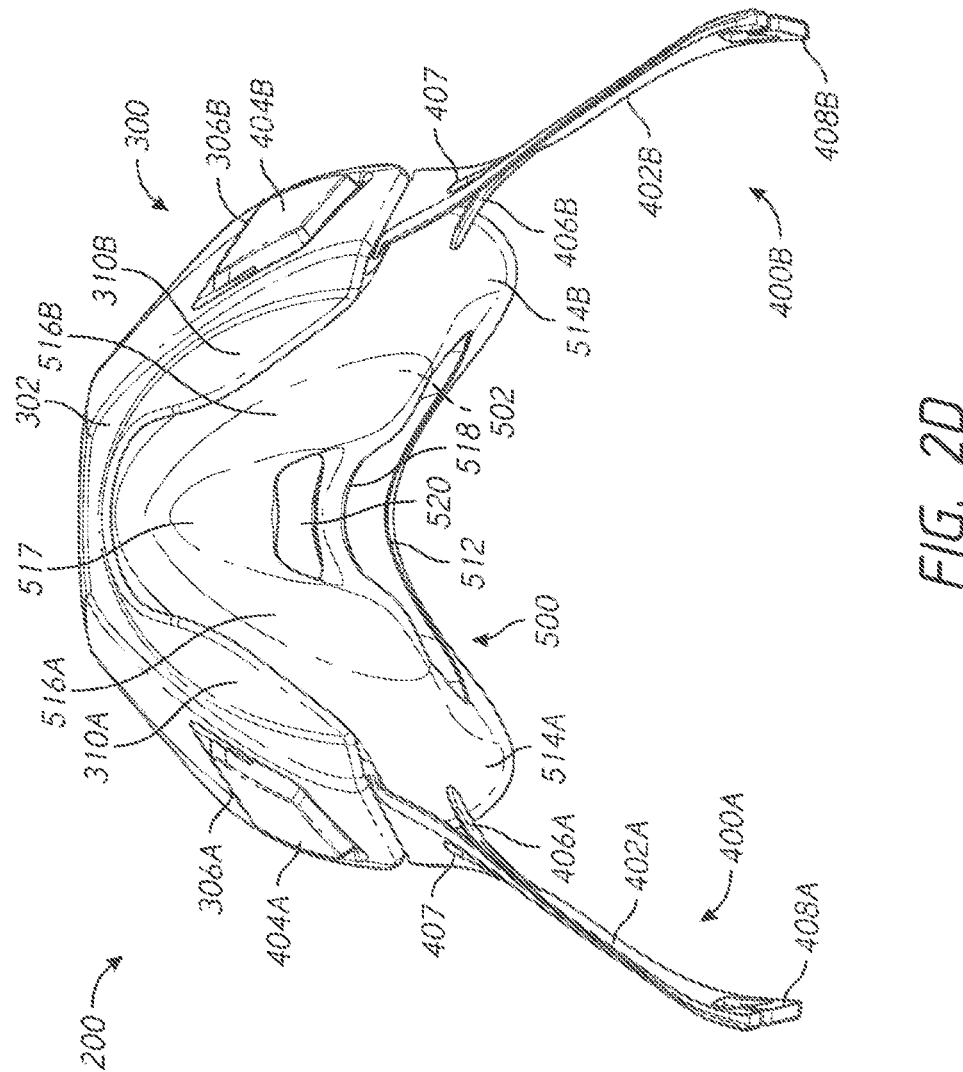
FIG. 2D shows a top plan view of the patient interface of FIG. 2A.
Figure 2E:
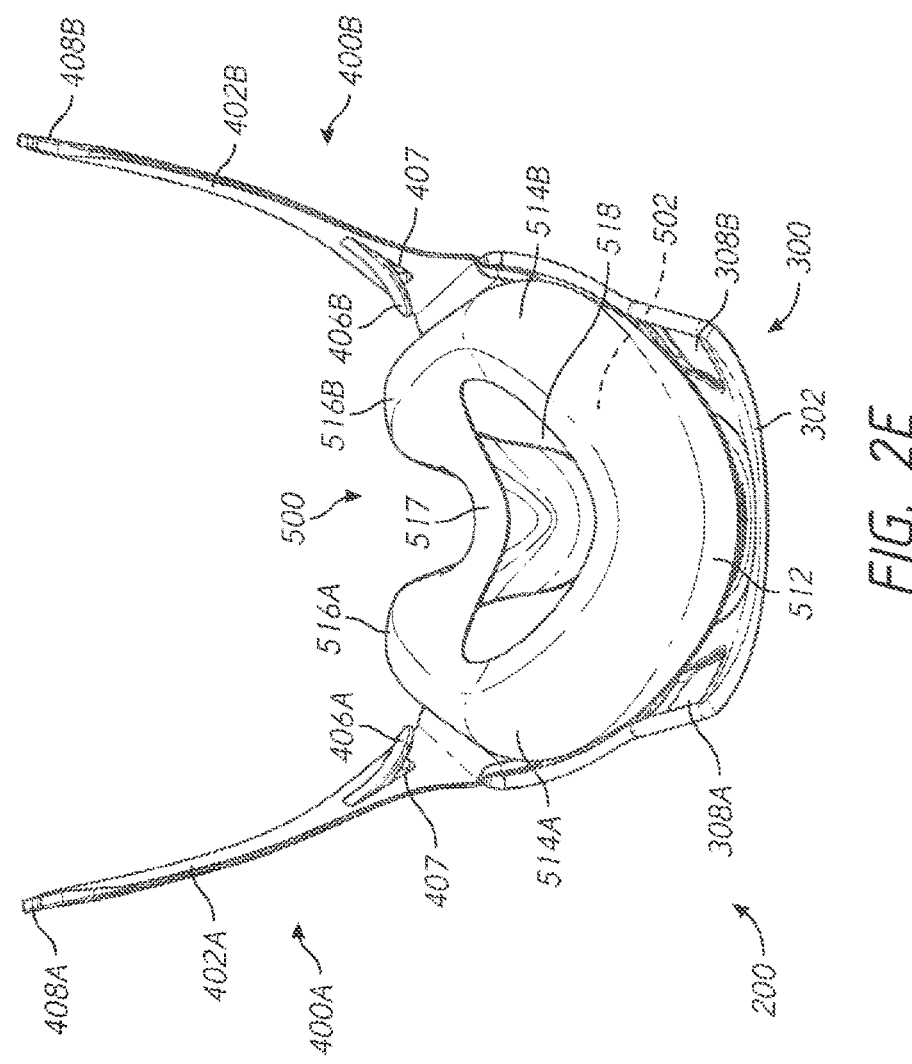
FIG. 2E shows a bottom plan view of the patient interface of FIG. 2A.
Figure 12:
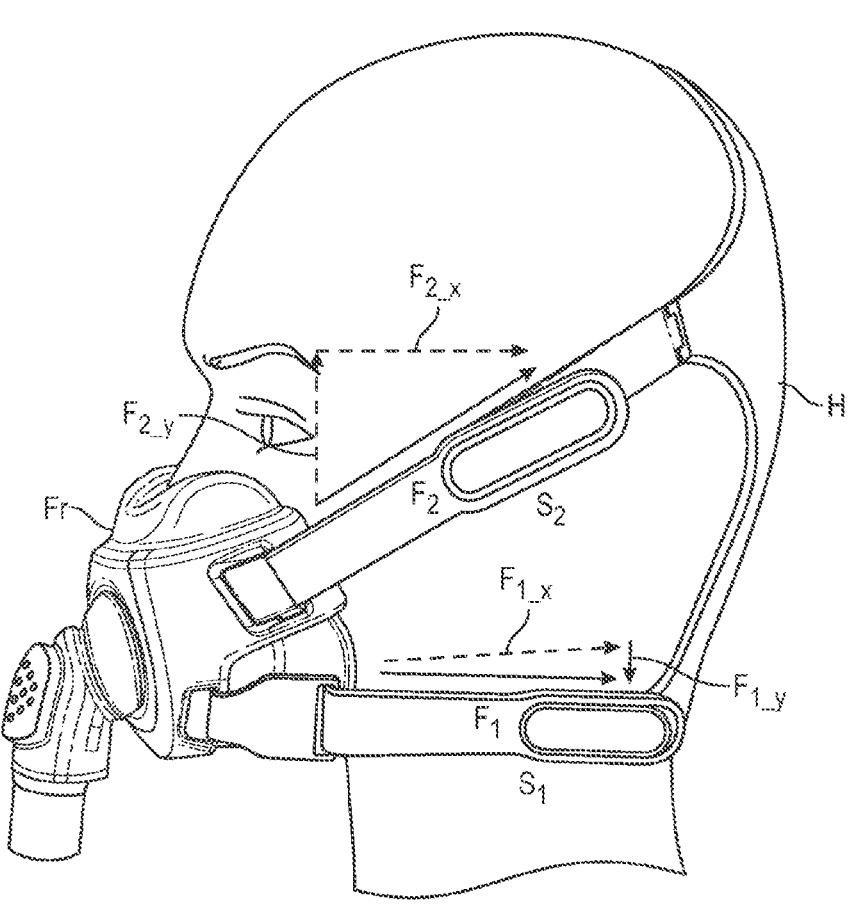
FIG. 12 shows forces applied to an alternative embodiment of a patient interface.

A first non-limiting exemplary patient interface 200 is shown in FIGS. 2A-2E. The patient interface 200 can be used with the respiratory therapy system 100 described with reference to FIG. 1. The patient interface 200 comprises a frame 300. The frame 300 is adapted to receive gases from a gases source (for example, the flow generator 102 described elsewhere in this disclosure with reference to FIG. 1). The frame 300 comprises a body 302, a gases aperture 304, left and right upper connection slots 306A, 306B, left and right lower connection slots 308A, 308B, left and right upper cushion supports 310A, 310B, and a cushion module retention portion defined by raised 312 and depressed 314 portions of a wall of the frame 300 defining the gases aperture 304 (see FIGS. 4A-4D). The left and right upper cushion supports 310A, 310B project generally upward from the body 302. The left and right upper cushion supports 310A, 310B are slightly angled toward each other such that the left and right upper cushion supports 310A, 310B extend along the lateral sides of the user's nose. Preferably, the left and right upper cushion supports 310A, 310B may be curvingly contoured and slightly offset a distance toward the user's nose relative to the body 302 (as shown in FIG. 2D) such that the left and right upper cushion supports 310A, 310B create a valley that surrounds the user's nose (as shown in FIG. 12). The left and right upper cushion supports 310A, 310B are illustrated as having a rounded semicircular shape. However, the left and right upper cushion supports 310A, 310B may have a size and shape that corresponds with the shape of the left and right upper cushion ridges 516A, 516B, as will be discussed in further detail below.

The gases aperture 304 is adapted to receive an elbow component 1100 (see FIG. 2F, or FIG. 8F for an exemplary elbow component 1100) configured to interface with a gases delivery conduit (for example, the gases conduit 112 described elsewhere in this disclosure with reference to FIG. 1). The elbow component 1100 may be adapted to swivel or rotate relative to the frame 300 (through, for example, a ball-joint connection or arrangement). The elbow component 1100 comprises an elbow outlet portion 1102. The elbow outlet portion 1102 interfaces with the frame 300 via the gases aperture 304. Downstream of the outlet portion 1102 of the elbow component 1100 (relative to an exhalation flow direction) lays a venting area 1104. The venting area 1104 comprises vent holes that permit a leak flow to escape the patient interface 200. The vent holes can help to mitigate the build-up of carbon dioxide in the patient interface 200 and/or gases delivery conduit. In the illustrated configurations, the vent holes are cut into the surface of the elbow component 1100 using a laser. In other configurations, the vent holes 1104 could be formed during molding and/or processing of the elbow component 1100, or formed by cutting portions out of a wall of the elbow component 1100 (e.g. with a blade). In some configurations, the vent holes could be covered by media adapted to diffuse sound generated by flow passing through the vent holes. In some configurations the vent holes could be covered by media adapted to diffuse flow passing through the vent holes by scattering or distributing the flow in a number of directions. In some configurations, slots, gaps, or other apertures could be used instead of or together with the vent holes. In some configurations, other portions of the patient interface 200, including but not limited to the portions of the patient interface 200 forming the ball-joint connection, the frame, the gases delivery conduit, and other portions of the patient interface 200 through which gases pass could comprise venting areas. The elbow component 1100 additionally comprises an anti-asphyxia valve assembly 1106 adapted to prevent excessive accumulation of exhaled carbon dioxide in the patient interface 200 and/or gases delivery conduit (e.g. when gases are not being delivered to the user through the elbow component 1100). The anti-asphyxia valve assembly 1106 may, for example, be the same or similar to the anti-asphyxia valve assembly disclosed in commonly-owned US 2014/0096774, which is hereby incorporated by reference in its entirety. A tube section 1108 extends from the body of the elbow component 1100. The tube section 1108 may be configured to be rotatable relative to the frame 300. The tube section 1108 may be removable to allow for cleaning and/or replacement. In other configurations, the tube section 1108 may be permanently fixed to the frame 300. Gases can be introduced to the frame 300 through the elbow component 1100 using an elbow inlet portion 1110 defined by the tube section 1108. In some configurations, the tube section 1108 may not be present, and a gases delivery conduit may interface directly with the body of the elbow component 1100.

Headgear 450 (see FIGS. 2F and 2G) interfaces with the frame 300. The headgear retains the patient interface 200 on the head of the user. The headgear 450 may be constructed from a variety of materials, including but not limited to fabrics, foams, fabric/foam composites and Breath-O-Prene™. The headgear 450 is substantially symmetrical. A four-point connection between the headgear 450 and the frame 300 is made available using the upper connection slots 306A, 306B (through headgear connection elements 400A, 400B further described elsewhere in this disclosure) and the lower connection slots 308A, 308B present on the frame 300. In an exemplary embodiment, the headgear 450 comprises left and right top straps 458A, 458B and left and right bottom straps 452A, 452B. The bottom straps 452A, 452B generally extend along the sides and towards the back of the head under the ears (for example and not limited to, extending over the sternocleidomastoid, platysma, risorius and/or buccinator). The top straps 458A, 458B generally extend along the sides and towards the back of the head over the ears (for example and not limited to, extending over the aricularis anterior, auricularis superior, and/or temporal fascia). As shown the top straps 458A, 458B are secured using the top strap ends 460A, 460B, which comprise hook pads or patches that can be secured to complementary loop surfaces on the top straps 458A, 458B (e.g. in a hook-in-loop style fastening mechanism). The left and right bottom straps 452A, 452B are integrally formed or in the form of a single piece together with a back panel 462 adapted to rest over the back of the head (for example and not limited to, resting over the occiput and/or trapezius). It should be understood that the locations of the straps relative to the anatomical regions of the user's head is only exemplary and not limiting. In other configurations the bottom straps 452A, 452B and back panel 462 could be integrally formed or in the form of a single continuous piece. The back panel 462 is joined to a crown strap portion 464 at a joint $J_1$. The crown strap portion 464 is divided into left and right crown straps 464A, 464B that are joined at a joint $J_2$. In the illustrated configuration, the joints $J_1$, $J_2$ are formed by stitching portions of the headgear 450 together. In other configurations, the joints $J_1$, $J_2$ may be formed using other means, including but not limited to general overlap or butt welding techniques, ultrasonic welding, high frequency welding, adhesives, and other mechanical fastening arrangements. In some configurations, all components of the headgear 450 could be integrally formed or in the form of a single continuous piece.

The left and right crown straps 464A, 464B generally extend from the joint $J_1$ upwardly along the head behind the ears (for example and not limited to, extending over the sternocleidomastoid, aricularis posterior, aricularis superior, and/or temporalis). Above the ears, the left and right top straps 458A, 458B extend outwardly from the left and right crown straps 464A, 464B. The left and right top straps 458A, 458B extend in a direction that is substantially lateral to the direction in which the left and right crown straps 464A, 464B extend upwardly along the head. In other configurations, the left and right top straps 458A, 458B may be physically disparate from the left and right crown straps 464A, 464B. The left and right top straps 458A, 458B may be joined to the left and right crown straps 464A, 464B in some other manner (for example, in a manner similar to the joints $J_1$, $J_2$). The left and right crown straps 464A, 464B meet at the top of the head (for example and not limited to, meeting over the parietal). To adjust the fit of the headgear 450 on the head, the crown strap ends 466A, 466B of the crown straps 464A, 464B are passed through a headgear retainer 468 (e.g. a buckle comprising apertures configured to accept the crown straps 464A, 464B). The crown straps 464A, 464B are then looped back upon themselves and secured. As shown the crown straps 464A, 464B are secured using the crown strap ends 466A, 466B, which comprise hook pads or patches that can be secured to complementary loop surfaces on the crown straps 464A, 464B (e.g. in a hook-in-loop style fastening mechanism). The loop surfaces may be added by placing adhesive loop pads on the surfaces of the crown straps 464A, 464B. In other configurations, the loop surfaces may be inherent in the material used for the crown straps 464A, 464B. Alternatively, if all the components of the headgear 450 are integrally formed or come as a single continuous piece, the crown straps 464A, 464B may be permanently fixed together. In some such configurations the crown straps 464A, 464B (being in the form of a single piece) may be made more flexible or elastic than other components of the headgear 450 to promote an adjustable headgear 450 fit. Similarly, the left and right top straps are secured using headgear retainers 408A, 408B located on the headgear connection elements 400A, 400B (see FIGS. 3A and 3B). The left and right bottom straps 452A, 452B are secured to the frame 300 using hooks 456A, 456B configured to engage with the edges of the frame 300 defined by the left and right lower connection slots 308A, 308B. The hooks 456A, 456B comprise slots through which the left and right bottom straps 452A, 452B can be threaded and looped upon themselves using hooked sections 454 that mate with complementary looped sections of the left and right bottom straps 452A, 452B (in a hook-and-loop style connection mechanism). Other ways of securing the left and right bottom straps 452A, 452B may be used, including but not limited to resealable adhesives and other mechanical fastener arrangements.

The illustrated headgear 450 and interaction between the headgear 450 and the frame 300 should not be taken to be limiting, and certain features, aspects and advantages of other headgear elements or systems may be equally applied to the patient interface configurations disclosed. For example, certain features, aspects and advantages of the headgear elements or systems disclosed in commonly owned PCT/NZ2014/000075, which is hereby incorporated by reference in its entirety and included by appendix, may replace or be incorporated into certain features, aspects and advantages of the illustrated headgear 450.

Figure 5A:
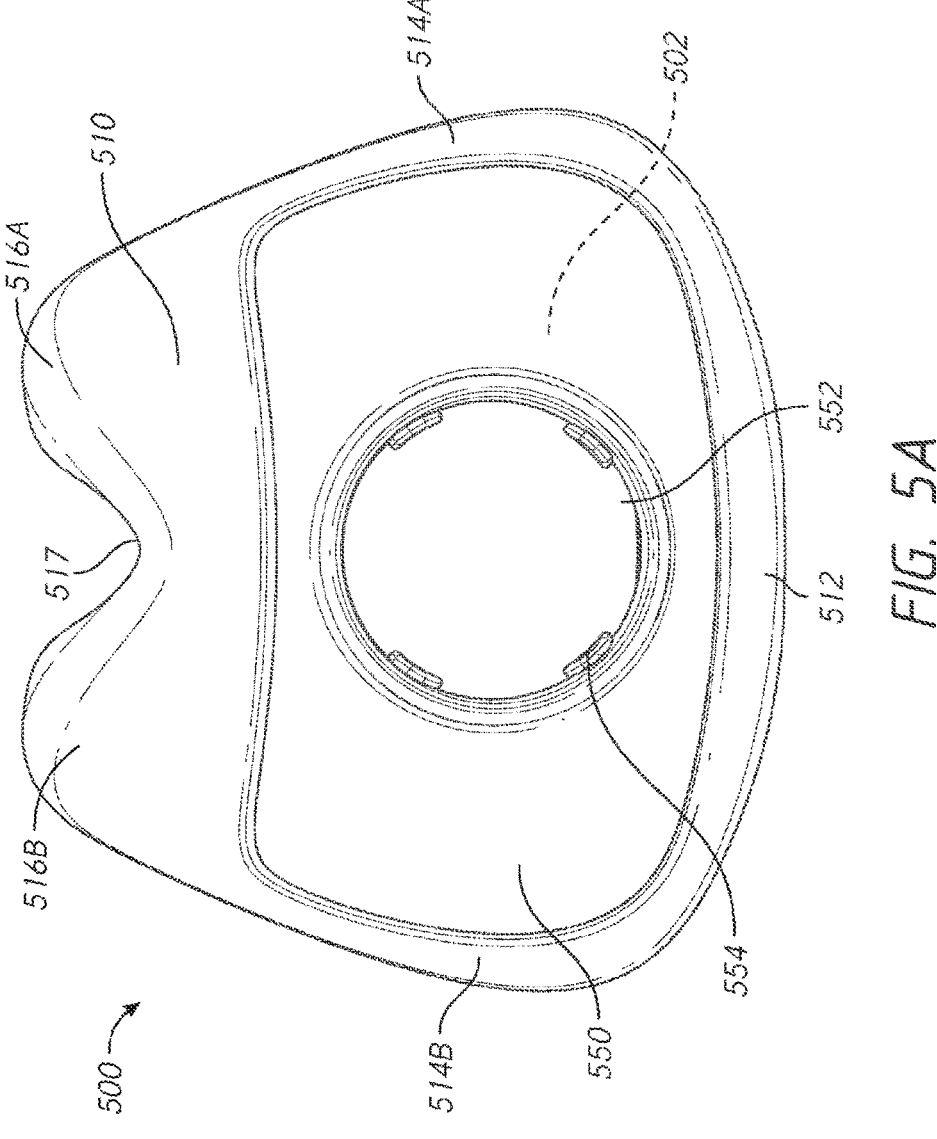
FIG. 5A shows a front plan view of a cushion module.
Figure 5B:
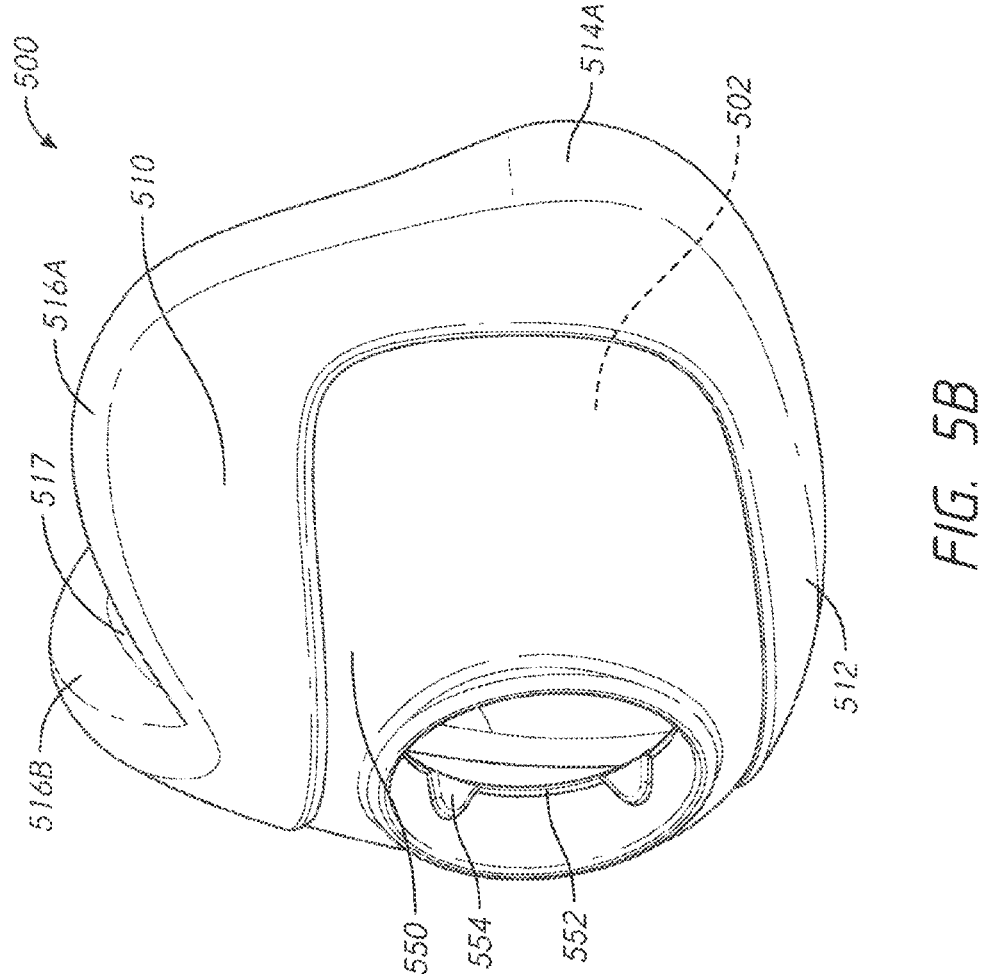
FIG. 5B shows a side front view of the cushion module of FIG. 5B.
Figure 5C:
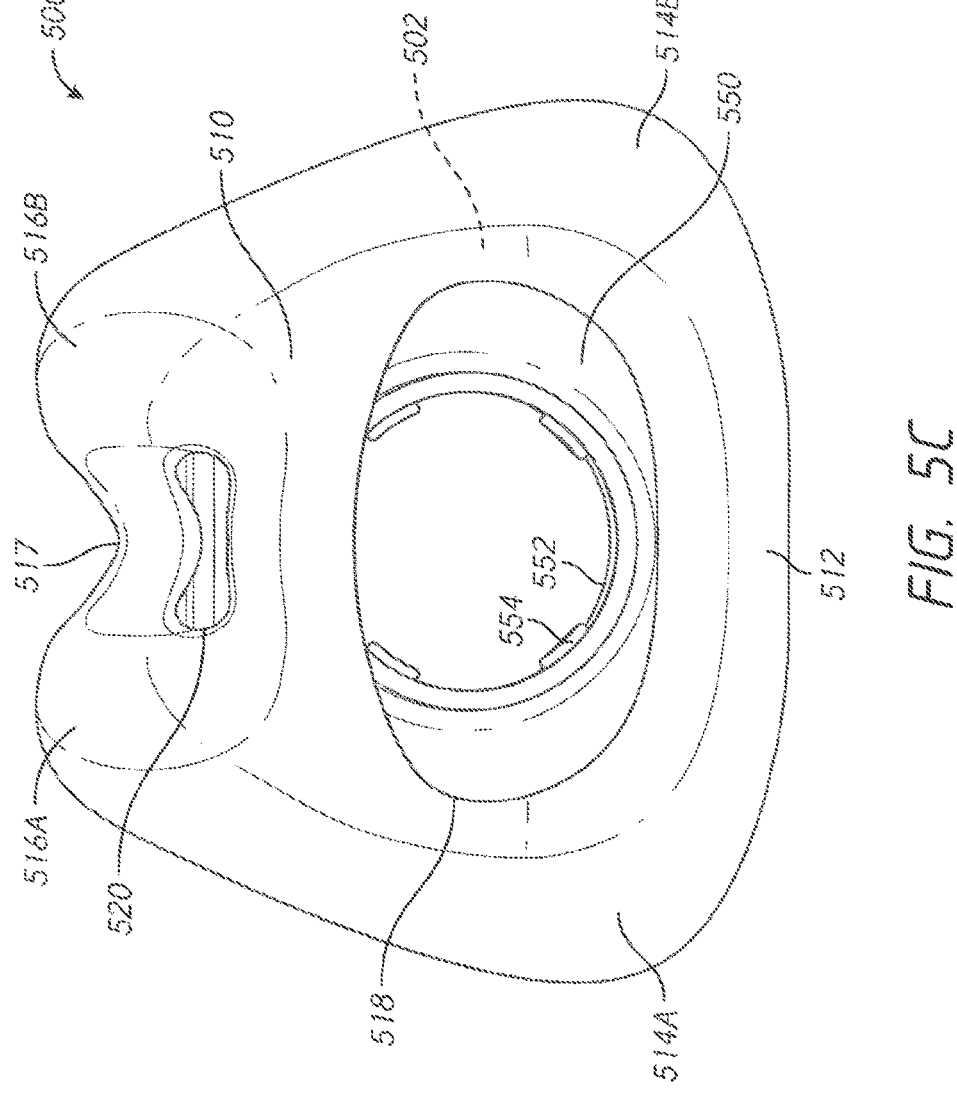
FIG. 5C shows a rear plan view of the cushion module of FIG. 5C.
Figure 6A:
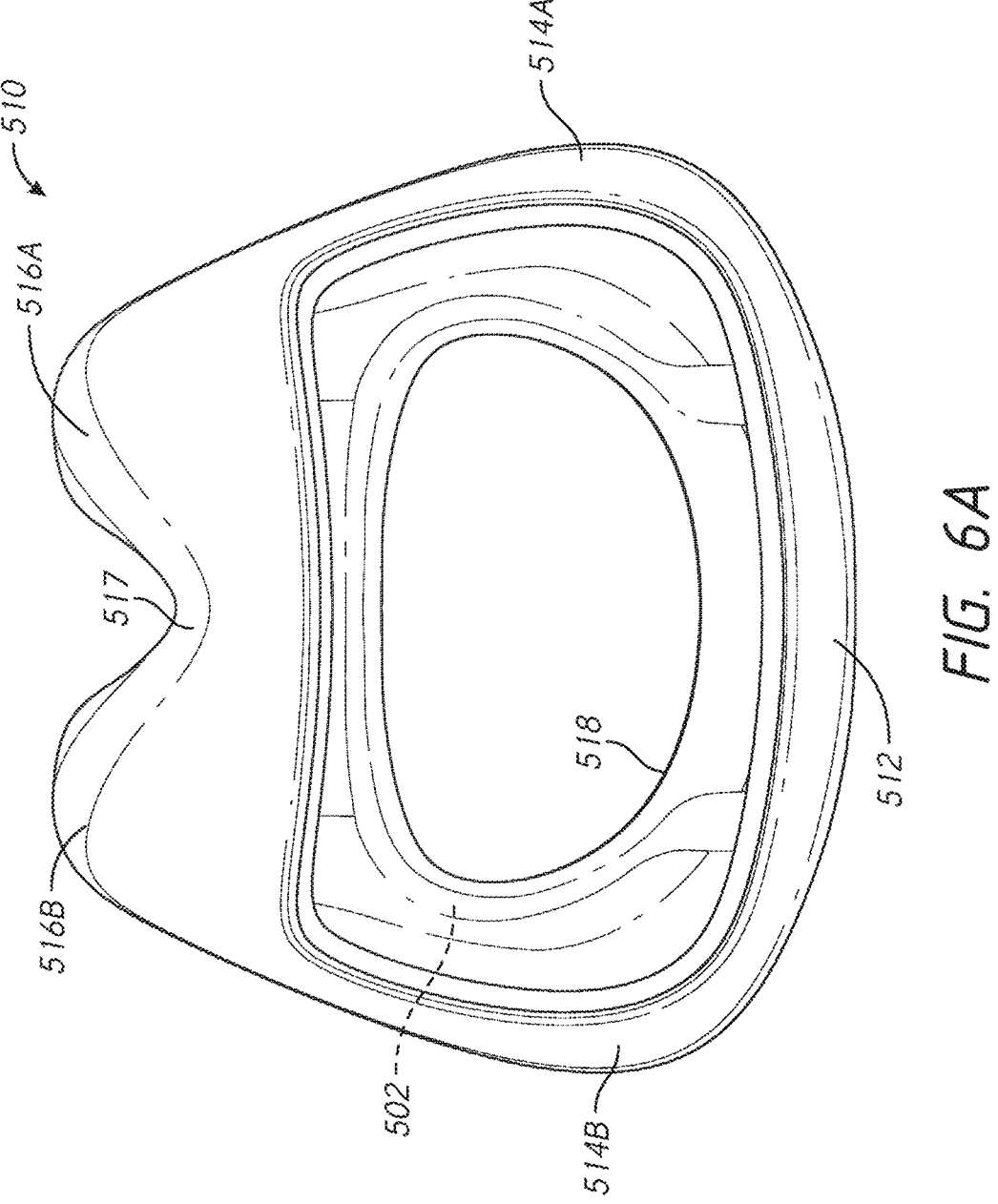
FIG. 6A shows a front plan view of a cushion.
Figure 6B:
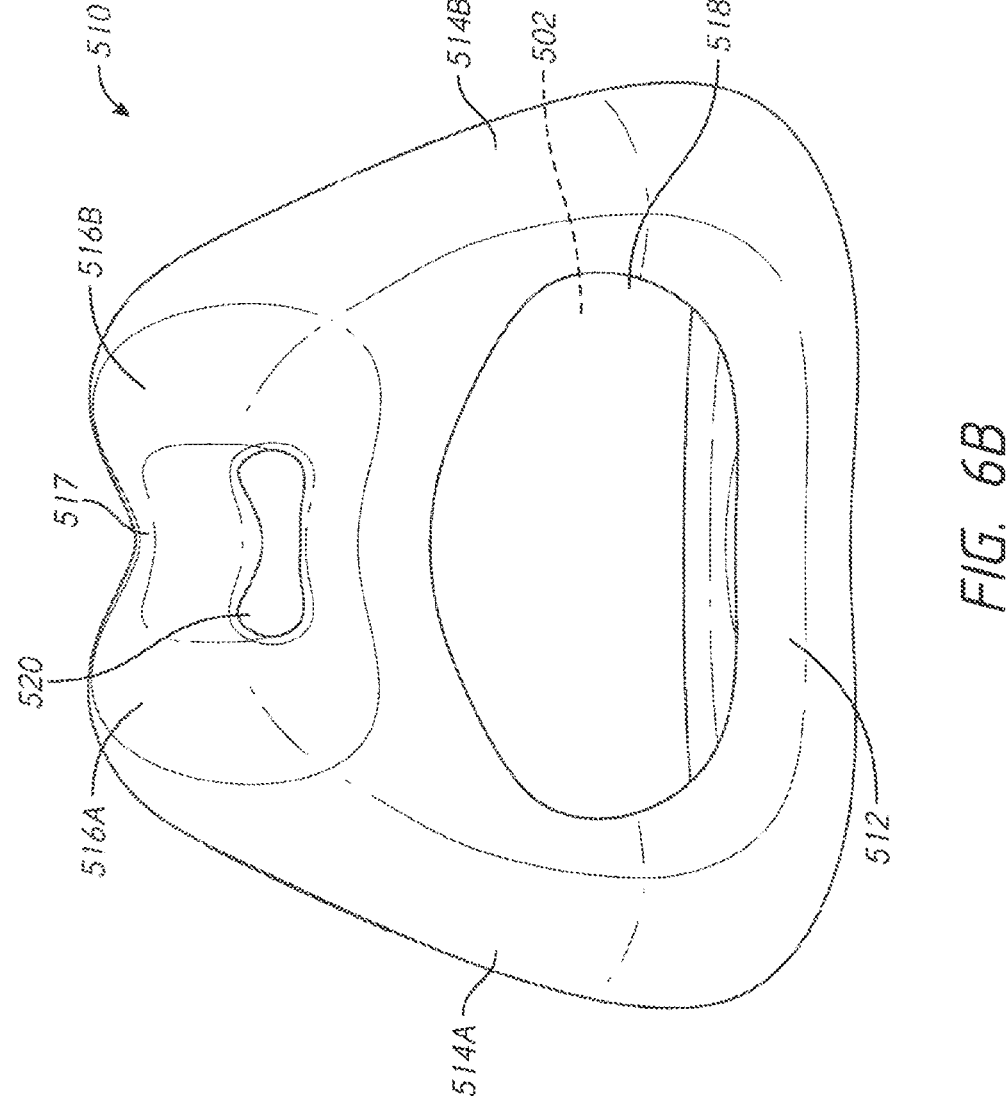
FIG. 6B shows a rear plan view of the cushion of FIG. 6A.

As shown in FIGS. 2A-2F, the frame 300 engages with a cushion module 500 (see FIGS. 5A-5C). The cushion module may be the same or similar to the cushion modules disclosed in commonly owned U.S. 62/013,445, which is hereby incorporated by reference in its entirety and included by appendix. The cushion module 500 comprises a pliable seal or cushion member 510 (constructed from, for example, silicone or other plastics, foam, fabrics, textiles, or other materials; see FIGS. 6A-6B) configured to engage with the user's face. The cushion member 510 comprises a nasal recess 517 defined by left and right upper cushion ridges 516A, 516B. In use, the left and right upper cushion ridges 516A, 516B are supported by the left and right upper cushion supports 310A, 310B of the frame 300. In other words, the size, shape and geometry of the left and right upper cushion supports 310A, 310B may correspond with the left and right upper cushion ridges 516A, 516B such that the left and right upper cushion ridges 516A, 516B are supported by the left and right upper cushion supports 310A, 310B. More specifically, the left and right upper cushion ridges 516A, 516B may provide an inwardly-directed ballooning effect to provide an enhanced seal against an outer surface of the nose. As such, the left and right upper cushion supports 310A, 310B may provide a rigid backing from which force may be directed toward the user's nose by the left and right upper cushion ridges 516A, 516B. Similarly, the left and right upper cushion supports 310A, 310B may limit, inhibit or prevent an undesirable amount of expansion or outward movement of the left and right upper cushion ridges 516A, 516B. Too much expansion may be uncomfortable to the user, such as by causing the nasal region to press against the underside of the user's nose, and/or compromise the seal between the face of the user and the cushion member 510. Thus, characteristics (e.g., size, shape or location) of the left and right upper cushion supports 310A, 310B can be selected to provide a desired level of support and/or allow a desired level of expansion of the left and right upper cushion ridges 516A, 516B or other portions of the cushion member 510. Preferably, the left and right upper cushion supports 310A, 310B may cover at least 50% of the left and right upper cushion ridges 516A, 516B. A nasal gases passageway 520 is positioned under the nasal recess 517. The nasal gases passageway 520, nasal recess 517, and left and right upper cushion ridges 516A, 516B are configured such that an under-the-nose seal (for example, a seal over the nasal ala, apex, nasolabial fold, subnasale and/or philtrum) is attained. The cushion member 510 additionally comprises an opening 518 bounded by left and right side portions 514A, 514B and by a bottom portion 512. The opening 518, the left and right side portions 514A, 514B and the bottom portion 512 are configured such that an around-the-mouth seal (for example, a seal over the lip superior, lip inferior, supramenton and/or mental protuberance) is attained. In some configurations, to improve user comfort or to change the sealing characteristics of the cushion member 510, the thickness of the cushion member 510 may be variable along its body. For example, the cushion member 510 may be thinner along portions of the cushion member 510 proximal to the nasal gases passageway 520 (e.g. at the nasal recess 517, sides of the left and right upper cushion ridges 516A, 516B facing the nasal recess 517 and/or along portions of the cushion member 510 defining the nasal gases passageway 520) and/or portions of the cushion member 510 proximal to the opening 518 (e.g. at upper parts of the bottom portion 512 and/or along other portions of the cushion member 510 defining the nasal gases passageway 520). In other configurations, the oral and nasal portions of the cushion member 510 may be physically disparate or separate. Further, the oral and nasal portions of the cushion member 510 may be separate components or a common assembly.

Figure 7A:
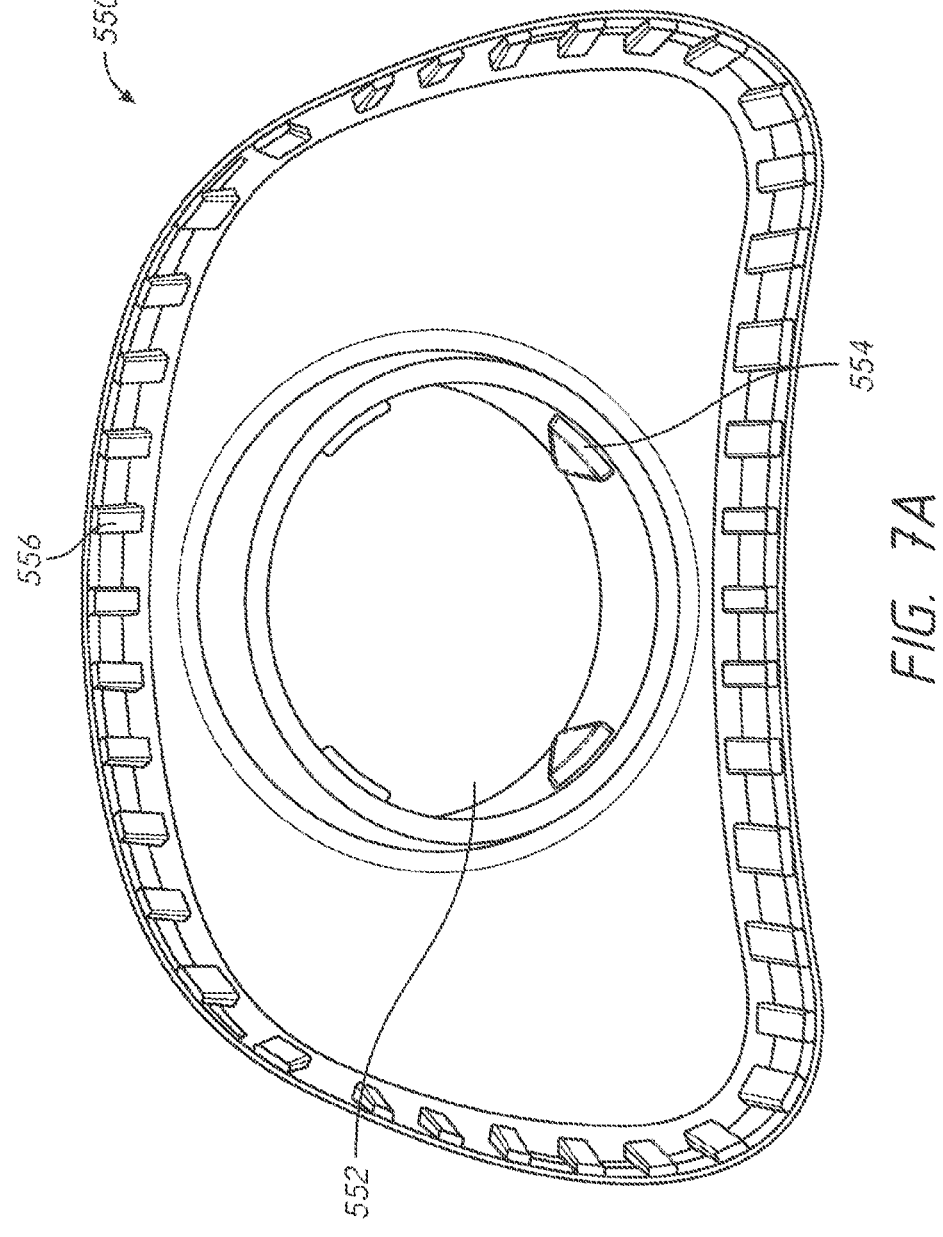
FIG. 7A shows a rear plan view of a cushion support member.
Figure 7B:
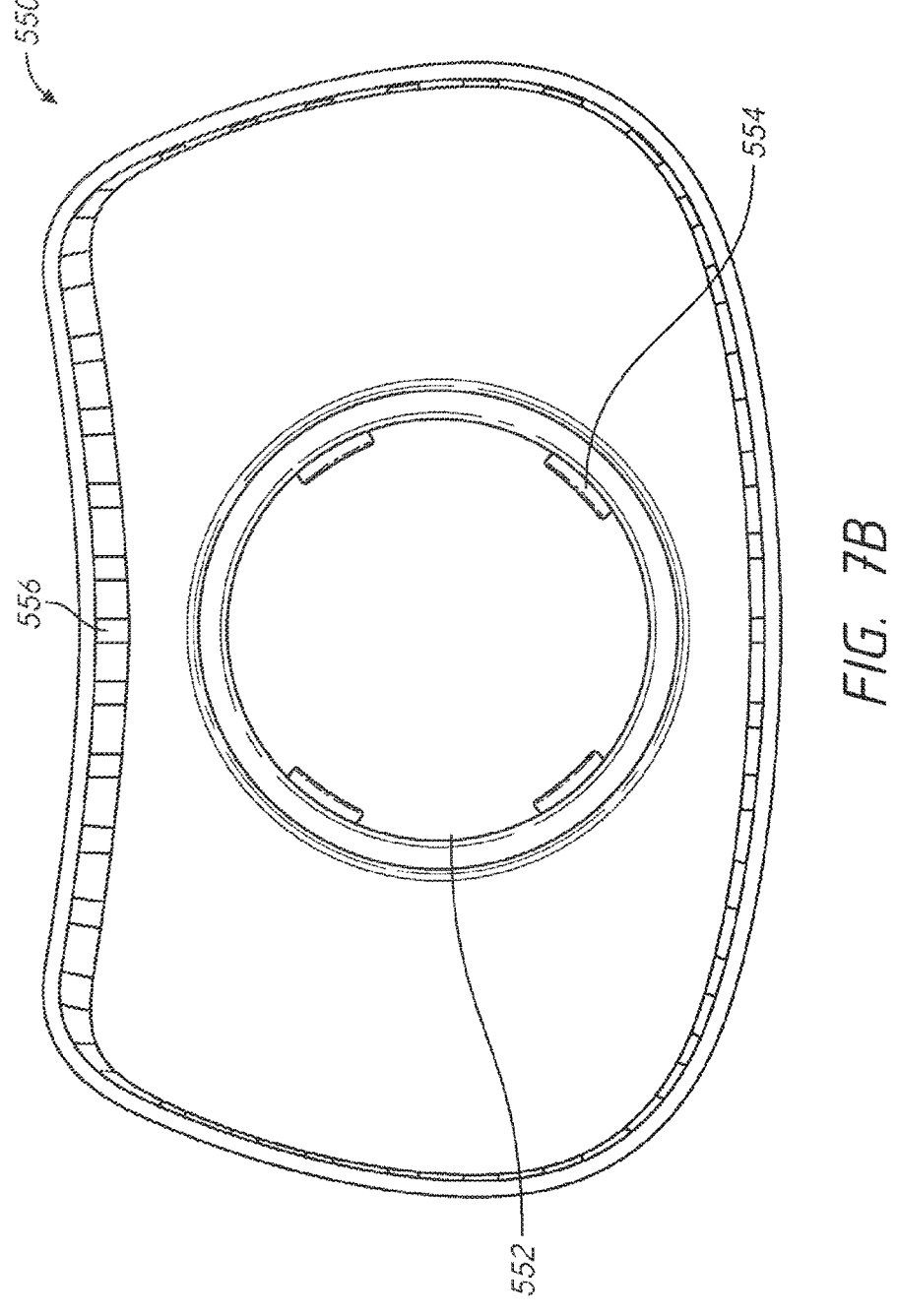
FIG. 7B shows a front plan view of the cushion support member of FIG. 7A.
Figure 7C:
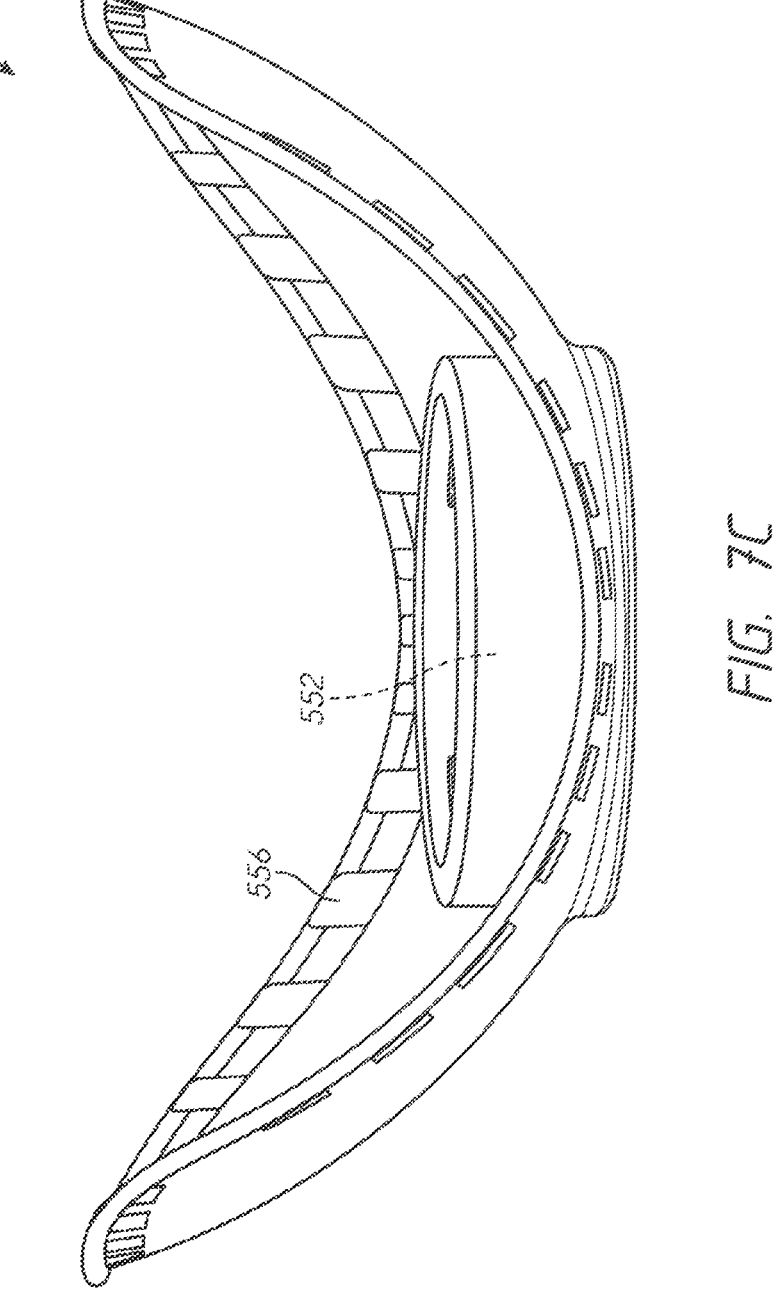
FIG. 7C shows a top plan view of the cushion support member of FIG. 7A.

The cushion module 500 additionally comprises a cushion brace or shell 550 (see FIGS. 7A-7C). The cushion brace or shell 550 is relatively more rigid than the cushion member

510 and is adapted to help reinforce and maintain the shape of the cushion member 510 when the cushion module 500 is linked to the frame 300. The cushion brace or shell 550 is integral with or in the form of a single piece with the cushion member 510. In the illustrated configuration, the cushion brace or shell 550 and the cushion member 510 are co-moulded or overmoulded together along with, for example, the perforated fringe 556 of the cushion brace or shell 550. The perforated fringe 556 is located along the perimeter of the cushion brace or shell 550 and includes a series of perforations or projections that provide overmould locations for the cushion member 510 to be overmoulded onto the cushion brace or shell 550. In other configurations, the cushion brace or shell 550 and the cushion member 510 may be joined by other means, including but not limited to ultrasonic or high frequency welding, adhesives, and/or latch/catch arrangements. The cushion brace or shell 550 comprises a brace aperture 552 that is substantially in alignment with the gases aperture 304 of the frame 300. Pneumatic communication between a gases chamber or plenum chamber 502 (defined by the cushion member 510 and the cushion brace or shell 550) and the gases delivery conduit described elsewhere in this disclosure (for example, with reference to FIG. 1 as described above) is established at least in part using the connection between the brace aperture 552 of the cushion brace or shell 550 and the gases aperture 304 of the frame 300. As shown in FIG. 2C, the frame 300 may be inserted into the cushion member 510 such that the frame 300 and the cushion member 510 are mechanically interlocked together through the use of the cushion module retention portion of the frame 300 (described elsewhere with reference to the raised 312 and depressed 314 portions of the wall of the frame 300 and to FIGS. 4A-4D) and a frame retention portion 554 of the cushion brace or shell 550 (defined by raised portions of the wall of the cushion brace or shell 550 defining the brace aperture 552). The outer wall of the frame that defines the gases aperture 304 and the inner wall of the cushion member 510 that defines the brace aperture 552 may be removably connected by a snap-fit, interference fit, interlocking arrangement, etc. to mechanically interlock the frame 300 with the cushion member 510. Allowing the cushion member 510 to be separated and removed from the frame 300 allows both the cushion member 510 and the frame 300 to be easily cleaned.

As mentioned, in the illustrated configuration it is desirable that the cushion member 510 be urged against the face with sufficient force such that effective under-the-nose and around-the-mouth sealing is achieved without putting undue pressure on the nose or mouth. The force exerted on the cushion module 500 by the headgear 450 (e.g. transferred through the frame 300) can be an important determinant of the force exerted by the cushion member 510 on the face. It can be important, then, to study the forces exerted to maximize the comfort of the user while maintaining the efficacy of the gases therapy delivered to the user.

FIG. 12 illustrates forces applied to an alternative embodiment of a patient interface having a frame Fr and headgear H. The headgear H interfaces with the frame Fr via a four-point connection through bottom straps $S_1$ and top straps $S_2$ (left side shown only). As shown, in use the bottom straps $S_1$ exert a force $F_1$ on the frame Fr, which comprises a relatively large horizontal force vector $F_{1\_x}$ and a relatively small vertical force vector $F_{1\_y}$. The top straps $S_2$ in use exert a force $F_2$ on the frame Fr, which comprises both a significant horizontal force vector $F_{2\_x}$ and a significant vertical force vector $F_{2\_y}$. The vertical force vector $F_{2\_y}$ of the force $F_2$ seals the cushion member against the nose. In some cases, with this four-point connection or with similar connections, the significant vertical force vector $F_{2\_y}$ can cause discomfort for the user due to the perception of an excessive pressure under the nose (for example, over the lip superior, subnasale and/or columella). In some cases it is then desired to decrease the vertical forces exerted by the straps of headgear used (e.g. by the top or upper straps used).

With reference to FIGS. 2A-2G and FIGS. 3A-3C, attention is given towards an alternative embodiment that includes the headgear connection elements 400A, 400B. In the illustrated exemplary non-limiting configurations, the headgear connection elements 400A, 400B are symmetrical, and so the disclosure will be focused upon the left headgear connection element 400A. However, in other configurations, the headgear connection elements 400A, 400B could have different shapes or characteristics. Dissimilar headgear connection elements 400A, 400B could be useful dependent on the shape or dissymmetry of the user's head.

Figures 3A, 3B, 3C:
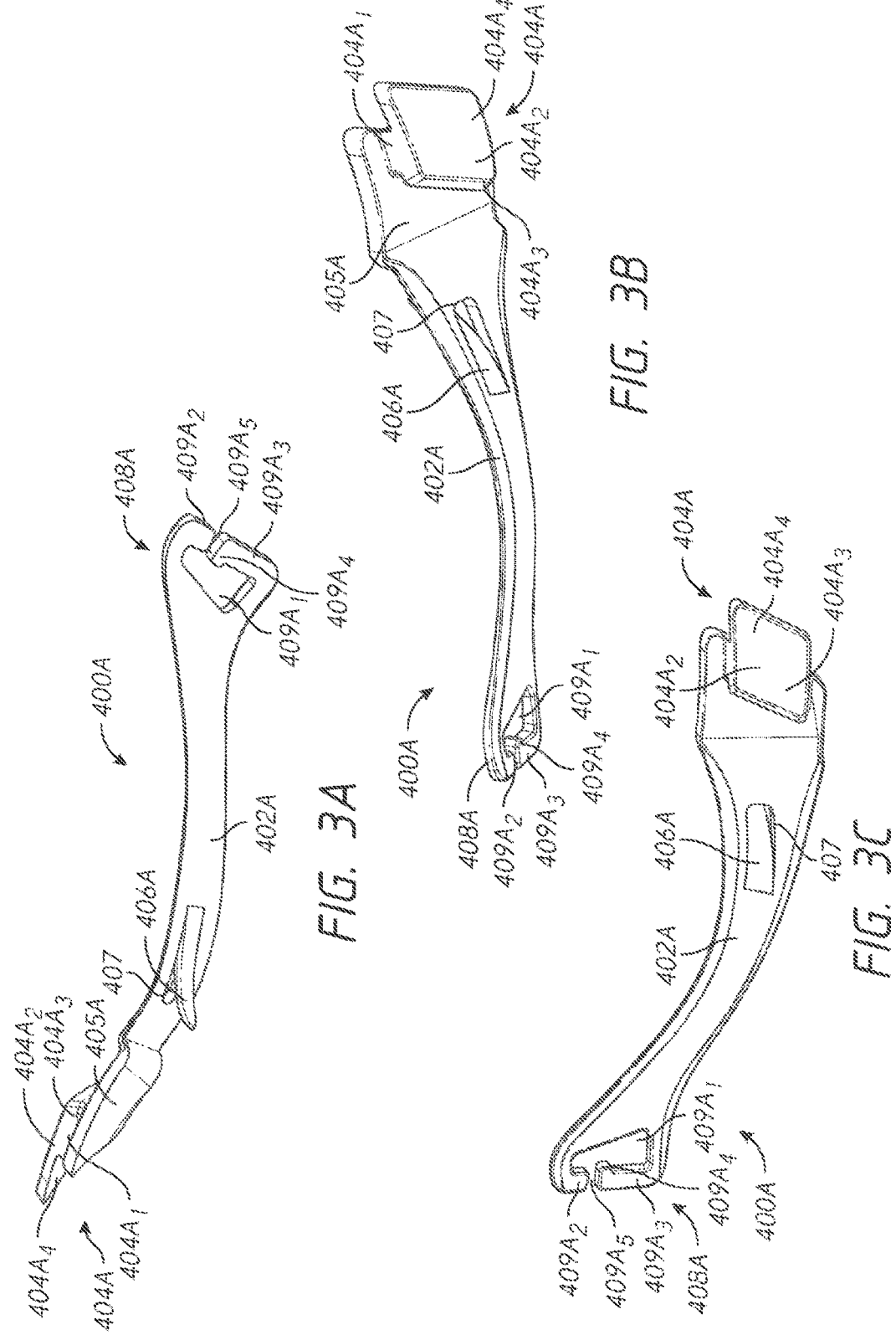
FIG. 3A shows a rear perspective view of a headgear connection element.
FIG. 3B shows a front perspective view of the headgear connection element of FIG. 3A.
FIG. 3C shows a front view of the headgear connection element of FIG. 3A.
Figure 4A:
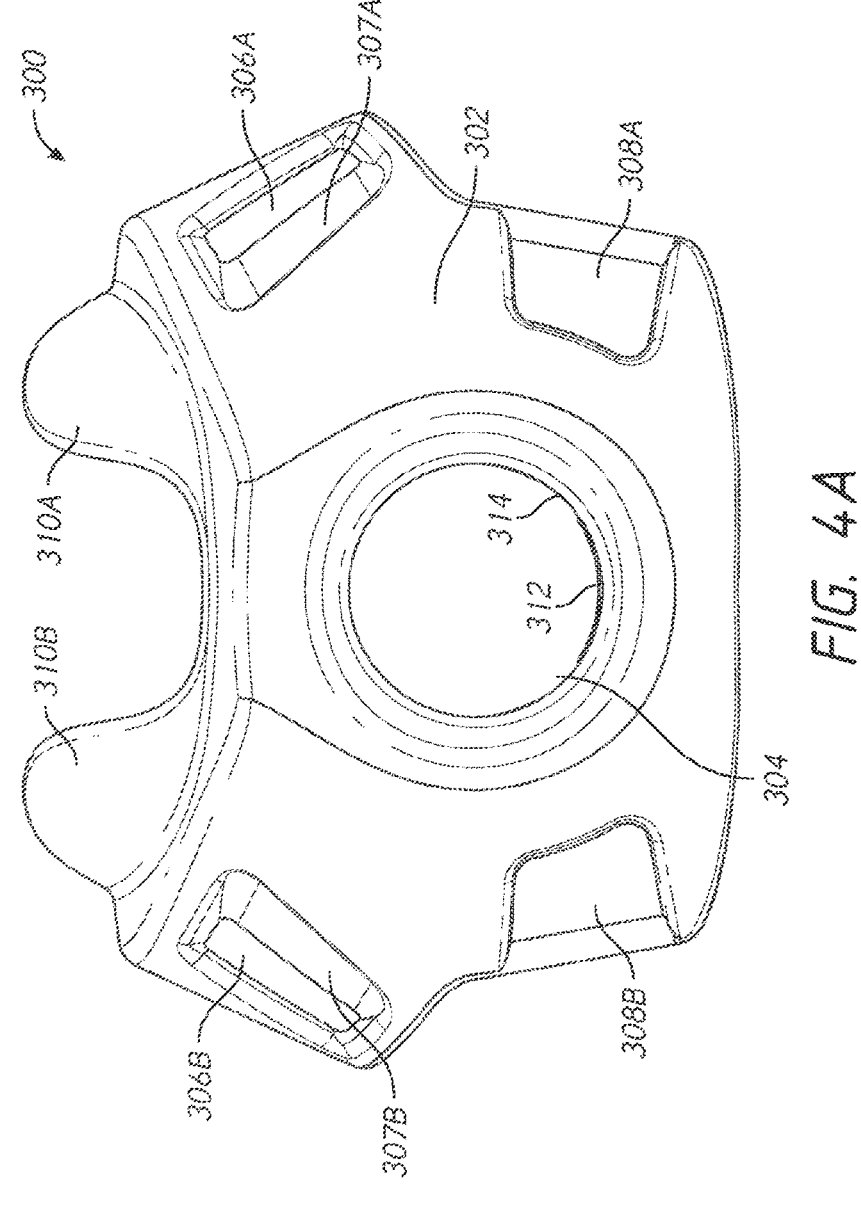
FIG. 4A shows a front plan view of a frame of a patient interface.
Figure 4B:
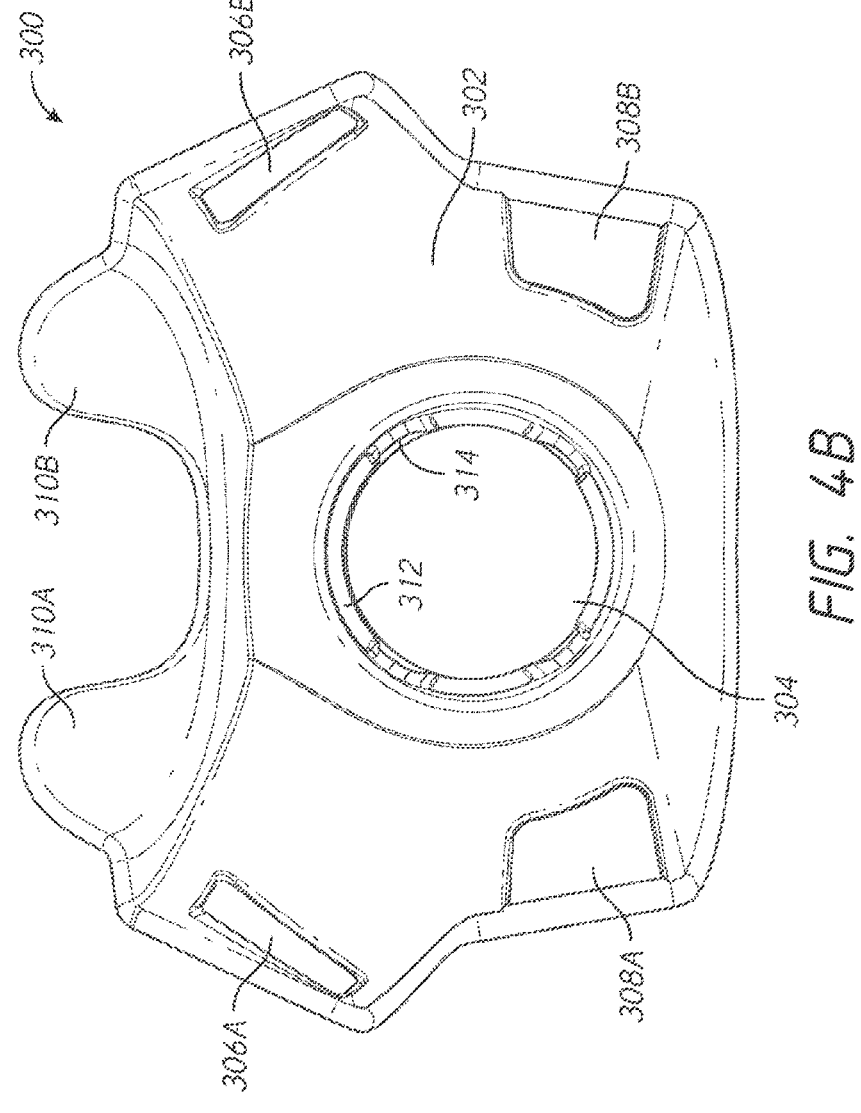
FIG. 4B shows a rear plan view of the frame of FIG. 4A.
Figure 4C:
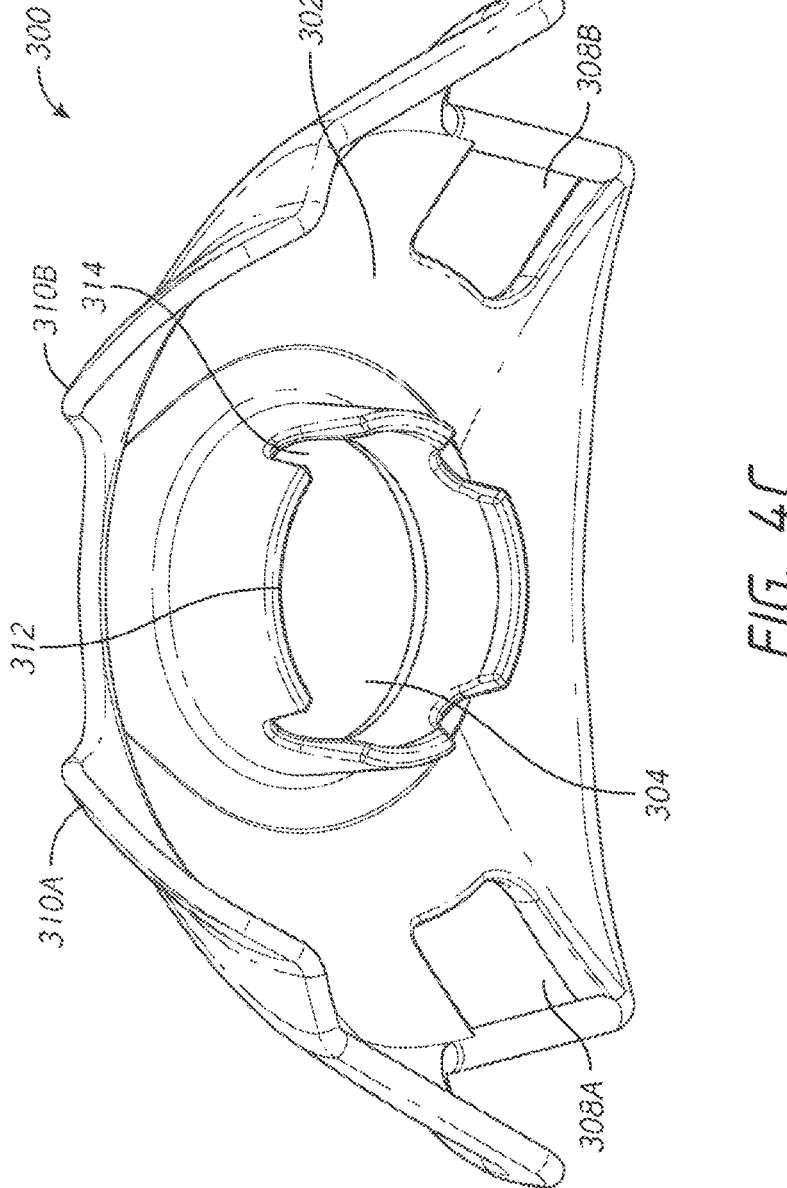
FIG. 4C shows an elevated rear view of the frame of FIG. 4A.
Figure 4D:
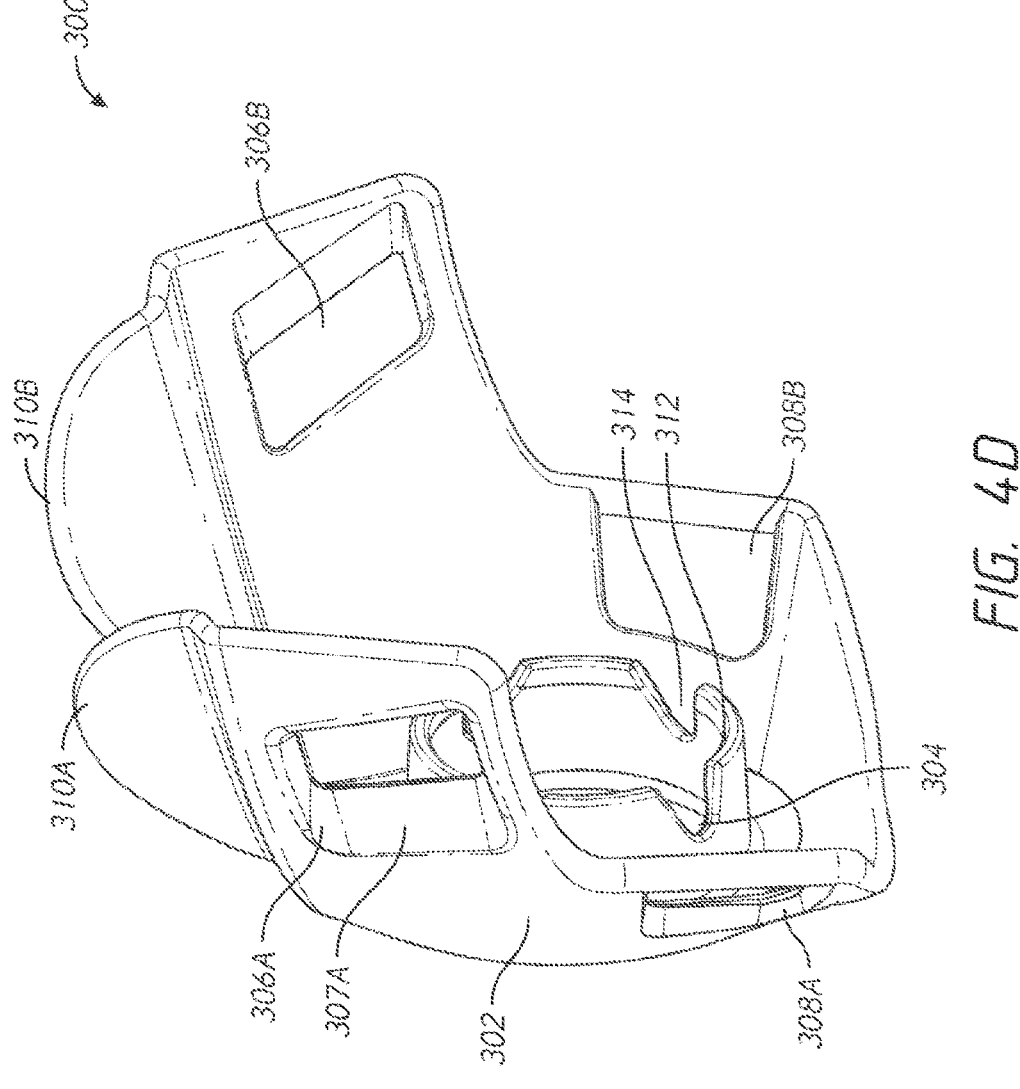
FIG. 4D shows a side rear view of the frame of FIG. 4A.

As shown in FIGS. 3A-3C, the headgear connection element 400A comprises a substantially rigid side wing or body 402A. The body 402A extends between a first end defined by the headgear retainer 408A (previously mentioned elsewhere in this disclosure) and a second end defined by a frame connection element 404A adapted to interface with the frame 300. The body 402A is substantially arcuate, having a curved shape (curved along the page as shown in FIGS. 3A-3C) that at first extends substantially horizontally from the second end and then substantially upwardly and horizontally along the face (for example, over the cheeks) from about halfway along the body 402A to the first end.

The headgear retainer 408A is defined by a slot $409A_1$. The slot $409A_1$ is positioned between the body 402A and a pair of retainer legs $409A_2$, $409A_3$. In the illustrated configuration, the lower retainer leg $409A_3$ is longer than the upper retainer leg $409A_2$. A lateral extension $409A_4$ protrudes from an inside surface of the lower retainer leg $409A_3$. A looped headgear strap (for example, the left top strap 458A described with reference to FIGS. 2F and 2G) can be inserted through a retainer gap $409A_5$ and the bulk of the looped strap can be held around the lower retainer leg $409A_3$. The lateral extension $409A_4$ resists tendencies for the retained looped strap to move up the lower retainer leg $409A_3$ and out the retainer gap $409A_5$ by acting as an obstruction or baffle. In other configurations, portions of the headgear retainer 408A defining the retainer gap $409A_5$ and/or slot $409A_1$ can be overmoulded or otherwise comprise a surface having a high coefficient of friction adapted to prevent vertical movement of headgear straps retained by the headgear retainer 408A.

Further attention is given to the frame connection element 404A. Towards the second end from about the middle, the body 402A of the headgear retainer 408A arcs downwardly (curving into the page in FIG. 3C) into a relatively flat depressed section 405A. The end of the depressed section 405A distal from the middle of the body 402A comprises a projection $404A_1$ extending outwardly from the depressed section 405A in a direction substantially transverse to the direction in which the depressed section 405A extends. In the illustrated configuration the projection $404A_1$ is substantially rigid. The upper end $404A_2$ of the projection $404A_1$ has a first section $404A_3$ extending back towards the body 402A of the headgear retainer 408A (e.g. towards the middle of the body 402A). The upper end $404A_2$ also includes a second section $404A_4$ extending away from the body 402A of the headgear 408A (e.g. away from the middle of the body 402A) in a direction substantially parallel to the direction in which the depressed section 405A extends. The upper end $404A_2$ is wider than the base of the projection $404A_1$, imparting the appearance of a mushroom-like projection $404A_1$. Alternatively stated, the upper end $404A_2$ has a larger cross-sectional area than the base of the projection $404A_1$.

To fit the exemplary non-limiting frame connection element 404A to the frame 300, the second section $404A_4$ of the projection $404A_1$ is forced through the left upper connection slot 306A of the frame 300 (see FIGS. 2A-2B, 4A-4D) such that the second section $404A_4$ rests in a recess 307A proximal to a surface of the frame 300 defining the left upper connection slot 306A. In other words, a portion of a wall of the frame 300 that defines the left upper connection slot 306A includes a recess 307A. The recess 307A is adapted to hold the second section $404A_4$ of the headgear connection element 400A. The recess 307A extends and is skewed towards a middle of the frame 300, as illustrated in FIG. 2B. The skewed angle of the recess may correspond to the angle of the force on the frame 300 by the straps with respect to horizontal. When the second section of the projection $404A_1$ is correctly positioned, the first section $404A_3$ rests against another surface of the frame 300 defining the left upper connection slot 306A, the other surface of the frame 300 being opposite to the direction in which the recess 307A extends. The edge of the other surface of the frame 300 rests in the depressed section 405A. In other configurations, the headgear connection element 400A may be integrally formed or be in the form of a single continuous piece with the frame 300. In still other configurations, the headgear connection element 400A may be fixed to the frame 300 by other means, including but not limited to overmoulding, co-moulding, adhesives, ultrasonic welding, high-frequency welding, and the use of other mechanical fastening or interlocking arrangements. In further configurations, the headgear connection element 400A may be flexibly connected to the frame 300. Alternatively, the headgear connection element 400A may be rigidly connected to the frame 300 such that force transfer between the headgear and the user's nose is improved.

Figure 2F:
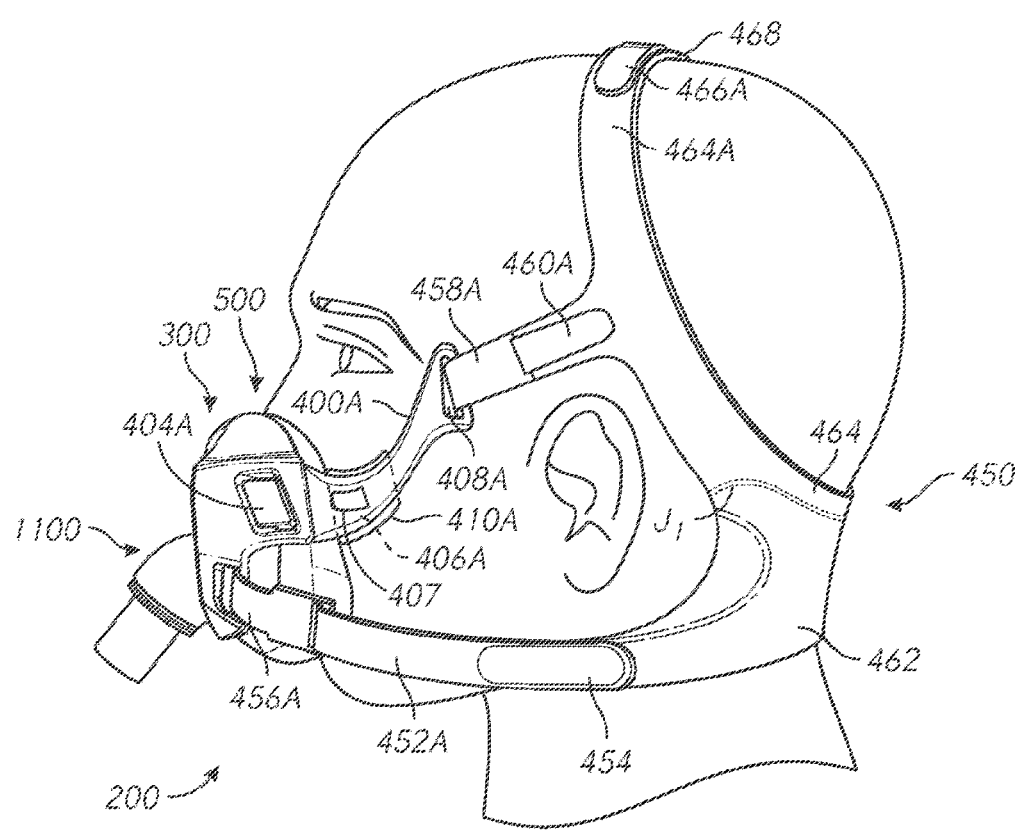
FIG. 2F shows a side plan view of the patient interface of FIG. 2A.
Figure 2G:
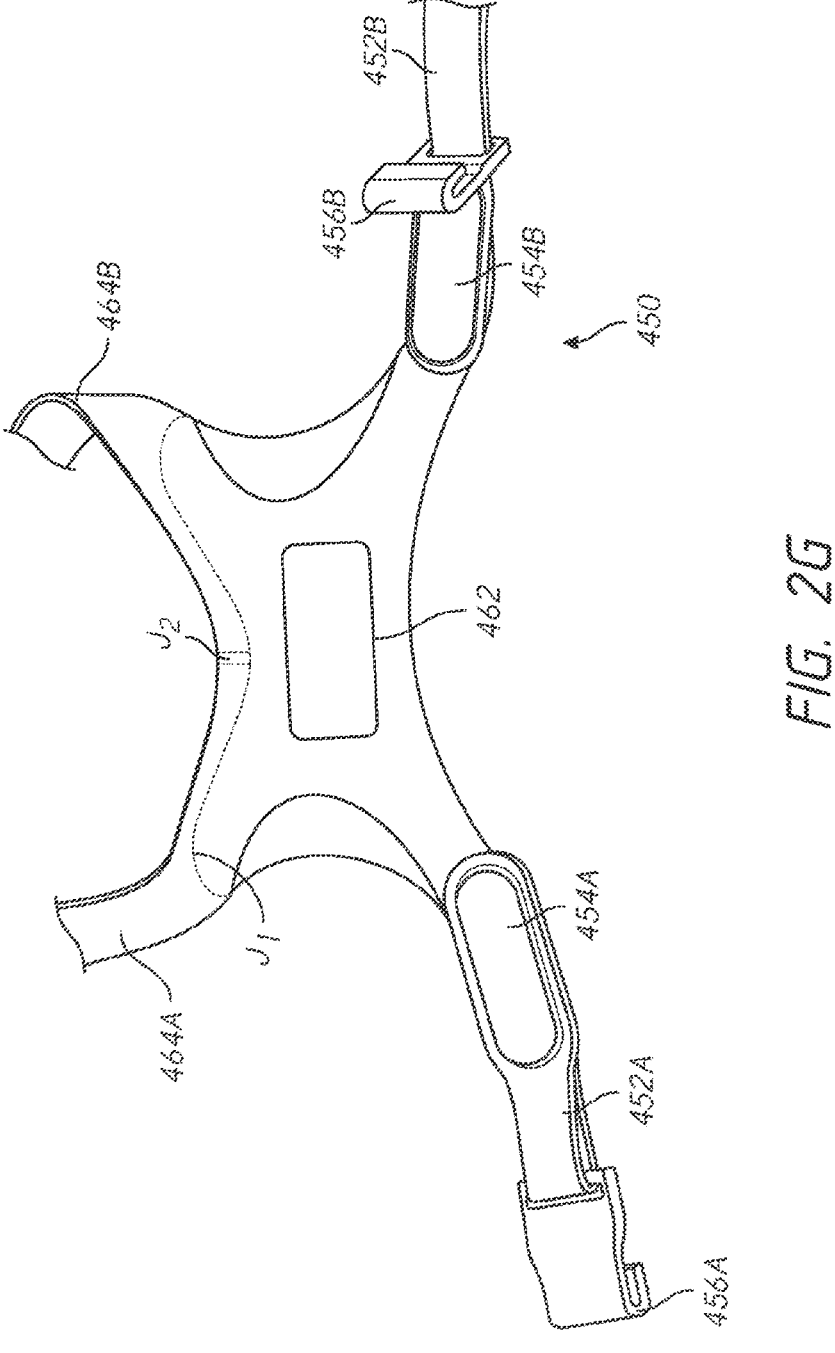
FIG. 2G shows a top plan view of headgear for a patient interface.

The headgear connection element 400A additionally comprises a progressive feedback element 406A. The progressive feedback element 406A is configured to provide force against the patient's face (e.g. the cheeks) commensurate with the particular fit of the patient interface 200 (e.g. the tightness or looseness of the fit of the headgear 450). The progressive feedback element 406A may be configured to provide more resistive force against the face when the headgear connection element 400A is moved closer towards the head of the user such that the fit is tight relative to when the fit is loose. The force may help to give feedback to the user as to whether the fit of the patient interface 200 is adequate, or may help to increase the comfort of the patient interface 200. The progressive feedback element 406A may help to transfer forces that would arise as a result of tightening the patient interface 200 on the head (e.g. forces applied to the nose or proximal to the nose) to the cheeks. Forces applied to the cheeks may be more tolerable to the user than forces applied to the nose. Additionally, displacement of the cushion module 510 on the nose may be avoided by transferring forces to the cheeks. As shown in FIGS. 3A-3C, the exemplary non-limiting progressive feedback element 406A comprises a substantially out-of-plane extension of the body 402A of the headgear connection element 400A from about the middle of the body 402A towards the second end of the headgear connection element 400A. An aperture 407 is defined in the plane of the body 402A by the out-of-plane extension. The extension acts as a cantilever, moving substantially transverse to the body and increasingly towards the aperture 407 as the force applied to the extension increases. The aperture 407 may have a size and shape to provide clearance for the progressive feedback element 406A such that the progressive feedback element 406A does not contact the headgear connection element 400A throughout its range of travel. As shown in FIG. 2F, the extension may comprise a soft or pliable padding or cover 410A to increase the comfort and feel of the progressive feedback element 406A. The cover 410A can comprise a number of materials, including but not limited to foams, soft plastics (e.g. silicones), fabrics and textiles. In the illustrated configuration, the cover 410A is adhered to the extension and/or body 402A such that all of the contact forces of the headgear connection element 400A are channeled through the cover 410A. In some configurations, the cover 410A may only be joined to the extension of the progressive feedback element 406A. In some configurations, the cover 410A may be integrally formed or may be in the form of a single continuous piece together with the extension and/or body 402A. Other ways of joining the cover 410A and the extension and/or body 402A, including but not limited to ultrasonic or high-frequency welding, stitching and mechanical fastening arrangements (e.g. push fit or bayonet fittings) may alternatively or additionally be used. In other configurations, a spring (e.g. a flat spring) and/or a resilient cushion may be used instead of or together with the extension to promote the delivery of force to the cheeks commensurate with the fit of the patient interface 200.

The force exerted by the illustrated progressive feedback element 406A on the cheeks is a function of the material, thickness, and width of the extension. However, in other configurations, if an extension is not used, traits of some other mechanism for providing a force may govern the function of the progressive feedback element 406A. The force of the progressive feedback element 406A against the cheeks may be proportional to the tightness of the fit of the patient interface 200. For example, the force against the cheeks may be linearly related to the fit tightness. In other configurations, the force of the progressive feedback element 406A against the cheeks may be non-linearly related to the fit tightness. For example, the force applied to the cheeks may be zero or low until a first predetermined or threshold fit tightness or force against the head is reached, and then the force applied may increase to a second predetermined or threshold force or may increase rapidly as the tightness increases beyond the first threshold tightness. As another example, the force applied to the cheeks may be high until a first fit tightness is reached, and then the force against the cheeks may decrease, remain steady, or increase more slowly as the fit tightness climbs above the first applied predetermined force.

A preferred embodiment of the patient interface 600 is disclosed in FIGS. 8A-8G. The patient interface 600 can be used with the respiratory therapy system 100 described with reference to FIG. 1. The patient interface comprises a frame 1000 (see FIGS. 10A-10D) adapted to receive gases from a gases source (for example, the flow generator 102 described elsewhere in this disclosure with reference to FIG. 1). The frame 1000 comprises a body 1001, left and right fixation regions 1002A, 1002B positioned between a central raised section 1012 and left and right fixation ridges 1006A, 1006B, left and right fixation elements 1004A, 1004B, left and right cushion supports 1008A, 1008B, a gases aperture 1010, and a cushion module retention portion defined by raised 1014 and depressed 1016 portions of a wall of the frame 1000 defining the gases aperture 1010.

The gases aperture 1010 is adapted to receive an elbow component 1100 (see FIG. 8F) configured to interface with a gases delivery conduit (for example, the gases conduit 112 described elsewhere in this disclosure with reference to FIG. 1). The elbow component 1100 comprises an elbow outlet portion 1102, a venting area 1104, an anti-asphyxia valve assembly 1106, a tube section 1108, and an elbow inlet portion 1110. The elbow component may be substantially the same or similar to the elbow component 1100 described with reference to the first non-limiting exemplary patient interface 200.

Figure 8A:
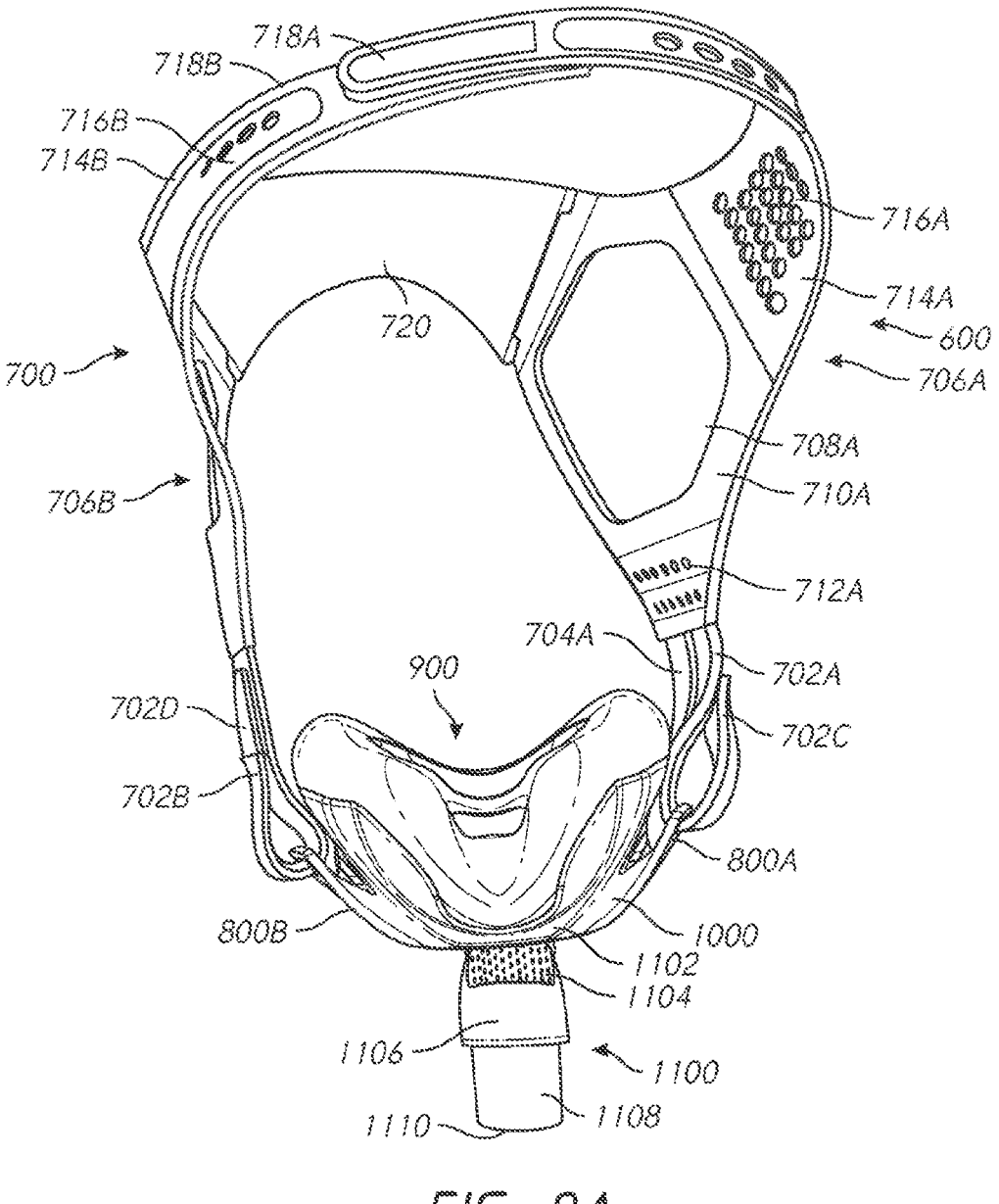
FIG. 8A shows a top plan view of a preferred embodiment of a patient interface.
Figure 8B:
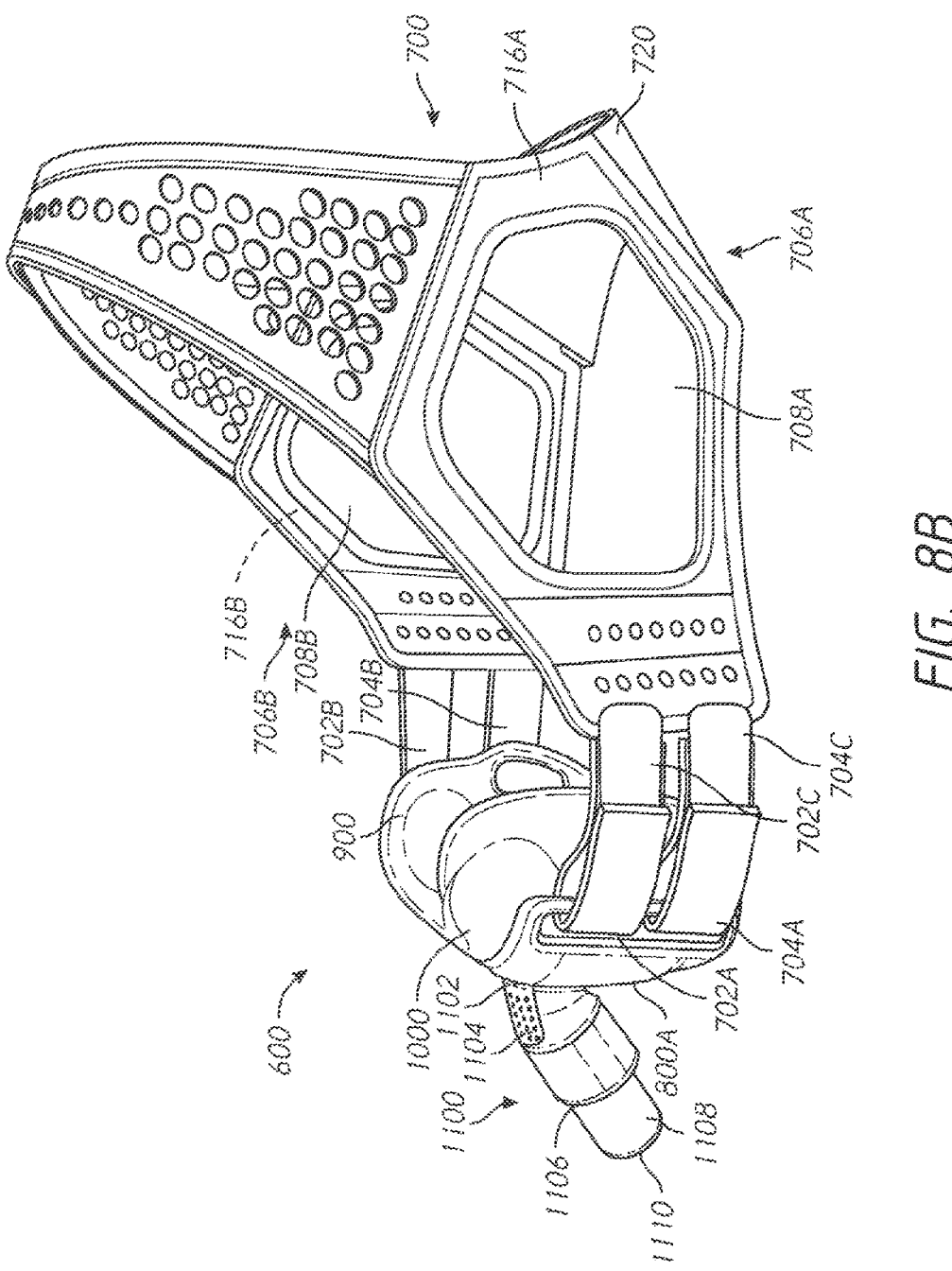
FIG. 8B shows a side plan view of the patient interface of FIG. 8A.
Figure 8C:
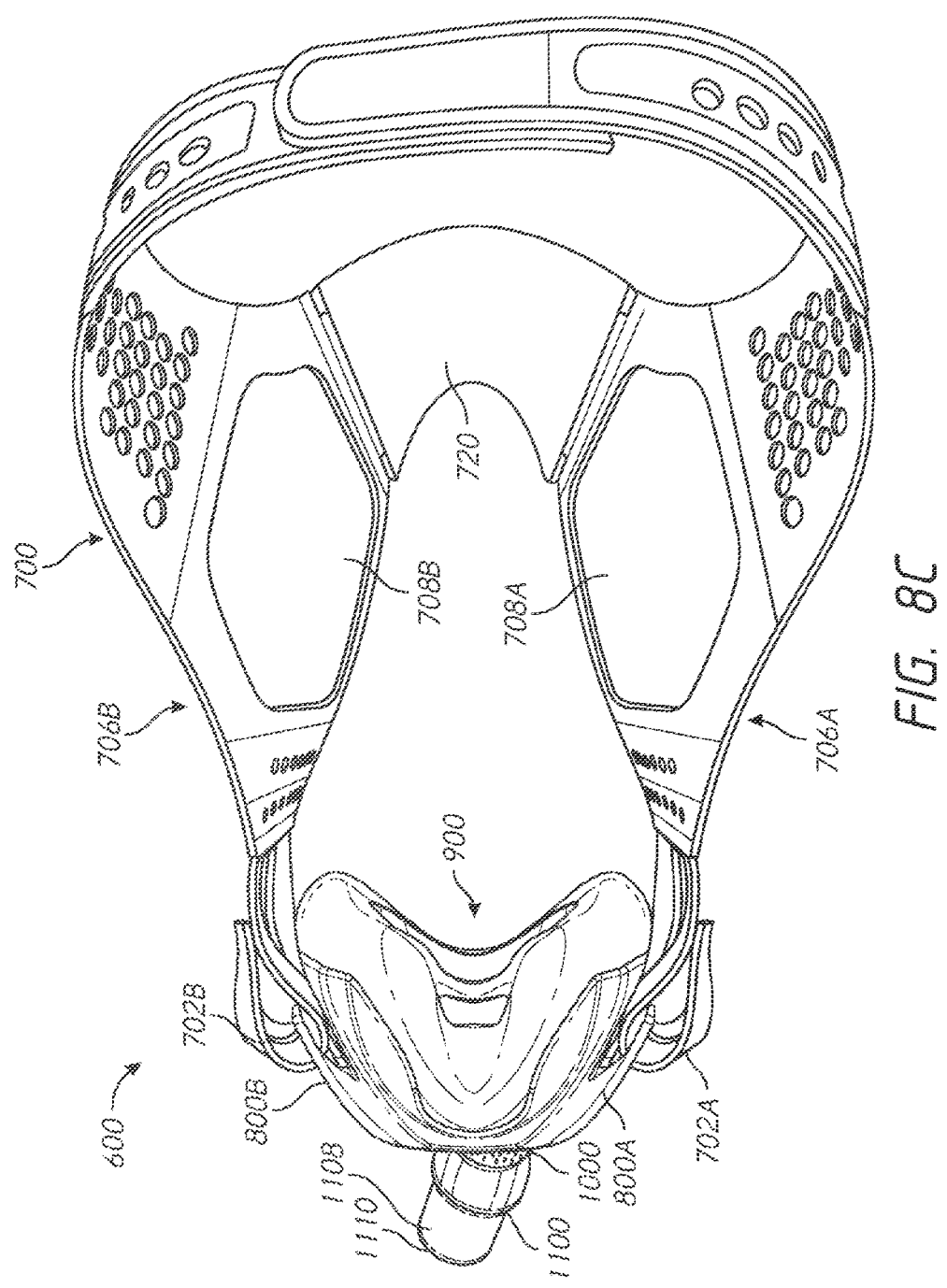
FIG. 8C shows a top side plan view of the patient interface of FIG. 8A.
Figure 8D:
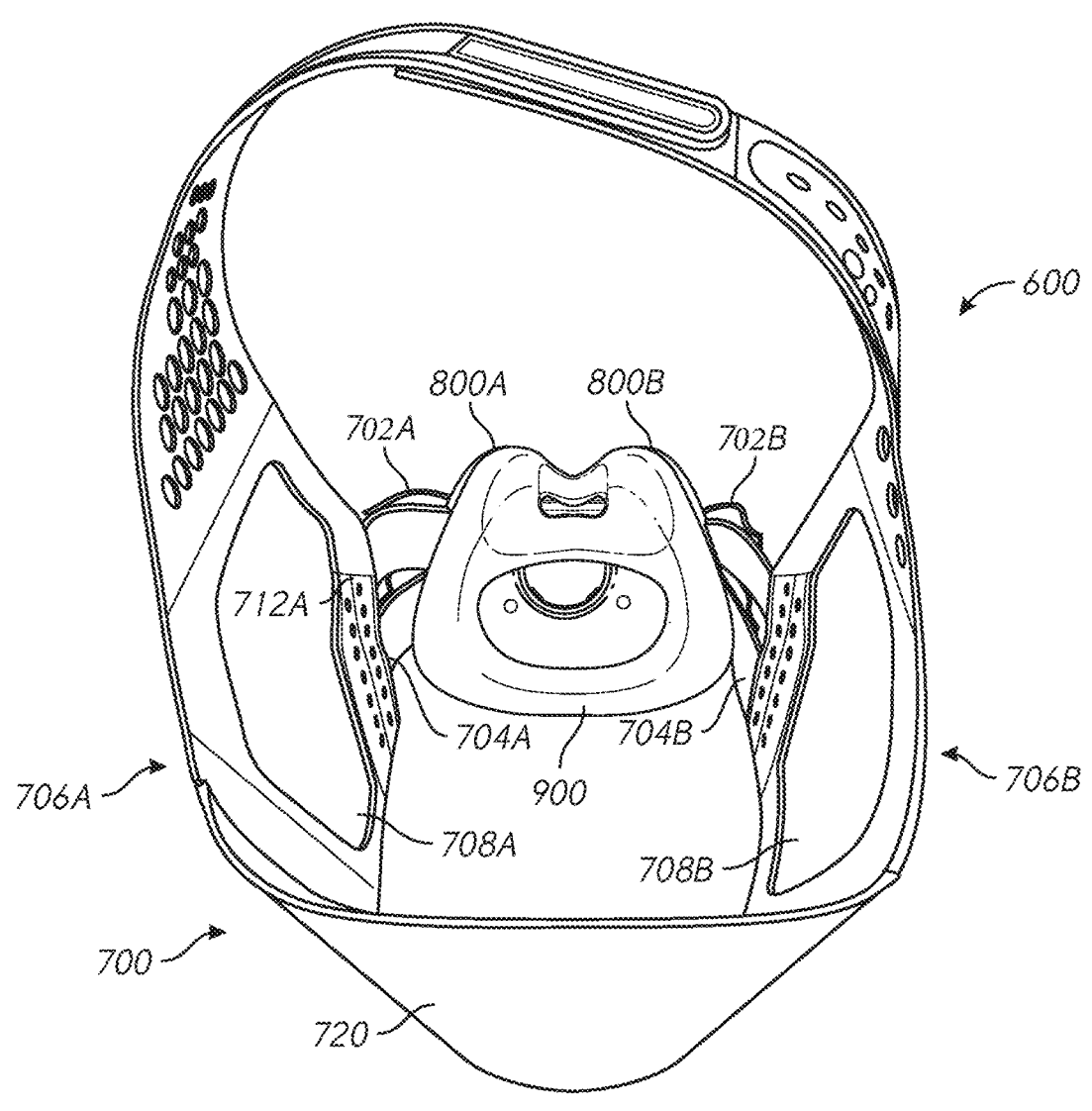
FIG. 8D shows a rear plan view of the patient interface of FIG. 8A.
Figure 8E:
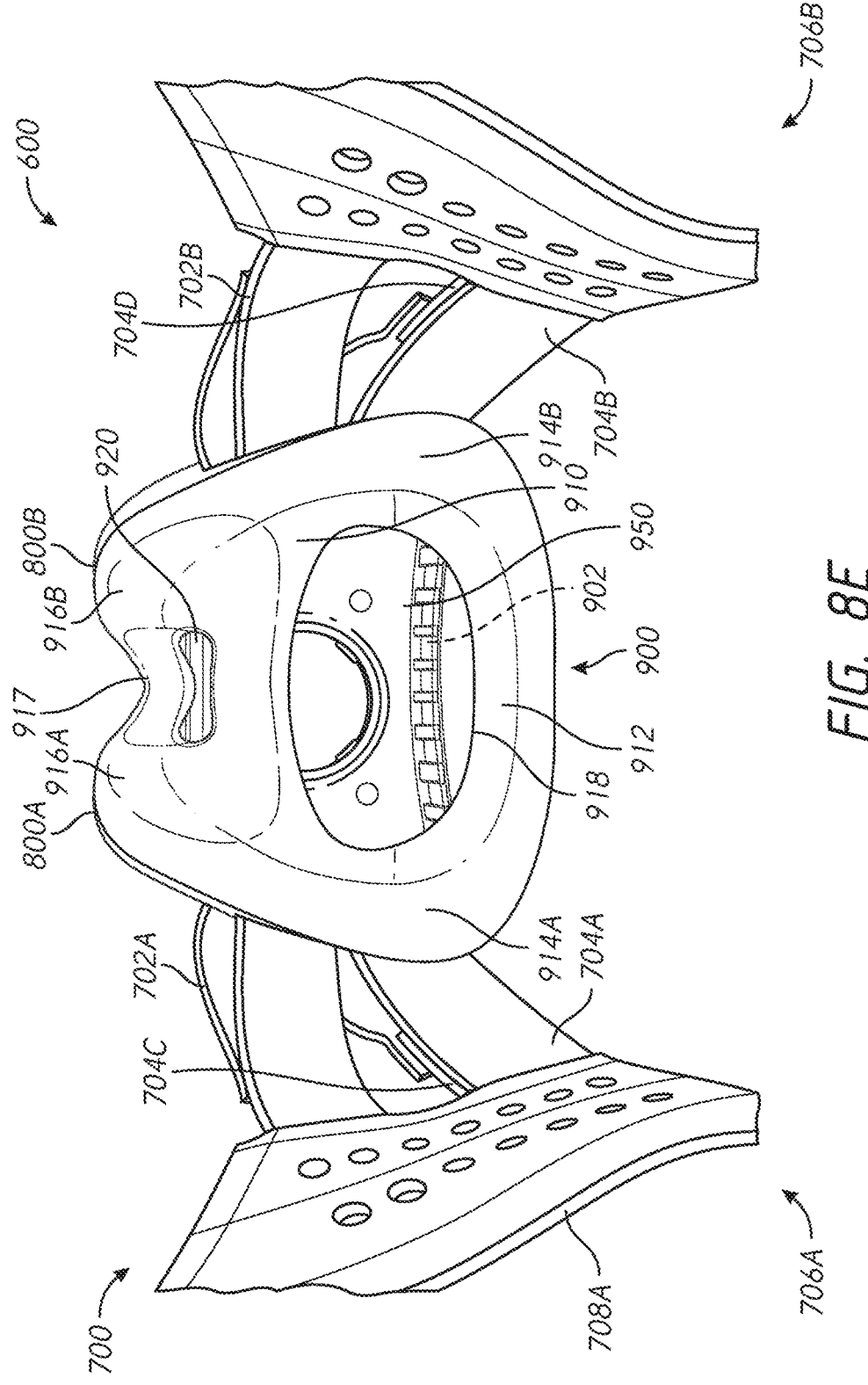
FIG. 8E shows a close-up rear plan view of the patient interface of FIG. 8A.
Figure 8F:
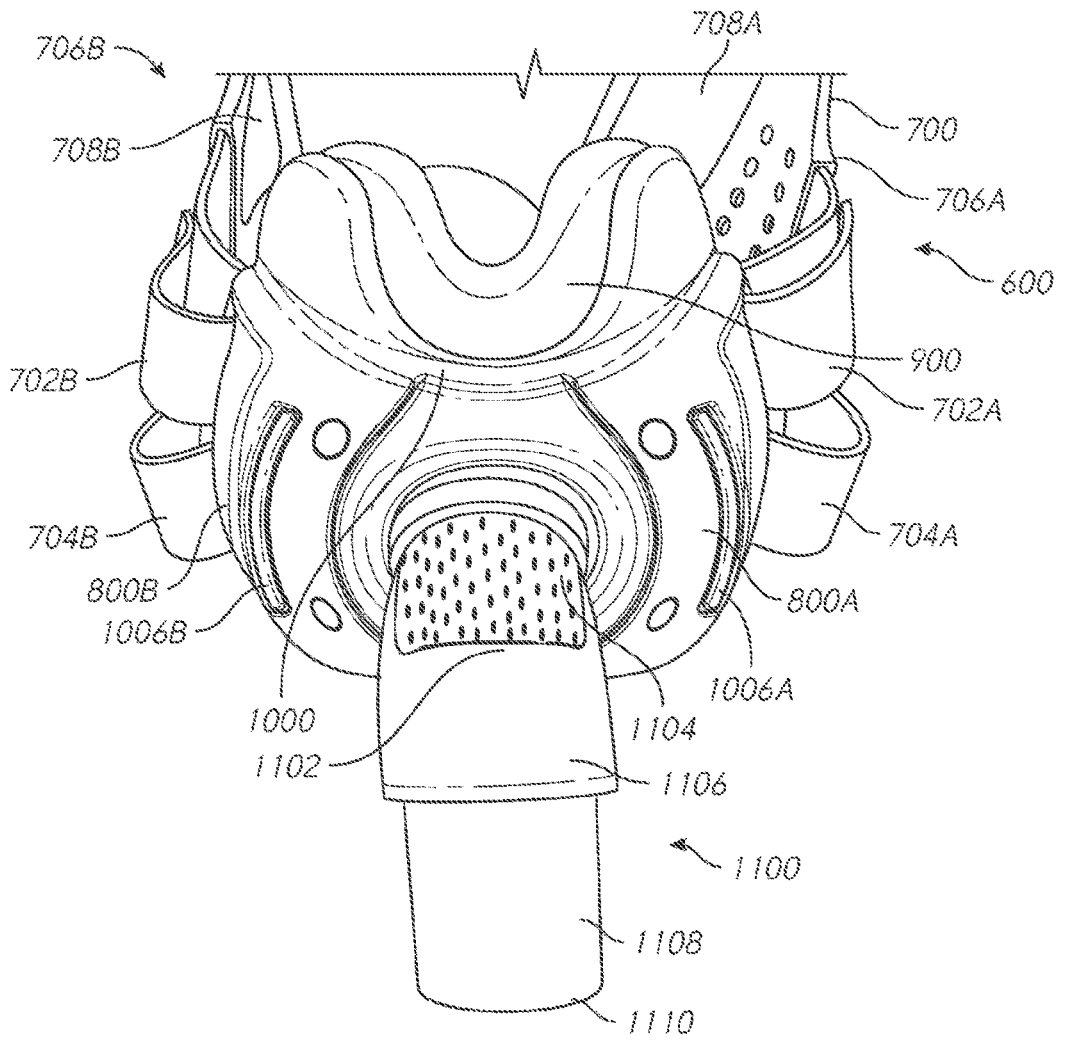
FIG. 8F shows a close-up top front plan view of the patient interface of FIG. 8A.
Figure 8G:
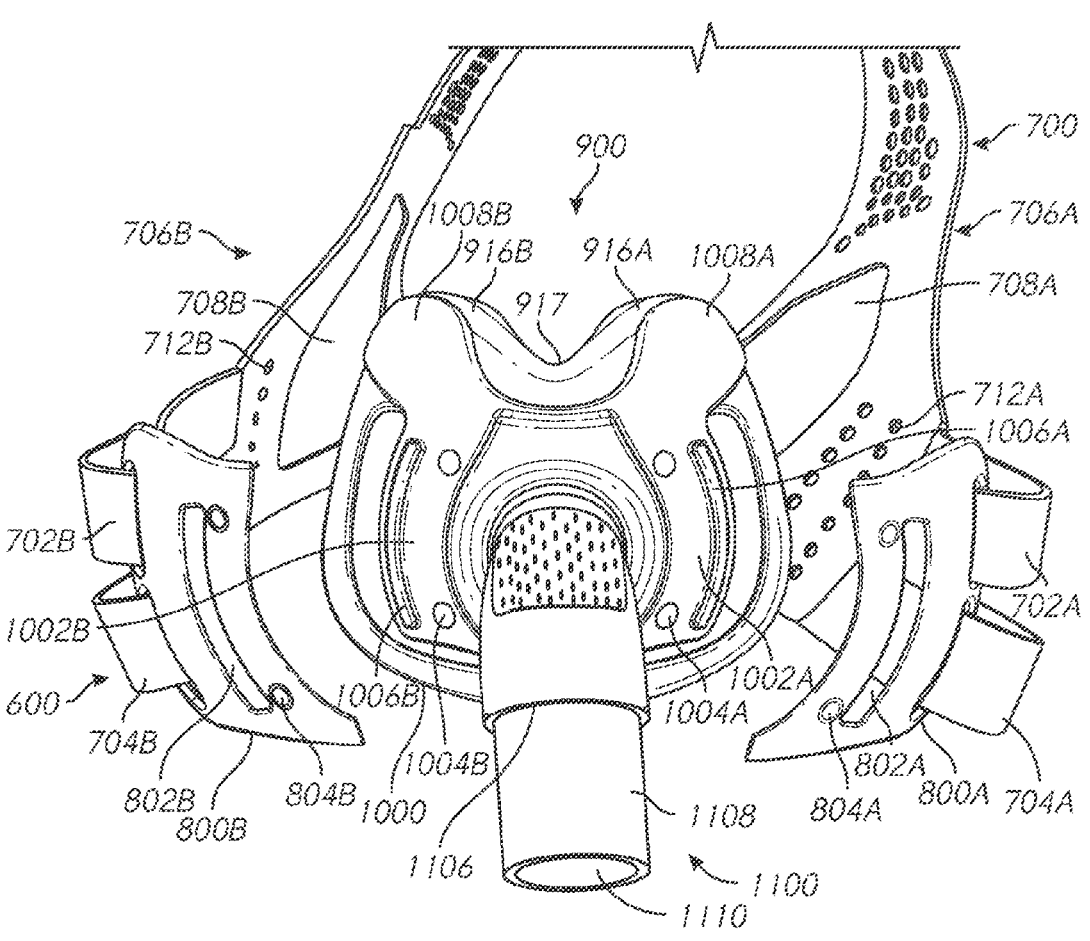
FIG. 8G shows a close-up front plan view of the patient interface of FIG. 8A.

The patient interface 600 comprises a cushion module 900 that engages with the frame 1000 (see FIG. 8E). The cushion module comprises a pliable seal or cushion member 910 configured to engage with the user's face. The cushion member 910 comprises a nasal recess 917 defined by left and right upper cushion ridges 916A, 916B, a nasal gases passageway 920, an oral gases passageway 918 bounded by left and right side portions 914A, 914B and by a bottom portion 912, and a cushion brace 950. The cushion module 900 may be substantially the same or similar to the cushion module 500 described with reference to the first non-limiting exemplary patient interface 200. Additionally, the means for engagement between the cushion module 900 and the frame 1000 (e.g. using the cushion module retention portion) may be substantially the same or similar to the means for engagement between the cushion module 500 and the frame 300 described with reference to the first non-limiting exemplary patient interface 200.

The patient interface 600 additionally comprises left and right headgear connection elements 800A, 800B. In the illustrated configuration, the left and right headgear connection elements 800A, 800B are mirror images of one another, and so the disclosure will be focused on the right headgear connection element 800B. However, in other configurations, the headgear connection elements 800A, 800B could have different shapes or characteristics. Dissimilar headgear connection elements 800A, 800B could be useful dependent on the shape or dissymmetry of the user's head. The headgear connection elements 800A, 800B are attached to the frame 1000 such that the headgear connection elements 800A, 800B are angled toward each other (i.e., projected planes of each of the headgear connection elements 800A, 800B converging) such that force vectors are transmitted to the headgear (not shown) at an angle to ensure proper sealing and comfort between the cushion module 900 and the user. Further, the headgear connection elements 800A, 800B may have a curved concave inner surface that corresponds to the shape of the outer surface of the frame 1000 upon which the headgear connection elements 800A, 800B are mounted. Similarly, the headgear connection elements 800A, 800B may have a curved convex outer surface that is flush with the central raised section 1012 and follows the aesthetic contours of the frame 1000.

Figures 9A, 9B:
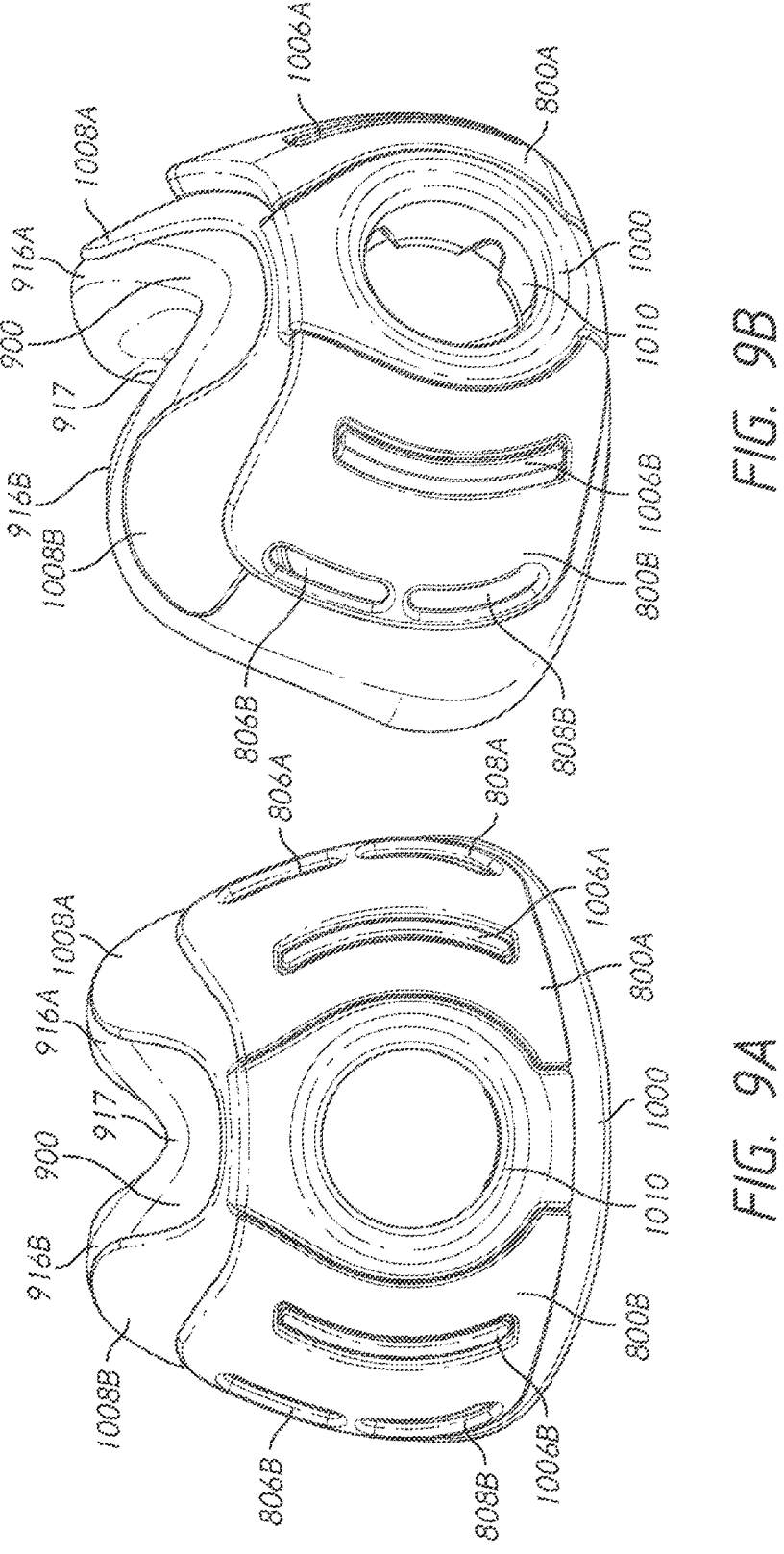
FIG. 9A shows a front plan view of a cushion module assembly.
FIG. 9B shows a front side plan view of the cushion module assembly of FIG. 9A.

The right headgear holding element 800B (see FIGS. 10E and 10F) comprises a fixation region interfacing section 802B, complementary fixation elements 804B, and headgear slots 806B, 808B. Similarly, the left headgear holding element 800A comprises a fixation region interfacing section 802A, complementary fixation elements 804A, and headgear slots 806A, 808A. The illustrated fixation region interfacing section 802B comprises an aperture having a shape complementary to the shape of the right fixation ridge 1006B such that the right fixation ridge 1006B can be positioned within the aperture. The complementary fixation elements 804B interface with the fixation elements 1004B present on the frame 1000 to retain the right headgear connection element 800B in a predetermined position and/or alignment relative to the frame 1000. In the envisioned orientation, the right headgear connection element 800B can be substantially located in the space between the central raised section 1012 of the frame 1000 and the right fixation ridge 1006B such that the right fixation ridge 1006B protrudes through the aperture of the fixation region interfacing section 802B and such that the fixation elements 1004B align with the complementary fixation elements 804B (see FIGS. 9A-9B). In the illustrated configuration, the fixation elements 1004B and the complementary fixation elements 804B are magnets. However, in other configurations the fixation elements 1004B and complementary fixation elements 804B may comprise other mechanisms or structures adapted to promote retention of the right headgear connection element 800B, including but not limited to hook-and-loop pads or patches, mechanical interlock arrangements, and releasable adhesives. Additionally, in other configurations the left and/or right headgear connection elements 800A, 800B may be integrally moulded or with in the form of a single continuous piece together with the frame 1000.

Figure 11A:
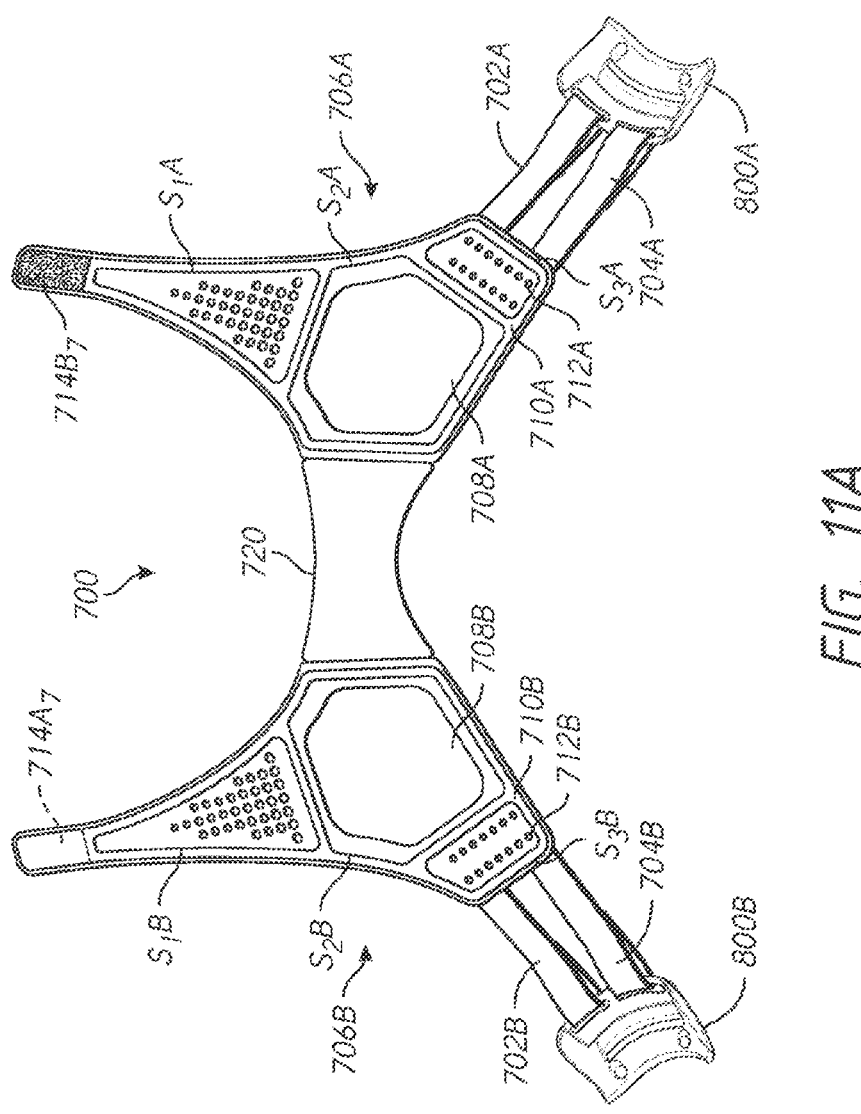
FIG. 11A shows a top-down view of a headgear assembly.

The right headgear slots 806B, 808B are adapted to make a two-point connection with a right upper strap 702B and a right lower strap 704B of headgear 700 (together with left headgear slots 806A, 808A of the left headgear connection element 800A and with left upper and lower straps 702A, 704A forming a four-point connection; see FIG. 11A). The ends 702D, 704D of the right upper and lower straps 702B, 704B (see FIG. 8A; 704D not shown) can extend through the right headgear slots 806B, 808B and can be looped upon themselves and secured to the remaining portion of the bodies of the right upper and lower straps 702B, 704B. Similarly, the ends 702C, 704C of the left upper and lower straps 702A, 704A (see FIG. 8B) can extend through the left headgear slots 806A, 808A and can be looped upon themselves and secured to the remaining portion of the bodies of the left upper and lower straps 702A, 704A. In the illustrated configuration, the ends 702D, 704D may be secured to the bodies by using hook patches on the ends 702D, 704D that interface with looped surfaces of the bodies (in a hook-and-loop style fastening arrangement). In other configurations, other means of securing the ends 702D, 704D may be used, including but not limited to resealable adhesives and mechanical fastening arrangements (e.g. clasps, zips, buttons, etc.). The right upper and lower straps 702A, 704A may be the same or similar to the right top and bottom straps 458B, 452B of the headgear 450 described with reference to the first non-limiting exemplary patient interface 200.

Further attention is given to the headgear 700 with reference to FIGS. 11A-11D. The illustrated headgear 700 comprises left and right upper straps 702A, 702B, left and right lower straps 704A, 704B, left and right side panels 706A, 706B, crown straps 718A, 718B, and a back section 720.

Figure 11B:
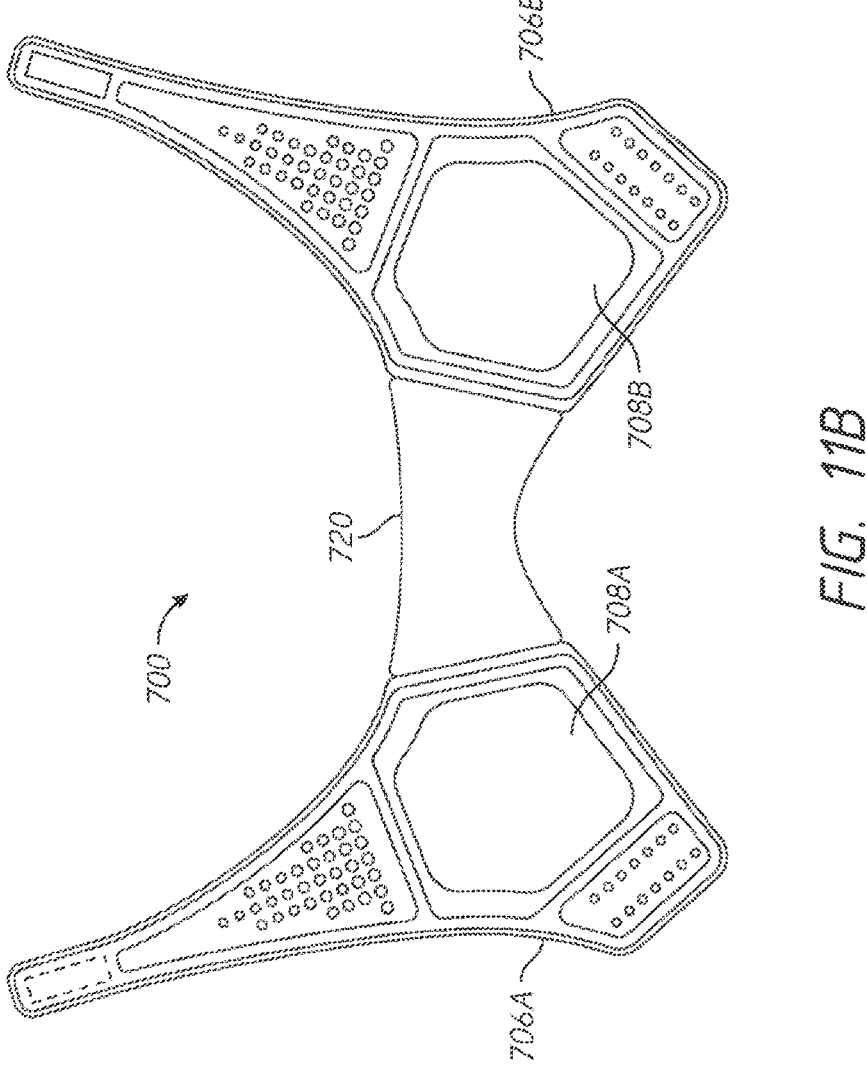
FIG. 11B shows a top-down view of a headgear assembly.
Figure 11C:
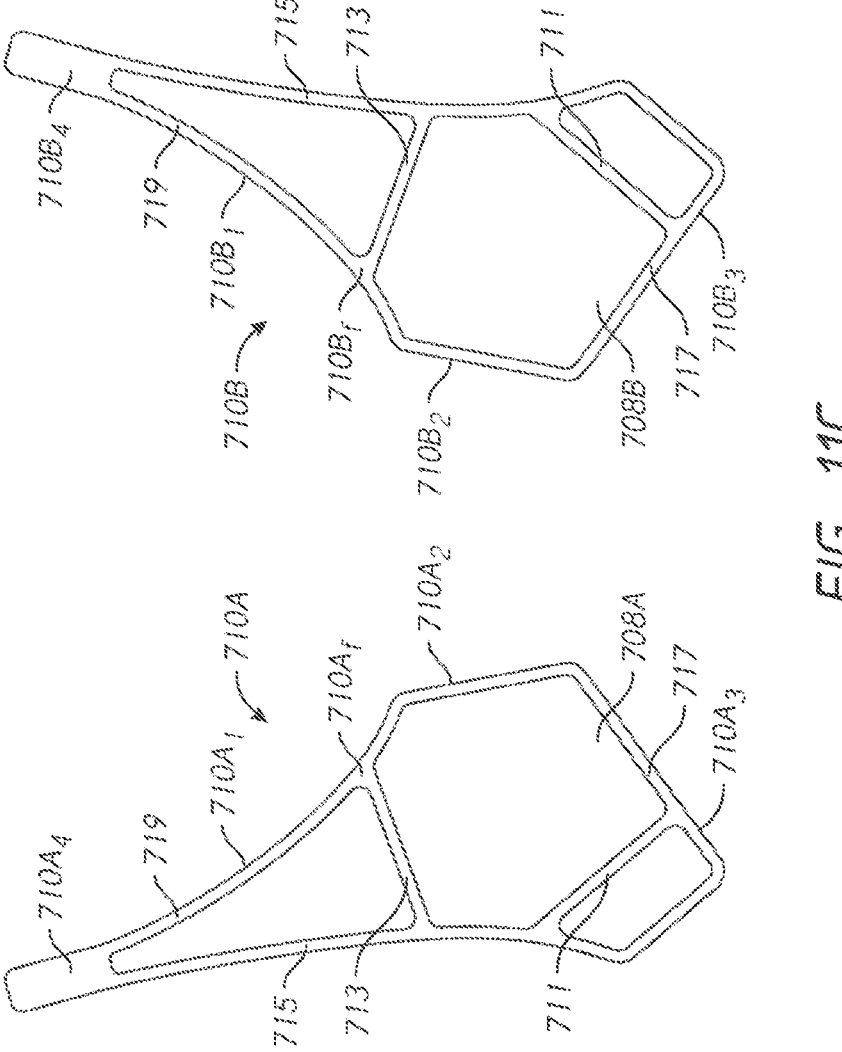
FIG. 11C shows a top-down view of a headgear framework.

The left and right side panels 706A, 706B comprise rigid or semi-rigid frameworks or skeletons $710A_f$, $710B_f$ adapted to provide support to the headgear 700 (see FIG. 11C). The frameworks $710A_f$, $710B_f$ can be formed at least in part from a number of rigid or semi-rigid plastics or resins including but not limited to polyethylene and polypropylene. In the illustrated configuration, the material for the frameworks $710A_f$, $710B_f$ has been chosen such that the frameworks $710A_f$, $710B_f$ are more rigid than other parts of the headgear 700 but not so rigid as to be unable to flex or bend as the headgear 700 is put over the head. Further, the frameworks $710A_f$, $710B_f$ provides rigidity to ensure that the headgear assembly 1500 (or at least the ear loops 1510A, 1510B) may retain its shape without collapsing onto itself. In some configurations, the material used for the frameworks $710A_f$, $710B_f$ comprises a higher modulus of elasticity and/or higher flexural modulus than materials used for other parts of the headgear 700, particularly for the overlays 714A, 714B (described elsewhere) and/or for the back section 720. In an exemplary embodiment, the frameworks $710A_f$, $710B_f$ comprise front portions $710A_3$, $710B_3$, rear portions $710A_2$, $710B_2$, top portions $710A_1$, $710B_1$, and crown portions $710A_4$, $710B_4$. The front portions $710A_3$, $710B_3$ are separated from the rear portions $710A_2$, $710B_2$ by a vertical rib 711. The crown portions $710A_4$, $710B_4$ and the rear portions $710A_2$, $710B_2$ are separated by a lateral rib 713. In other words, the vertical rib 711 connects an inner portion of a front segment 715 of the frameworks $710A_f$, $710B_f$ with an inner portion of a bottom segment 717 of the frameworks $710A_f$, $710B_f$. The vertical rib 711 connects an inner portion of the front segment 715 of the frameworks $710A_f$, $710B_f$ with an inner portion of a rear segment 719 of the frameworks $710A_f$, $710B_f$. The vertical rib 711 and the lateral rib 713 by connecting inner regions of the frameworks $710A_f$, $710B_f$ increases structural rigidity and strength to reduce or limit stretching of the frameworks $710A_f$, $710B_f$ when horizontal and vertical forces are exerted on the frameworks $710A_f$, $710B_f$ when the headgear is fitted to the head. More specifically, the vertical rib 711 reduces or limits vertical displacement between the front segment 715 and the bottom segment 717 and the lateral rib 713 reduces or limits lateral displacement between the front segment 715 and the rear segment 719. Increasing rigidity and limiting stretching of the frameworks $710A_f$, $710B_f$ improves sealing between the cushion member and the user. The front portions $710A_3$, $710B_3$ define substantially right trapezoid-like apertures and are adapted to be positioned below or near the cheekbones (for example and not limited to, positioned over the zygomaticus minor, zygomaticus major, buccinator and/or risorious). The rear portions $710A_2$, $710B_2$ define substantially hexagonal apertures 708A, 708B and are adapted to be positioned on the sides of the head around the ears (for example and not limited to, positioned over the temporalis, aricularis anterior, aricularis superior, aricularis posterior and/or sternocleidomastoid). The top portions $710A_1$, $710B_1$ define substantially triangular or scalene trapezoid-like apertures and are adapted to extend upward along the head towards the crown (for example and not limited to, extending from the rear portions $710A_2$, $710B_2$ towards and over the parietal portion of the skull). Crown portions $710A_4$, $710B_4$ (having a substantially rectangular shape) extend from the top portions $710A_1$, $710B_1$ and are adapted to be positioned on or near the top of the head (for example and not limited to, positioned over the parietal portion of the skull). The crown portions $710A_4$, $710B_4$ define no apertures and are substantially square or trapezoidal. The crown portions $710A_4$, $710B_4$ may be directly or indirectly adapted to be joined to one another to fix the headgear 700 on the head (for example, through the joining elements $714A_7$, $714B_7$ on the overlays 714A, 714B described elsewhere). The right crown portion $710B_4$ is longer than the left crown portion $710B_4$ to allow for an adjustable join between the crown portions $710A_4$, $710B_4$. In the illustrated configuration, the portions of the frameworks $710A_f$, $710B_f$ are integrally formed or in the form of a single continuous piece. In other configurations, the portions may be separate and joined together. In some configurations, portions of the frameworks $710A_f$, $710B_f$ may have different properties (for example, different levels of rigidity, elasticity and/or flexibility). For example, in some such configurations the rear portions $710A_2$, $710B_2$ may be more flexible or elastic than the front portions $710A_3$, $710B_3$ In other configurations, the portions could have other shapes. For example, although the shapes of the hexagonal apertures for the rear portions $710A_2$, $710B_2$ improve the stability of the side panels 706A, 706B relative to some other possible shapes, the apertures could alternatively be circular or polygonal (e.g. rectangular).

Figure 11D:
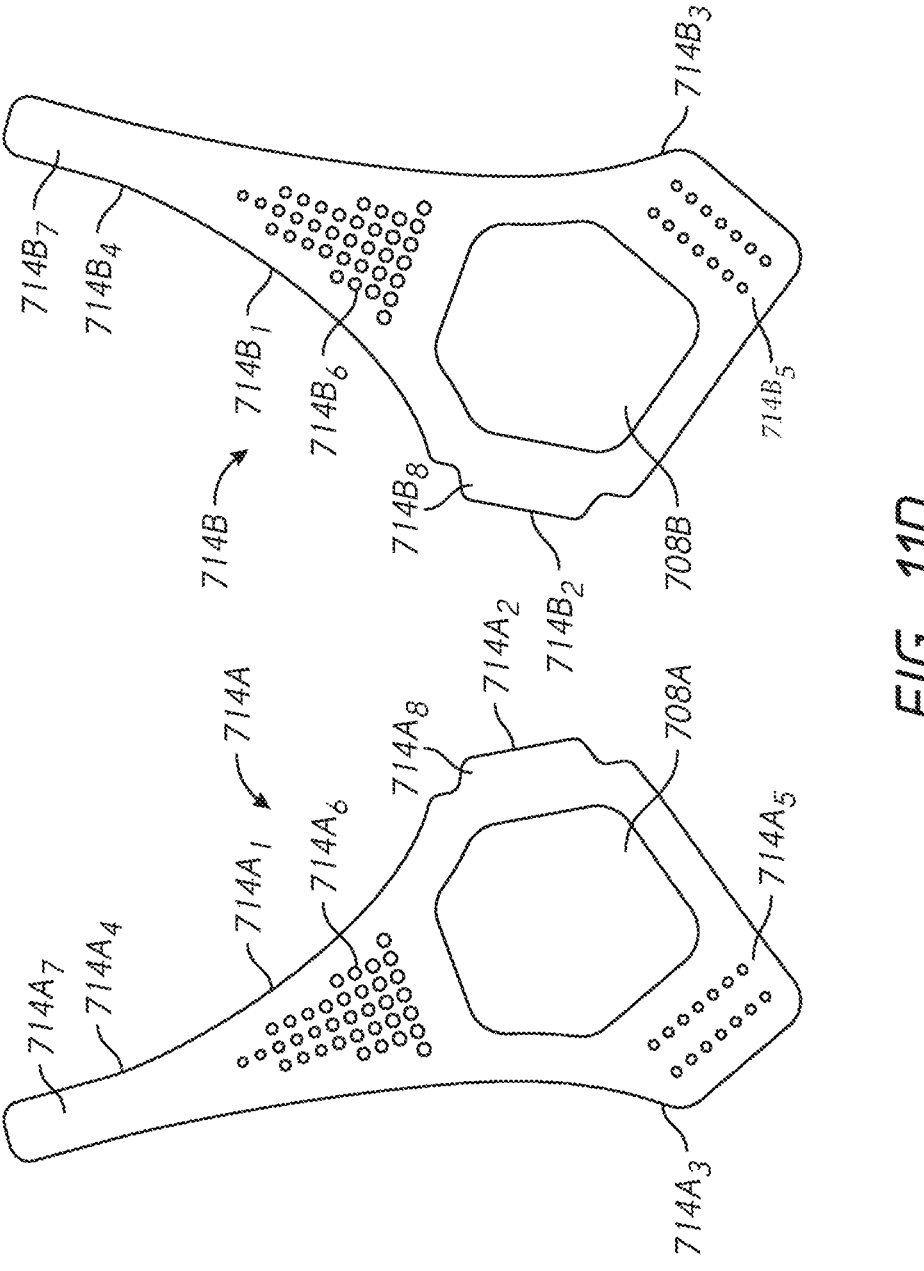
FIG. 11D shows a top-down view of a headgear overlay.

FIG. 11D shows overlays 714A, 714B that are used in the headgear 700 together with the frameworks $710A_f$, $710B_f$. More specifically, each of the frameworks $710A_f$, $710B_f$ is sandwiched between two layers of the overlays 714A, 714B, respectively. The overlays 714A, 714B contact the face and are constructed at least in part from a relatively pliable or soft material to provide softness against the skin. The overlays 714A, 714B comprise front portions $714A_3$, $714B_3$, rear portions $714A_2$, $714B_2$, top portions $714A_1$, $714B_1$, and crown portions $714A_4$, $714B_4$. The portions of the overlays 714A, 714B substantially correspond with the portions of the frameworks $710A_f$, $710B_f$. In the illustrated configuration, the overlays 714A, 714B are constructed at least in part using a microfiber material. In other configurations, the overlays 714A, 714B can be constructed using other materials, including but not limited to fabrics, textiles, cloth, and plastics. Materials having a relatively high compressibility, flexibility, elasticity, breathability and/or softness (e.g. relative to the materials used for the frameworks $710A_f$, $710B_f$) may be used. In some configurations, the overlays 714A, 714B may comprise multilayer structures or composites. For example, in some configurations, the overlays 714A, 714B may comprise a first layer adapted to be placed on the face and a second layer covering the first layer. The first layer may be more compressible, more flexible, more elastic and/or softer than the second layer. In some configurations, the overlays 714A, 714B may have different properties in different sections of the overlays 714A, 714B. For example, the overlays 714A, 714B may be thicker at the rear portions $714A_2$, $714B_2$ than at the front portions $714A_3$, $714B_3$, top portions $714A_1$, $714B_1$, and/or crown portions $714A_4$, $714B_4$. As another example, the top portions $714A_1$, $714B_1$ may be constructed from a more extensible, more pliable, or softer material than the front portions $714A_3$, $714B_3$, rear portions $714A_2$, $714B_2$, and/or crown portions $714A_4$, $714B_4$. In the illustrated configuration, the portions of the overlays 714A, 714B are integrally formed or in the form of a single continuous piece. In other configurations, the portions may be separate and joined together. In some configurations, portions of the overlays 714A, 714B may have different properties (for example, different levels of rigidity, elasticity and/or flexibility). For example, in some such configurations the rear portions $714A_2$, $714B_2$ may be more flexible or elastic than the front portions $714A_3$, $714B_3$.

In the illustrated configuration, the shapes of the portions of the overlays 714A, 714B are similar to the shapes of the frameworks $710A_f$, $710B_f$. That is, the front portions $714A_3$, $714B_3$ have substantially right trapezoid-like shapes (adapted to cover the corresponding apertures in the front portions $710A_3$, $710B_3$ of the frameworks $710A_f$, $710B_f$), the rear portions $714A_2$, $714B_2$ have substantially hexagonal shapes (where the apertures 708A, 708B are still exposed), the top portions $714A_1$, $714B_1$ have substantially triangular or scalene trapezoid-like shapes (adapted to cover the corresponding apertures in the top portions $710A_1$, $710B_1$ of the frameworks $710A_f$, $710B_f$), and the crown portions $714A_4$, $714B_4$ have a substantially rectangular or trapezoidal shape.

The rear portions $714A_2$, $714B_2$ comprise substantially trapezoidal extensions $714A_8$, $714B_8$ that project outwardly from the hexagonal shapes to provide additional support to the back section 720. In other configurations, the portions could have other shapes. For example, the rear portions $714A_2$, $714B_2$ could comprise a number of polygonal shapes (e.g. rectangular or triangular) or non-polygonal shapes (e.g. circular) rather than a hexagonal shape.

Figure 14:
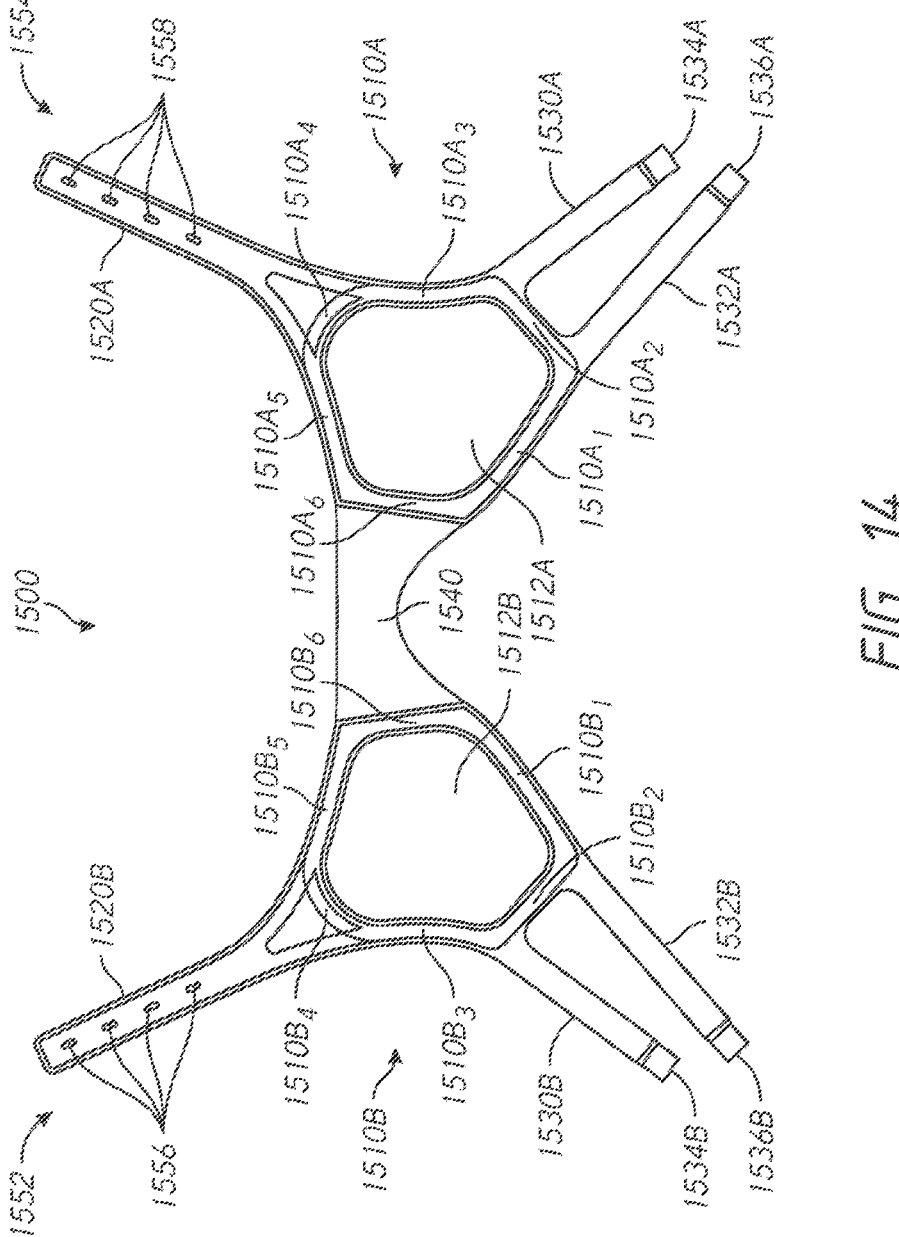
FIG. 14 shows a top view of a headgear assembly of the present disclosure in a flattened condition.

The overlays 714A, 714B also comprise air apertures 712A, 712B, $714A_5$, $714B_5$, $714A_6$, $714B_6$. The air apertures improve the breathability and decrease the weight of the overlays 714A, 714B. In the illustrated configuration, the front portions $714A_3$, $714B_3$ comprise substantially rectangular sections of air apertures (e.g. 2 rows of 7 apertures) $714A_5$, $714B_5$, and the top portions $714A_1$, $714B_1$ comprise substantially triangular sections of air apertures (e.g. 10 rows of 7, 5, 5, 5, 3, 3, 3, 3, 1 and 1 apertures extending towards the crown portions $714A_4$, $714B_4$, or in some cases and as shown in FIG. 11A, 14 rows of 7, 5, 5, 5, 3, 3, 3, 3, 1, 1, 1, 1, 1 and 1 apertures) $714A_6$, $714B_6$. The sections of air apertures illustrated are configured to convey acceptable breathability for the given overlay shapes while maintaining the structural integrity and strength of the overlays 714A, 714B. However, in some configurations, the air apertures may be positioned in other places. For example, in some configurations the rear portions $714A_2$, $714B_2$ and/or the crown portions $714A_4$, $714B_4$ of the overlays 714A, 714B may comprise air apertures. In some configurations, the sections of air apertures could have different shapes. For example, in some configurations, the sections of air apertures on the top portions $714A_1$, $714B_1$ could be rectangular or circular. The air apertures themselves could, for example, be rectangular or triangular.

As described, the overlays 714A, 714B are attached to the frameworks $710A_f$, $710B_f$. In the illustrated configuration (see FIG. 11A), the overlays 714A, 714B are stitched to the frameworks $710A_f$, $710B_f$ along continuous seam portions $S_1A$, $S_1B$, $S_2A$, $S_2B$, $S_3A$, $S_3B$. In other configurations, the overlays 714A, 714B may be attached to the frameworks $710A_f$, $710B_f$ using multiple discontinuous seams or stitching regions. In still other configurations, the overlays 714A, 714B may attached to the frameworks $710A_f$, $710B_f$ by other means, including but not limited to adhesives, ultrasonic welding, high-frequency welding, or mechanical fastening arrangements. In some configurations, the frameworks $710A_f$, $710B_f$ may be overmoulded onto the overlays 714A, 714B. Additional methods of using overmoulding techniques to join flexible and rigid sections of headgear are shown in commonly-owned U.S. 62/050,925, which is hereby incorporated by reference in its entirety and included by appendix. Additionally, joining elements $714A_7$, $714B_7$ are joined to the crown portions $710A_4$, $710B_4$ of the frameworks $710A_f$, $710B_f$ and to the crown portions $714A_4$, $714B_4$ of the overlays 714A, 714B (e.g. via stitching). The left joining element $714A_7$ is a loop patch positioned on the back (not clearly visible in FIG. 11A), while the right joining element $714B_7$ is a hook element positioned on the front (for a hook-and-loop style connection). In other configurations, the left and right joining elements $714A_7$, $714B_7$ may be joined via other means, including but not limited to resealable adhesives.

Additionally, in the illustrated configuration, support layers 716A, 716B (see FIG. 8B) are joined to the frameworks $710A_f$, $710B_f$. The support layers 716A, 716B lie on the sides of the frameworks $710A_f$, $710B_f$ opposite the overlays 714A, 714B (e.g. facing away from the head) and provide additional support to the headgear 700. The support layers 716A, 716B are stitched onto the frameworks 710A$_f$, 710B$_f$ and/or overlays 714A, 714B along seams S$_2$A, S$_2$B and to the frameworks 710A$_f$, 710B$_f$, overlays 714A, 714B, and/or left and/or right upper and lower straps 702A, 702B, 704A, 704B. The support layers 716A, 716B may be constructed from materials that are breathable, such as but not limited to fabrics, foams, fabric/foam composites and BREATH-O-PRENE™. Examples of fabrics may include, but are not limited to, cotton, nylon, or polyester blends.[0154] FIG. 11B shows the assembled left and right side panels 706A, 706B. The back section 720 is configured to support the back of the head (e.g. over the parietal and/or occipital portions of the skull), and comprises a band of material that is fixed to the side panels 706A, 706B along edges of the rear portions 714A$_2$, 714B$_2$ of the overlays 714A, 714B (e.g. via stitching, ultrasonic or high-frequency welding, adhesives, etc.). The band of material is greatest in width at the ends of the band nearest to the side panels 706A, 706B, and tapers to a minimum width at the middle of the band along the bottom edge of the band. The material used for the band can comprise a number of materials, including but not limited to fabrics, foams, fabric/foam composites BREATH-O-PRENE™, and spacer fabrics. In some configurations, the band can comprise a material having a lower modulus of elasticity and/or higher breathability than the materials used for the frameworks 710A$_f$, 710B$_f$ and/or overlays 714A, 714B.

Figure 13:
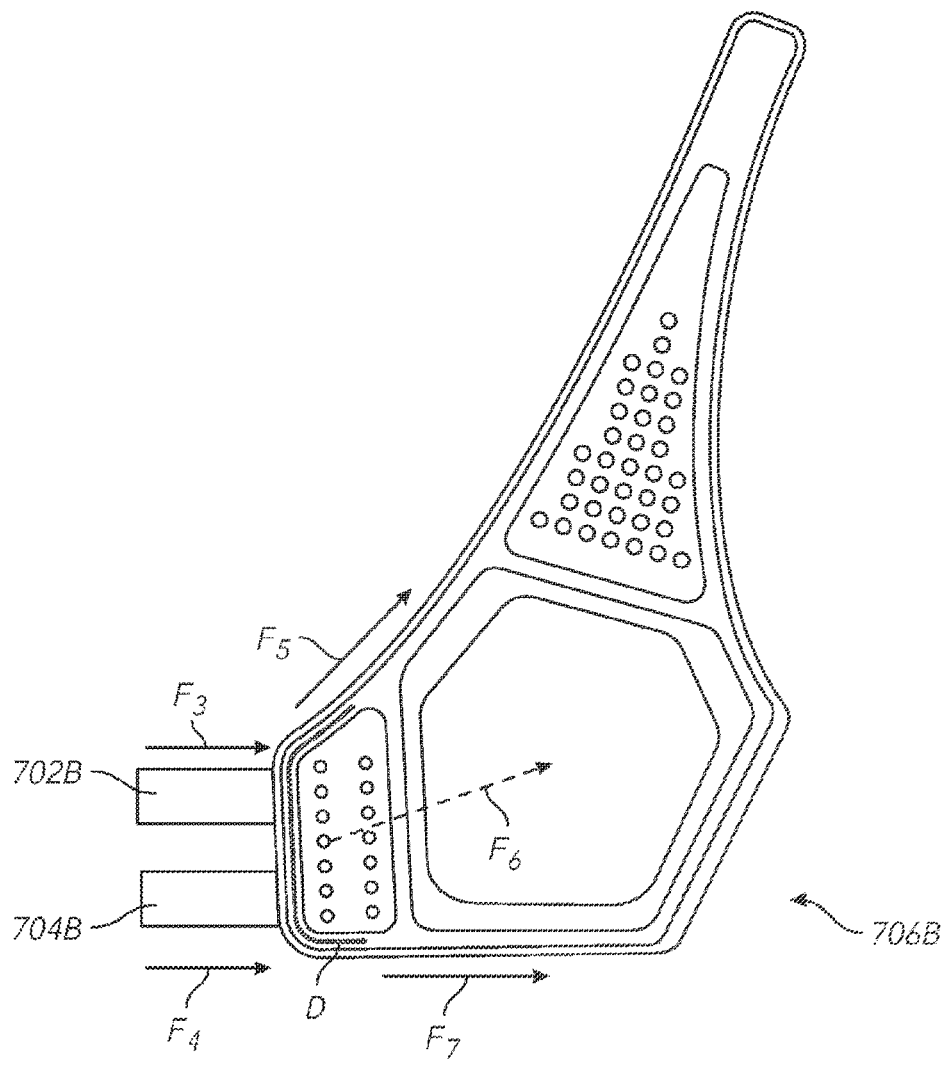
FIG. 13 shows forces applied to an exemplary headgear.

FIG. 13 shows the right panel 706B of FIG. 11B (i.e., including the framework 710B$_f$ and overlays 714B) connected to right upper and lower straps 702B, 704B. Accordingly, the right upper and lower straps 702B, 704B are connected to the framework 710B$_f$. Forces F$_3$, F$_4$ are applied to the straps 702B, 704B when the headgear 700 (attached to the remaining parts of the patient interface 600) is fitted to the head. The forces F$_3$, F$_4$ comprise a relatively large horizontal vector component and a relatively small vertical vector component. The forces F$_3$, F$_4$ are transferred to the right panel 706B and converted to forces F$_5$ and F$_7$ which act upon the right panel 706B. The force F$_5$ has both moderate horizontal and vertical vector components, and the force F$_7$ has a relatively large horizontal component and a relatively small vertical vector component. Region D, which joins the parts of the right panel 706B (i.e., a region where the front segment 715 and the bottom segment 717 of the framework 710B$_f$ are connected to the straps 702B, 704B) upon which forces F$_5$, F$_7$ promotes the creation of a resultant force vector F$_6$ that comprises a smaller vertical vector component than the vertical vector component of force F$_5$. The resultant force vector F$_6$ acts upon the headgear 700, in use lessening the force exerted on the face under the nose.

As illustrated, each of the non-limiting exemplary patient interfaces 200, 600 comprise masks adapted to seal about and channel gases to the nose and mouth of a user. In other configurations, the patient interfaces 200, 600 may comprise semi-sealing or non-sealing interfaces. In other configurations the patient interfaces 200, 600 may comprise oral masks, oro-nasal masks, full face masks, nasal pillows masks, endotracheal masks or tubes, combinations of the above, or other gas conveying systems. Certain features, aspects and advantages of the disclosure made with reference to the illustrated patient interfaces may be equally applicable to other interfaces.

A non-limiting headgear assembly 1500 is disclosed in FIGS. 14-30. The headgear assembly 1500 retains the patient interface 1502 at a position on the head of the user such that a seal is formed between the patient interface 1502 and the face of the user. The headgear assembly 1500 is substantially symmetrical and includes right and left ear loops 1510A, 1510B, over-head or crown straps 1520A, 1520B, upper straps 1530A, 1530B, lower straps 1532A, 1532B, and a back panel 1540. In the illustrated configuration, the ear loops 1510A, 1510B, the crown straps 1520A, 1520B, the upper straps 1530A, 1530B, the lower straps 1532A, 1532B, and the back panel 1540 are integrally formed or in the form of a single continuous piece. Alternatively, in some configurations, each respective right and left ear loop, crown strap, upper strap, and lower strap may be integrally formed into individual right and left unitary portions, which may then be joined together by the back panel to form a fully assembled headgear assembly. Further, in some configurations, the headgear assembly 1500 could be formed by separately attaching together the ear loops, crown straps, upper straps, lower straps, and back panel. As will be discussed in greater detail below, the various components of the headgear assembly 1500 may be formed from a variety of materials, including but not limited to polyethylene, polypropylene, fabrics, foams, and fabric/foam composites, such as BREATH-O-PRENE™. In other configurations, the headgear assembly 1500 may be assembled using other means, including but not limited to general overlap or butt welding techniques, ultrasonic welding, high frequency welding, adhesives, stitching, and other mechanical fastening arrangements.

Ear Loops

Referring to FIG. 14, the right and left ear loops 1510A, 1510B are fully joined in a loop and have a substantially rigid structure throughout the loop. In other words, the ear loops 1510A, 1510B retain their shape in the absence of an applied force that is greater than a predetermined amount. Accordingly, when the headgear assembly 1500 is not worn by the user, the headgear assembly 1500 (or at least the ear loops 1510A, 1510B) may retain its shape without collapsing onto itself. As such, the headgear assembly 1500 will not become tangled when not in use and may be neatly folded when stored.

When the headgear assembly 1500 is donned by the user, the ear loops 1510A, 1510B may elastically deform to conform to the contours of the user's head such that the headgear assembly 1500 may be comfortably worn by the user. That is, preferably the ear loops 1510A, 1510B can deform into or out of a plane of the ear loops 1510A, 1510B or, from the perspective of FIG. 14, into or out of the page. The substantially rigid structure of the headgear may be provided by radio frequency (RF) welding of a fabric overlay around a framework or skeleton. The framework provides support and the fabric overlay provides comfort. However, the headgear structure is not limited to specific materials or manufacturing techniques. The framework or skeleton may be constructed from materials having different levels of rigidity, elasticity and/or flexibility such as but not limited to polyethylene and polypropylene. The framework may include cutout portions to provide regions of varying thickness to maintain rigidity of the headgear assembly 1500 while also providing flexibility in certain areas. The fabric overlays may be attached to the frameworks by other means, including but not limited to adhesives, stitching, ultrasonic welding, overmoulding, overlap or butt welding techniques, or mechanical fastening arrangements. The fabric overlays may be constructed from materials having a relatively high compressibility, flexibility, elasticity, breathability and/or softness (e.g., relative to the materials used for the frameworks), such as but not limited to microfibre, unbroken loop (UBL) fabrics, textiles, cloth, and plastics.

Figure 15:
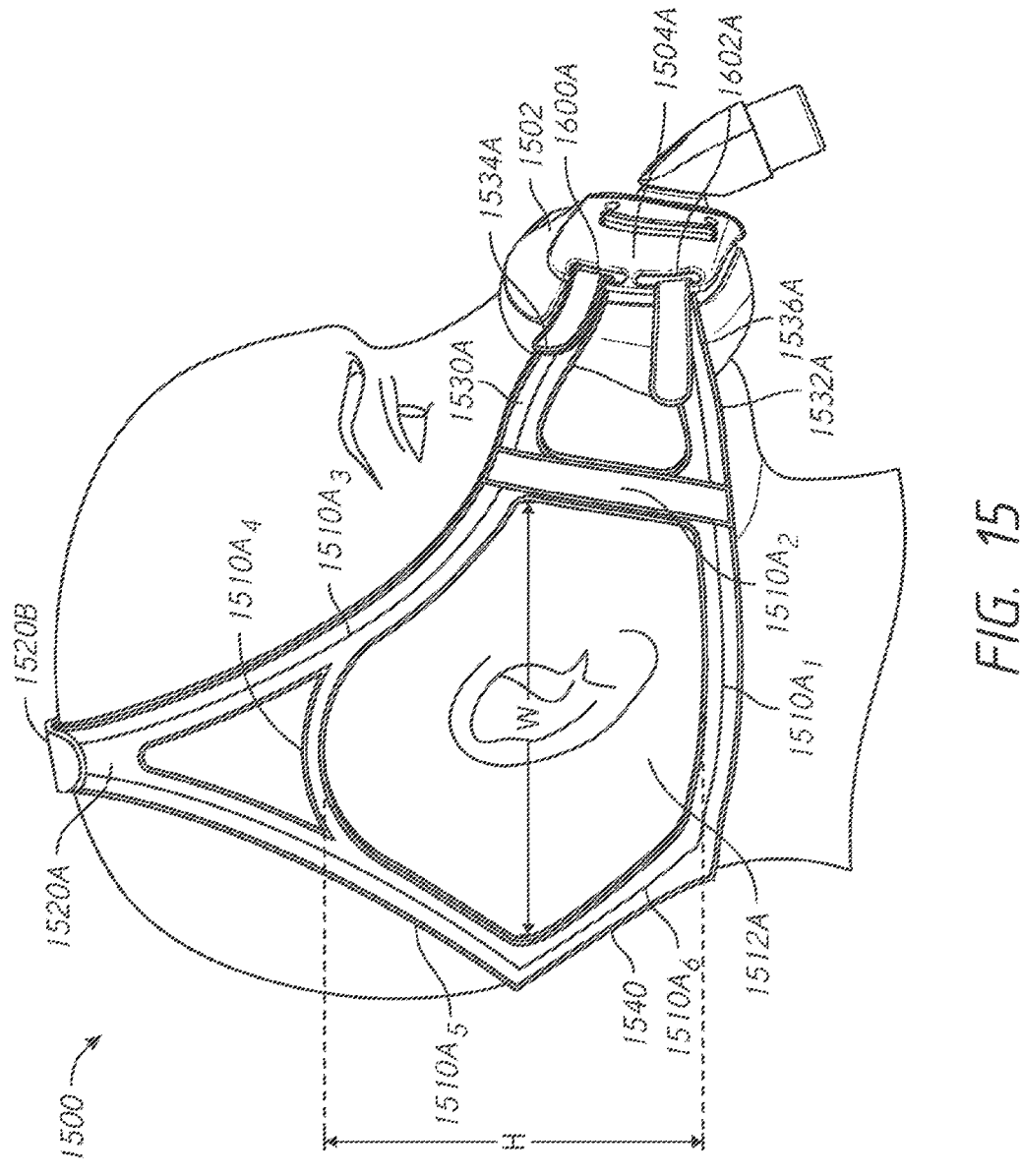
FIG. 15 shows a right plan view of the headgear assembly of FIG. 14.
Figure 16:
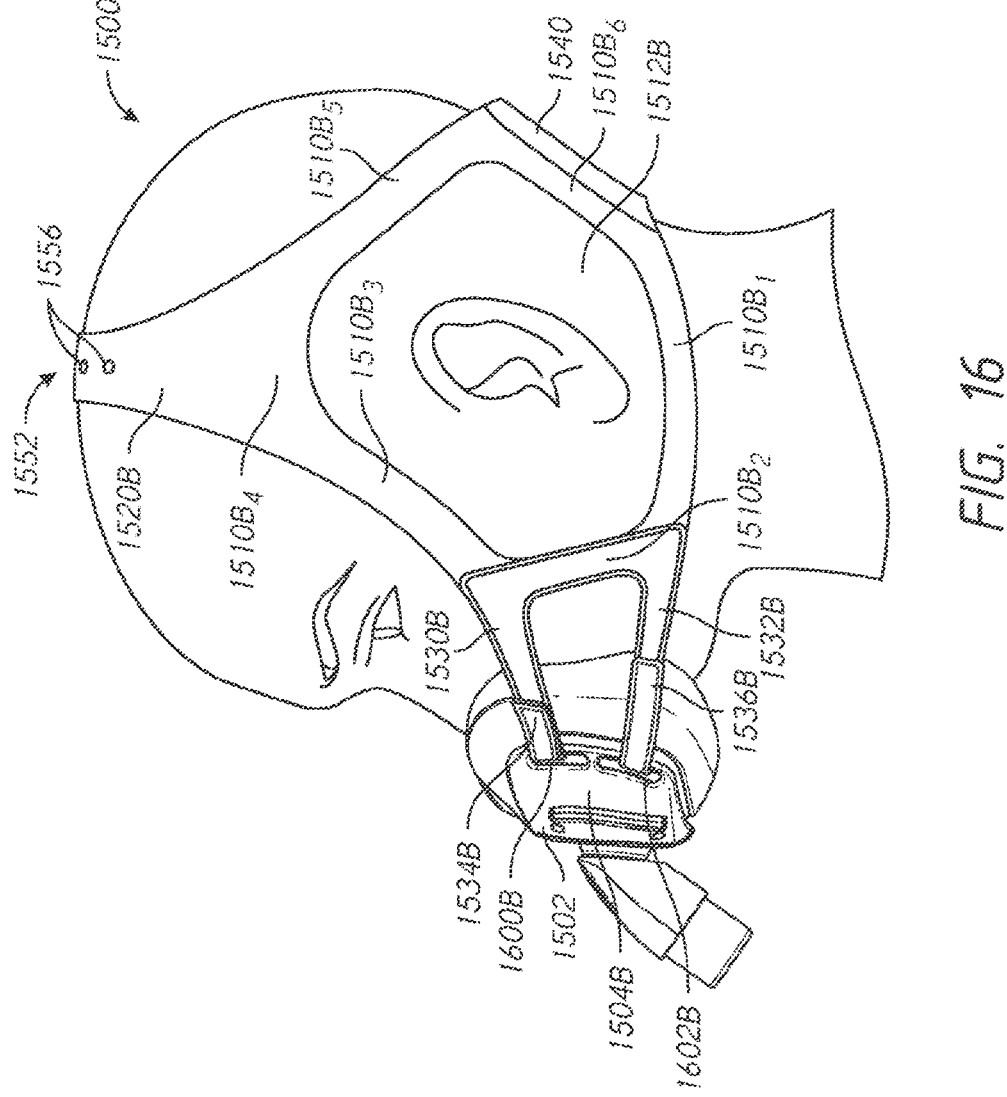
FIG. 16 shows a left plan view of the headgear assembly of FIG. 14.

As illustrated in FIG. 14, the right and left ear loops 1510A, 1510B are symmetrical. As such, the following disclosure will focus on the right ear loop 1510A. The ear loop 1510A is hexagonal in shape and defines an aperture 1512A positioned at its center. When the headgear assembly 1500 is donned by the user, as shown in FIGS. 15 and 16, the ear loop 1510A is positioned on the side of the user's head with the user's ears positioned within the aperture 1512A (for example and not limited to, positioned over the temporalis, auricularis anterior, auricularis superior, auricularis posterior and/or sternocleidomastoid). Preferably, the user's ear is positioned near the center of the aperture 1512A and the ear loop 1510A is positioned a distance away from the user's eyes.

The ear loop 1510A is comprised of segments 1510A_1, 1510A_2, 1510A_3, 1510A_4, 1510A_5, 1510A_6, which are joined together in a hexagonal-like shape to define the aperture 1512A. Similarly, the ear loop 1510B is comprised of segments 1510B_1, 1510B_2, 1510B_3, 1510B_4, 1510B_5, 1510B_6, which are joined together in a hexagonal-like shape to define the aperture 1512B. As shown in FIG. 15, the aperture 1512A may have a height H that is defined between segments 1510A_1, 1510A_4 and a width W defined between the junctions of segments 1510A_2, 1510A_3 and segments 1510A_5, 1510A_6. The width W of the aperture 1512A affects fore-and-aft adjustability of the headgear assembly 1500. The height H affects the vertical adjustability of the headgear assembly 1500. Preferably, the width W and the height H are sized to provide a wide range of adjustability while ensuring that the patient interface 1502 is sufficiently supported by the headgear assembly 1500 and the ear loop 1510A is positioned a comfortable distance from the user's eyes and ears.

Figure 17:
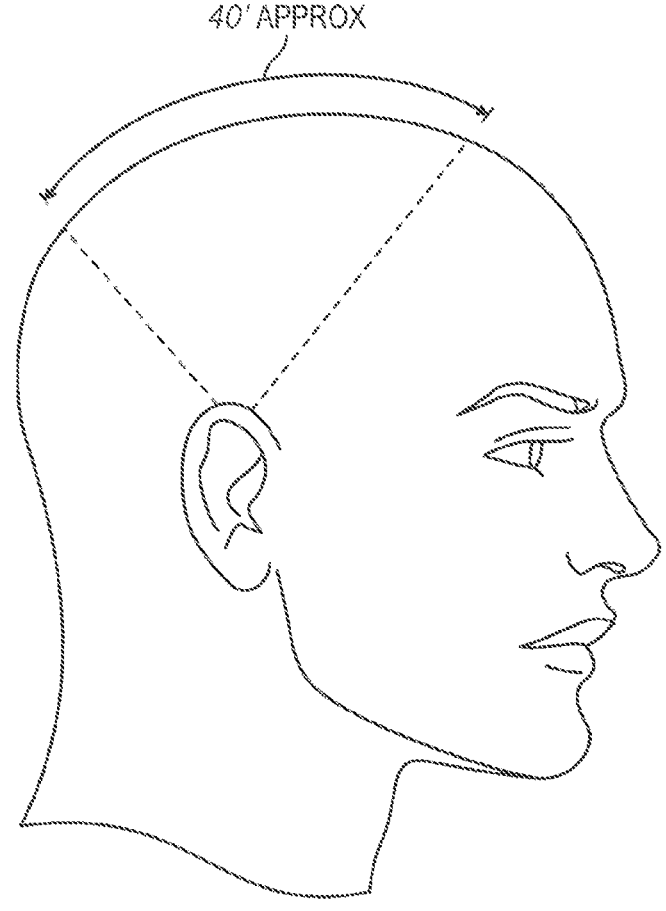
FIG. 17 shows a right plan view illustrating a range of crown strap positions provided by the headgear assembly of FIG. 14.
Figure 18:
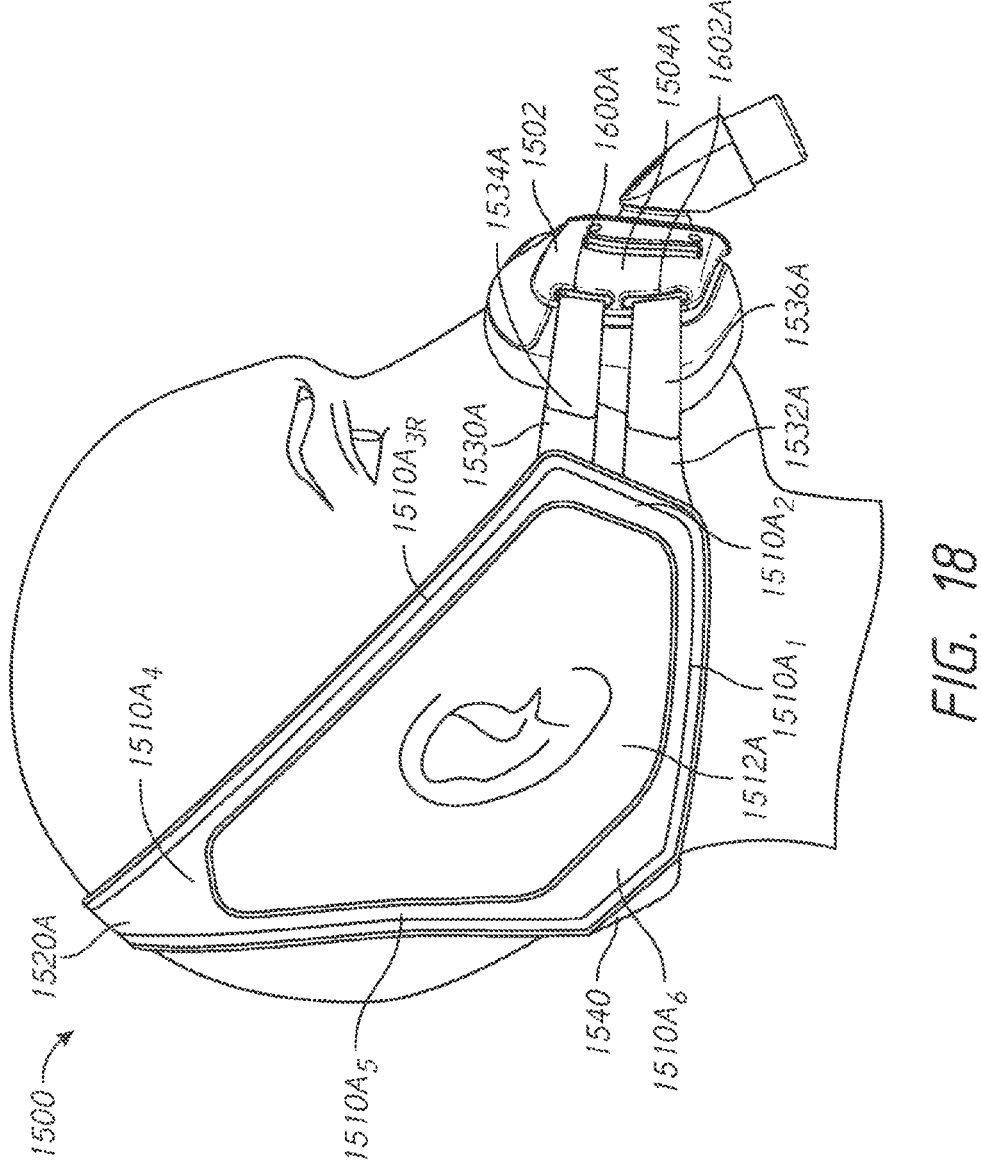
FIG. 18 shows a right plan view of the crown strap positioned at a relative rearward position.
Figure 19:
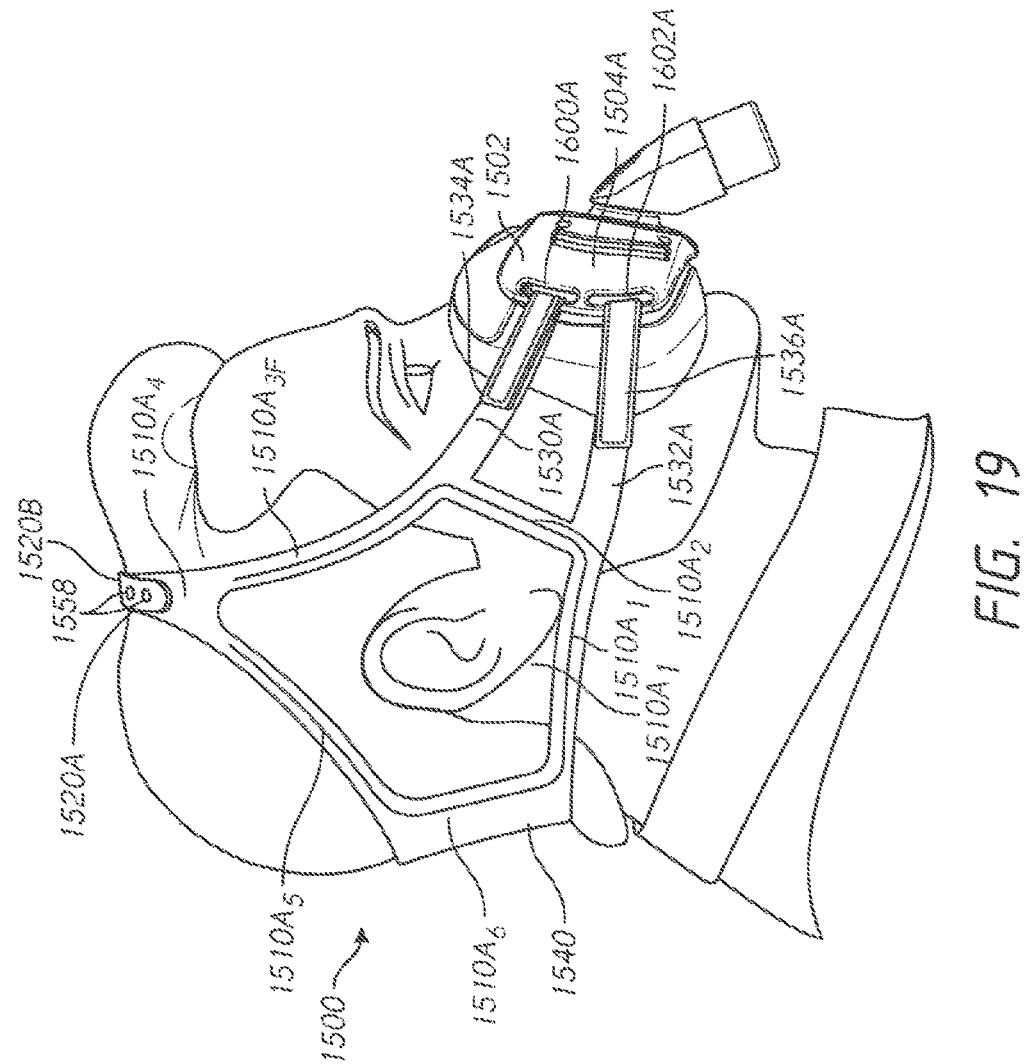
FIG. 19 shows a right plan view of the crown strap positioned at a relative forward position.

The range of adjustability provided by the width W and height H of the headgear assembly 1500 is illustrated in FIG. 17. The crown strap 1520A can be positioned on the head in a wide array of positions, either as a result of user positioning of the associated headgear assembly 1500 on the head or as a result of the construction of the headgear assembly 1500, or both. That is, the crown strap 1520A is not required to be positioned immediately above the ear at a front-to-rear midpoint of the user's head. As shown, in some configurations, the crown strap 1520A rests on the parietal bone of the user and has approximately a 40 degree range of adjustability with respect to the ear. Differing fore-and-aft positions of the crown strap 1530A and headgear assembly 1500 are illustrated in FIGS. 18 and 19. FIG. 18 illustrates a relative rearward position of the crown strap 1530A and FIG. 19 illustrates a relative forward position of the crown strap 1530A. In some configurations, the positions illustrated in FIGS. 18 and 19 can be maximum rearward and forward positions, respectively.

The segment 1510A_1 defines the lowermost portion of the ear loop 1510A. The segment 1510A_1 is substantially straight and, when the headgear is donned by the user, the segment 1510A_1 is positioned below the user's ear and extends substantially horizontally in line with or adjacent to the user's lower jaw from an area near the back of the head and above the user's neck. A portion of the segment 1510A_1 may also be positioned under the user's earlobe such that the user's earlobe overlaps a portion of the segment 1510A_1.

The segment 1510A_2 is connected to segment 1510A_1 and extends substantially vertically with respect to the segment 1510A_1 (for example and not limited to, extending from the ramus of the mandible to a lower and/or rear portion of the zygomatic bone). The segment 1510A_2 is substantially straight and, preferably, has a length of approximately 55.28 mm. The upper and lower straps 1530A, 1532A are connected to the ear loop 1510A at the junctions of the segments 1510A_1, 1510A_2 and segments 1510A_2 and 1510A_3, respectively. Accordingly, in the illustrated configuration, the upper and lower straps 1530A, 1532A are spaced a distance apart by the segment 1510A_2.

The segment 1510A_3 is connected to the segment 1510A_2 and extends upward and rearward towards the top of the head (for example and not limited to, extending from a lower and/or rear portion of the zygomatic bone to the superior line of the parietal bone). The segment 1510A_3 is connected to the crown strap 1520A at the junction of the segments 1510A_3 and 1510A_4. In some configurations, the segment 1510A_3 has a continuously curved conic arc shape such that the segment 1510A_3 is tangent to the crown strap 1520A. As will be discussed in further detail below, the amount of curvature of the segment 1510A_3 may depend upon an angle between of the upper strap 1530A with respect to the crown strap 1520A. The length of the segment 1510A_3 may vary according to the position of the crown strap 1520A on the user's head. For illustration, in FIGS. 18 and 19 which illustrate the relative or maximum forward and rearward positions of the crown strap 1530A provided by the headgear assembly 1500, the segment 1510A_{3R} in FIG. 18 has a greater length than the segment 1510A_{3F} in FIG. 19.

The segment 1510A_4 is connected to the segment 1510A_3. A bottom portion of the crown strap 1530A may be defined by and/or unitary with the segment 1510A_4 such that the crown strap 1530 A is connected to the ear loop 1510A and extends upwards towards the adjoining crown strap 1530B. The segment 1510A_4 can be substantially straight and can extend rearward (for example and not limited to, extending along the superior line of the parietal bone) but may also have a continuously curved conic arc shape that is substantially tangent to the segments 1510A_3 and 1510A_5.

The segment 1510A_5 is connected to the segment 1510A_4. The segment 1510A_5 extends down and rearward towards the neck and back of the user's head (for example and not limited to, extending from the superior line of the parietal bone to the occipital bone). The segment 1510A_5 is connected to the crown strap 1520A at the junction of the segments 1510A_4 and 1510A_5. The segment 1510A_5 is substantially straight but may also have a curved conic arc shape that is tangent to the crown strap 1520A.

The segment 1510A_6 is connected to the segment 1510A_5. The segment 1510A_6 is a substantially straight segment that extends downward along the base of the skull above the neck of the user (for example and not limited to, extending along the occipital bone).

Back Panel

Figure 20:
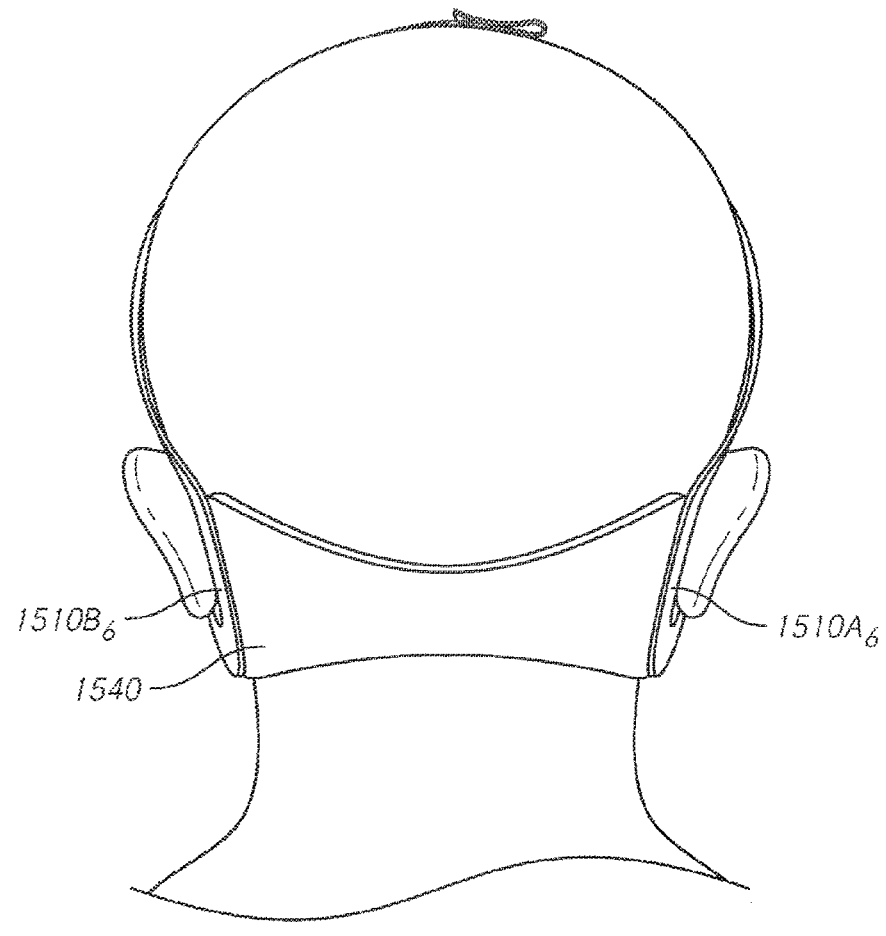
FIG. 20 shows a rear plan view of the headgear assembly of FIG. 14.

As illustrated in FIG. 20, the back panel 1540 is connected to the segment 1510A_6 such that a width of at least end portions of the back panel 1540 is generally defined by the segment 1510A_6. The back panel 1540 is constructed to provide a soft and pillow-like structure positioned at the back of the user's head. In some configurations, the back panel 1540 may be a laminate structure constructed from multiple layers of foam stacked or laminated together and covered with a fabric outer portion. For example, the back panel 1540 may be constructed from one or more layers of spacer fabric material that are individually stacked on top of each other. Similarly, the back panel 1540 may be constructed from a single portion of spacer fabric that is folded over itself multiple times and then stitched or welded together.

The back panel 1540 is adapted to rest above the neck and only bears against the base of the skull (for example, over the occipital portion of the skull). The width of the back panel is lower at or around the middle of the back panel than at the edges. In some configurations, the bottom edge of the back panel 1540 (i.e., the edge of the back panel 1540 that is closest to the neck) may be curved and contoured to follow the shape of the skull and limit or prevent contact of the back panel 1540 with the top of the neck and base of the skull, which improves the comfort of the headgear assembly 1500. Further, in some configurations, the back panel 1540 may include a hole positioned at the center of the back panel 1540 such that the occipital portion of the skull is positioned within the hole. The back panel 1540 may be constructed from a flexible, stretchable, and breathable material such as, but not limited to, BREATH-O-PRENE™.

Crown Strap

In the illustrated configuration in FIGS. 14 to 16, the crown straps 1520A, 1520B are integrally formed with the ear loops 1510A, 1510B and extend upward toward the top of the user's head from the segments 1510A$_4$, 1510B$_4$. The crown straps 1520A, 1520B are substantially equal in length and, preferably, have a length that varies depending on the size (i.e., small, medium, large, etc.) of the headgear assembly 1500. Similar to the ear loops 1510A, 1510B, the crown straps 1520A, 1520B have a substantially rigid structure that is neither fully rigid nor flexible and may be similarly constructed by welding a fabric overlay around a framework or skeleton. Thus, from the perspective of FIG. 14, preferably the crown straps 1520A, 1520B can deform into or out of the page. The crown straps 1520A, 1520B may be unitary and formed as a single piece with the ear loops 1510A, 1510B and/or the straps 1530A, 1532A. Alternatively, the crown straps 1520A, 1520B may be separate pieces that are attached to the ear loops 1510A, 1510B.

Figure 21:
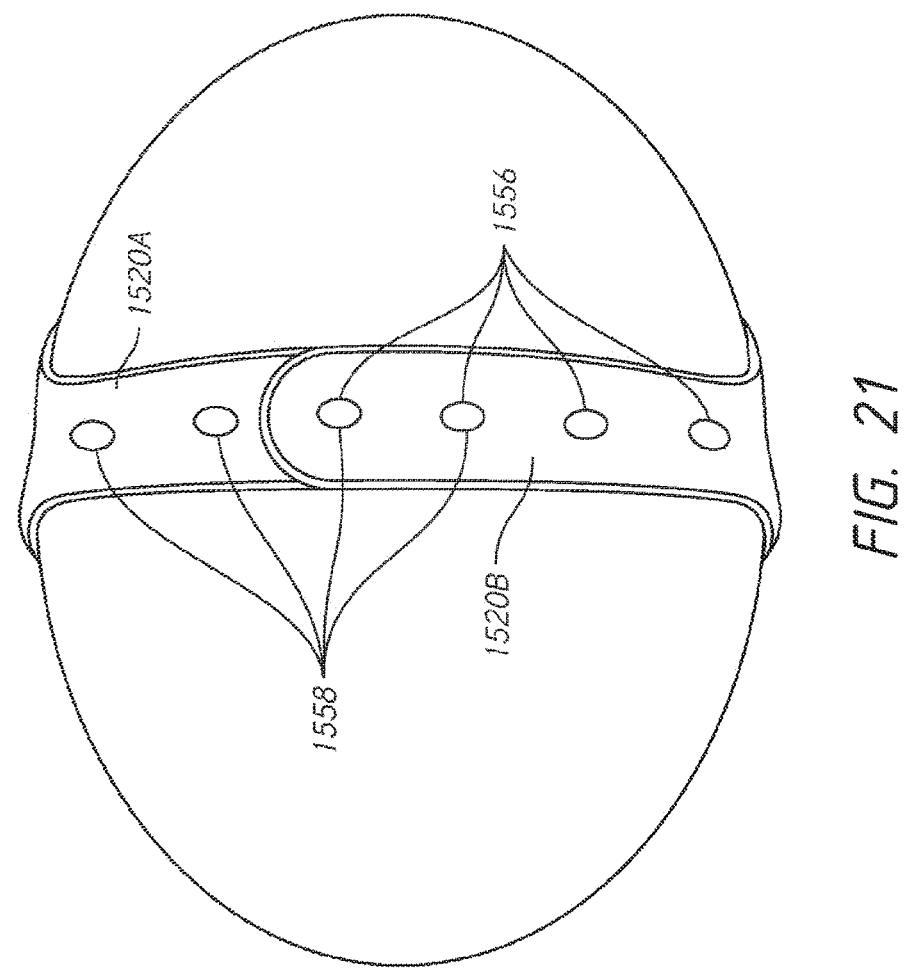
FIG. 21 shows a top plan view of the headgear assembly of FIG. 14.

As illustrated in FIG. 21, the right crown strap 1520A is removably fastened to the left crown strap 1520B via fasteners 1550. The fasteners 1550 may be interference-fit or "baseball cap type" snapback fasteners 1550 to provide easy to use, discrete and incremental adjustment of the combined length of the crown straps 1520A, 1520B. The fasteners 1550 are comprised of female elements 1552 and male elements 1554. The female elements 1552 comprise ovular through-holes 1556 that extend substantially through the full thickness of the left crown strap 1520A in a direction perpendicular to the length of the left crown strap 1520B. The male elements 1554 comprise of an outward protrusion 1558 extending substantially perpendicular to a surface of the right crown strap 1520A. The male elements 1554 have a corresponding size and ovular shape with the female elements 1552 to provide a friction or interference fit. The protrusion 1558 of the male elements 1554 extends a height above the surface of the right crown strap 1520A that is substantially equal to the thickness of the right crown strap 1520A such that the ends of the male elements 1554 are substantially flush with the surface of the right crown strap 1520A when the male elements 1554 are inserted into female elements 1552. The male elements 1554 may be integrally molded into the framework of the right crown strap 1520A and protrude through the overlay. The major axis of the ovular shaped female and male elements 1552, 1554 is aligned with the lengthwise direction of the crown straps 1520A, 1520B to prevent the female and male elements 1552, 1554 from prematurely and unintentionally separating due to the curvature of the crown straps 1520A, 1520B when the headgear assembly 1500 is worn by the user. The female and male elements 1552, 1554 are not limited to holes 1556 and protrusions 1558 having an ovular shape and may have a shape that includes round and/or a combination of shapes to provide secure mechanical attachment. Further, the positioning of female elements 1552 and male elements 1554 may be reversed on the right and left crown straps 1520A, 1520B.

The crown straps 1520A, 1520B are removably fastened together by overlapping the right crown strap 1520A over the left crown strap 1520B, aligning the male elements 1554 with the female elements 1552, and inserting the male elements 1554 into the female elements 1510. The interference fit between the male and female elements 1552, 1554 further inhibits or prevents the right crown strap 1520A from prematurely and unintentionally detaching from the right crown strap 1520A. The female elements 1554 are positioned on the right crown strap 1520A and positioned at equidistant intervals apart. Similarly, the male elements 1554 are positioned on the right crown strap 1520A and positioned at identical equidistant intervals as the female elements 1554. Preferably, the female and male elements 1552, 1554 are each positioned at intervals of 23.5 mm. In the illustrated configuration, the right crown strap 1520A is depicted as having four female elements which provides the user with just four discrete and incremental positions from which the user may select. Accordingly, the user may quickly determine and select the correct size of the crown straps 1520A, 1520B. The crown straps 1520A, 1520B are not limited to four discrete positions and/or specific intervals between each of the female and male elements 1552, 1554.

In operation, the fasteners 1550 inhibit or prevent the user from attempting to adjust both the crown strap and the upper/lower straps at the same time. More specifically, the crown straps 1520A, 1520B with the fasteners 1550 require or at least encourage the user to first adjust the "tightness" or length of the crown straps 1520A, 1520B and then adjust the fitment of the upper and lower straps 1530A, 1530B, 1532A, 1532B. Accordingly, fastening the fasteners 1550 to adjust the crown straps 1520A, 1520B may require the user to entirely remove the headgear assembly 1500 from the user's head. As such, after the crown straps 1520A, 1520B are properly adjusted and the headgear assembly 1500 is repositioned on the user's head, the user may devote all attention and focus to finely adjusting the upper and lower straps 1530A, 1530B, 1532A, 1532B to ensure precise fitment and proper sealing of the patient interface 1502. Further, as will be discussed in further detail below, the upper straps 1530A, 1530B are angled with respect to the lower straps 1532A, 1532B such that the upper straps 1530A, 1530B provide a slight vertical adjustment of the patient interface 1502. As such, finer and non-incremental vertical adjustments of the patient interface 1502 may be provided by the upper straps 1530A, 1530B while larger incremental vertical adjustments may be provided by the crown straps 1520A, 1520B.

The male elements 1554 may be positioned proximal to an end of the right crown strap 1520B (i.e., further from the ear loop 1510B) such that the male elements 1554 do not extend from the right crown strap 1520B on a side of the user's head (for example and not limited to, extending below the superior temporal line). Limiting the positioning of the male elements 1554 to the top portion of the headgear assembly 1500 ensures that the male elements 1554 are not in a position to create pressure points against the user's head if, for example, the user's head is turned and the male elements 1554 are sandwiched between the user's head and a pillow.

Upper and Lower Straps

The upper and lower straps 1530A, 1532A, 1530B, 1532B are soft and flexible straps that are connected to and extend from the ear loops 1510A, 1510B. The upper and lower straps 1530A, 1532A, 1530B, 1532B have ends 1534A, 1534B, 1536A, 1536B which are inserted into upper and lower slots 1600A, 1600B, 1602A, 1602B of headgear connectors 1504A, 1504B of the patient interface 1502. The ends 1534A, 1534B, 1536A, 1536B may be looped upon themselves and secured such that the patient interface 1502 may be removably fastened to the headgear assembly 1500 and retained against the user's face. The straps 1530A, 1530B, 1532A, 1532B are symmetrical from left-to-right and, therefore, the following disclosure will focus on the right upper and lower straps 1530A, 1532A. The straps 1530A, 1532A have a flexible structure and may be formed together or separately as an overlay that is separately attached to the ear loop 1510A. Alternatively, one or both of the straps 1530A, 1532A may be unitary and formed as a single piece with the ear loops 1510A, 1510B, the crown straps 1520A, 1520B and/or the back panel 1540. The lengths of the straps 1530A, 1532A may vary depending on the size (i.e., small, medium, large, etc.) of the headgear assembly 1500.

Figure 22:
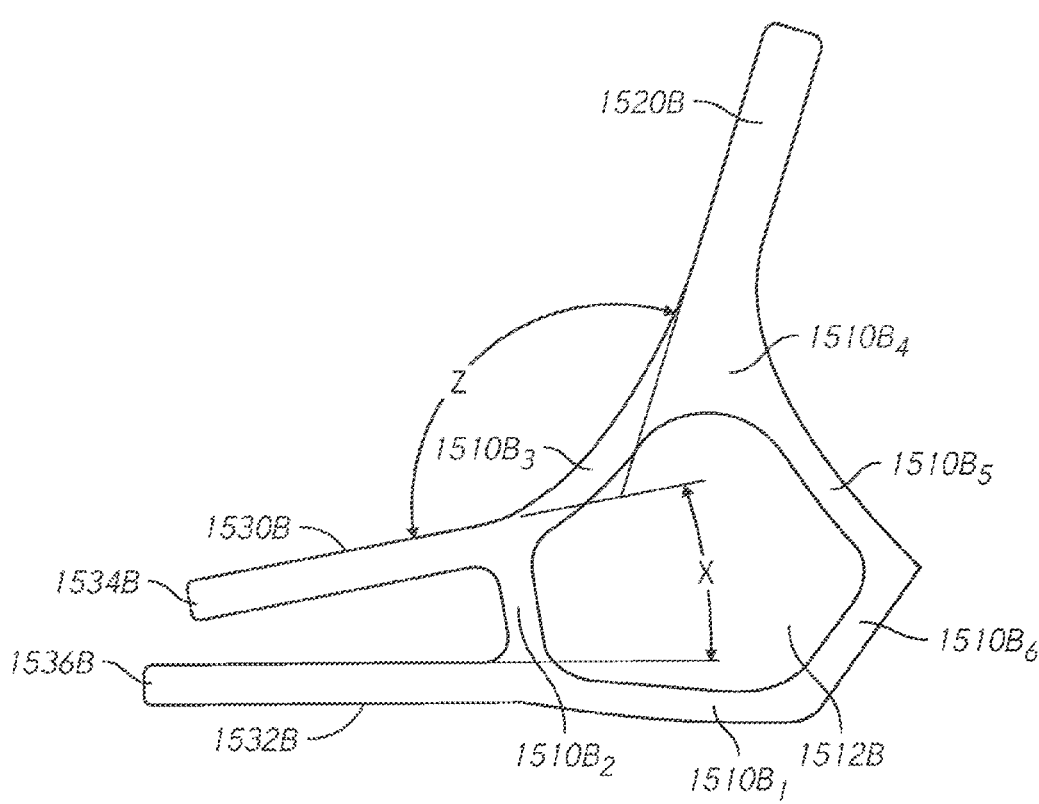
FIG. 22 shows a left plan view of an assembly including an ear loop, a crown strap, an upper strap and a lower strap.

In the illustrated configuration of FIG. 22, the lower strap 1532A extends from the ear loop 1510A at the junction of segment 1510A₁ and 1510A₂. When the headgear assembly 1500 is worn by the user, the lower strap 1532A extends horizontally along the jaw of the user (for example and not limited to, extending from the ramus of the mandible to the mental foramen) until entering the slot 1602A of the patient interface 1502. As a result, the lower strap 1532A exerts a horizontal force vector on the patient interface 1502 to retain the patient interface 1502 on the user's face. The upper strap 1530A extends from the ear loop 1510A at the junction of segment 1510A₂ and 1510A₃. When the headgear assembly 1500 is worn by the user, the upper strap 1530A extends along the cheekbone of the user (for example and not limited to, extending along the zygomatic arch of the zygomatic bone) until entering the upper slot 1600A of the patient interface 1502. The upper strap 1530A may be angled downward towards the lower strap 1532A in a direction towards the patient interface 1502. Put another way, the upper strap 1530A is angled away from the lower strap 1532A in a direction from the end 1534A of the upper strap 1530A towards the ear loop 1510A. Accordingly, the upper strap 1530A exerts both a horizontal force vector and a vertical force vector to retain the patient interface 1502 against the user's face and/or seal with the nares of the user's nose. As such, the upper strap 1530 provides the user with a finer degree or smaller amount of non-incremental vertical adjustment than the broad incremental amounts of vertical adjustment provided by the crown straps 1520A, 1520B. Therefore, the broad incremental adjustment provided by the "baseball cap type" snapback fasteners 1550 of the crown straps 1520A, 1520B may be first used to adjust the general vertical position the patient interface 1502 on the user's face. After adjusting the crown straps 1520A, 1520B, smaller and finer non-incremental vertical adjustments to the patient interface 1502 may be provided by the upper straps 1530A, 1530B. It should be noted that a headgear having upper and lower straps that are horizontal to the user preferably would not be combined with crown straps that only provide incremental adjustment because such crown straps, alone, would lack the ability to add smaller and finer non-incremental vertical adjustments to the patient interface 1502. In other words, if both the upper and lower straps 1530A, 1530B, 1532A, 1532B are horizontal to the user's face, finer non-incremental vertical adjustments may not be possible by adjusting the crown straps 1520A, 1520B. Thus, preferably, a headgear provided with horizontal upper and lower straps would also provide fine adjustment of the crown or other over-head strap(s).

Figure 23:
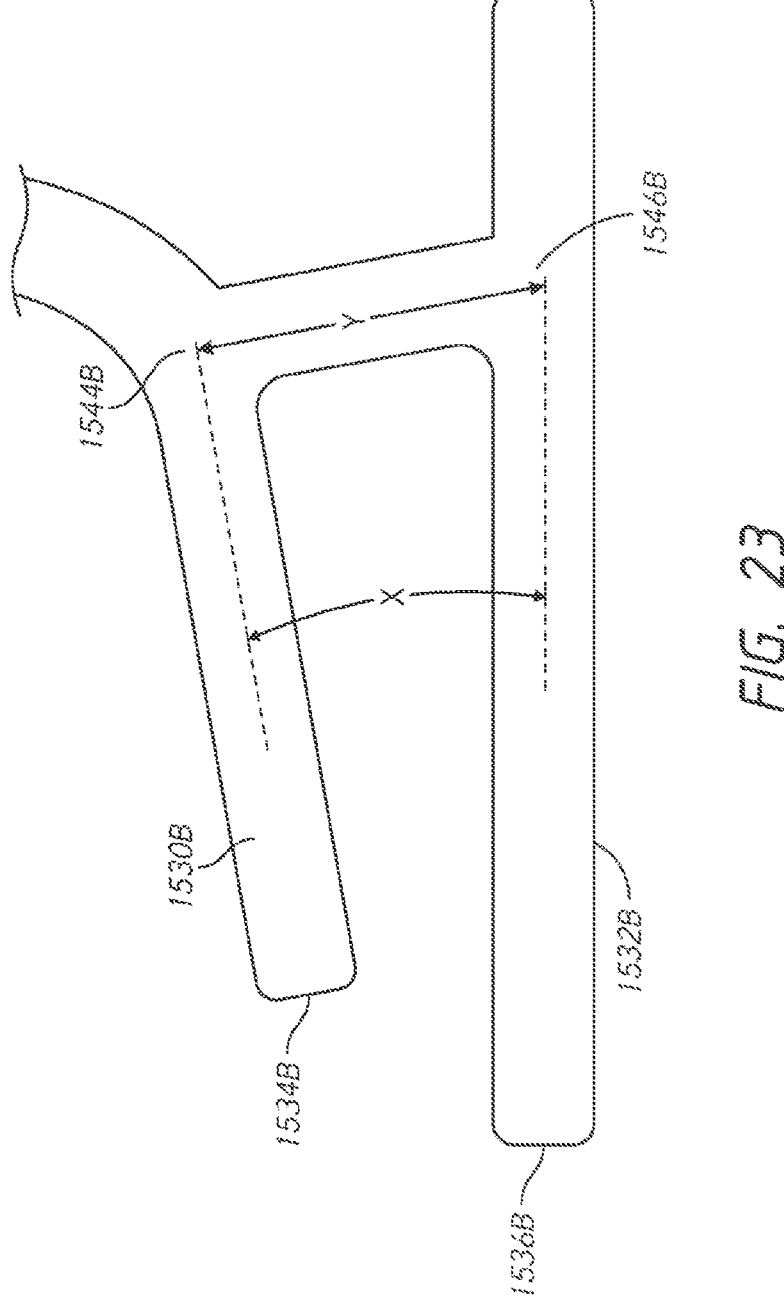
FIG. 23 shows a close-up view of the ear loop, upper strap and lower strap.

As shown in FIG. 23, an upper/lower strap angle X is defined between the lengthwise directions of the upper and lower straps 1530A, 1532A. The upper strap 1530A extends away from the lower strap 1532A in a direction from the end 1534A of the upper strap 1530A towards the ear loop 1510A. In the illustrated configuration, the upper/lower strap angle X may be equal to 12 degrees but may be within a range of 0 to 25 degrees. Smaller angles may cause limited vertical adjustability and vertical stability while larger angles may position portions of the ear loop 1510A uncomfortably close to the user's eyes.

Figure 24:
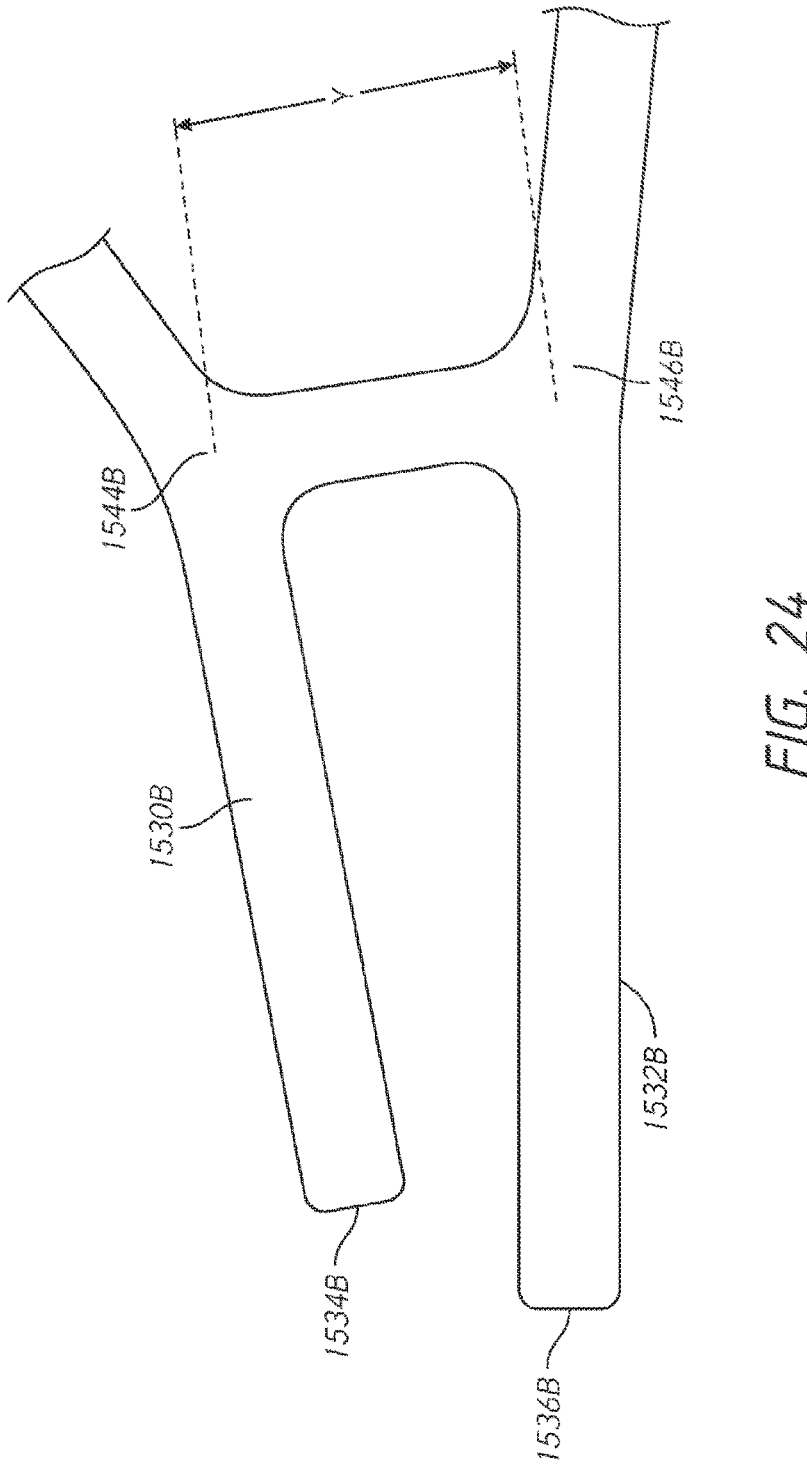
FIG. 24 shows a close-up view of the ear loop, upper strap and lower strap.

Referring to FIGS. 23 and 24, the upper strap 1530A and the lower strap 1532A may be separated by an upper/lower strap distance Y, which is defined as the distance between upper strap 1530A and the lower strap 1532A. More specifically, Y is the distance between the centers of the upper and lower straps 1530A, 1532A at the upper strap connection points 1544A, 1544B and the lower strap connection points 1546A, 1546B. Preferably, the upper/lower strap distance Y is equal to 55 mm but may be within a range of, for example, 35 to 65 mm depending on the size (i.e., small, medium, large, etc.) of the patient interface 1502 and the mask seal (not shown). Generally, the stability of the patient interface 1502 is affected by the upper/lower strap distance Y. A larger upper/lower strap distance Y may reduce rocking of the patient interface 1502 between the nose and chin. However, the upper/lower strap distance Y may be limited by the size of the headgear connectors 1504A of the patient interface 1502. That is, a limiting factor of the upper/lower strap distance Y may be the position of the upper and lower slots 1600A, 1602A of the headgear connectors 1504A with respect to the upper and lower straps 1530A, 1532A when the straps 1530A, 1532A and are patient interface 1502 adjusted to their tightest setting.

As illustrated in FIG. 22, an upper/crown strap angle Z is defined between the lengthwise directions of the upper strap 1530A and the crown strap 1520A. The upper/crown strap angle Z may be within a range of 100 to 150 degrees and, preferably, equal to 118 degrees. As previously mentioned, in some configurations, the segment 1510A₃ has a continuously curved conic arc shape such that the segment 1510A₃ is at least tangent to the crown strap 1520A and, in some configurations, tangent to the upper strap 1530A and the crown straps 1520A. The continuously curved conic arc shape of the segment 1510A₃ functions to transfers the under nose sealing force to the crown strap 1520A. As a result, the load exerted on the underside of the user's nose and the underside septum pressure is reduced, which improves user comfort. The upper/crown strap angle Z and the continuously curved conic arc shape of the segment 1510A₃ create a smooth transition between the crown strap 1520A and the upper strap 1530A which allows the headgear assembly 1500 to tautly conform to the contours of the user's head which also improves user comfort. Preferably, the upper/crown strap angle Z is relatively wide (i.e., greater than 100 degrees) to reduce or prevent buckling of the segment 1510A₃ of the headgear assembly 1500 away from the user's head. A narrow upper/crown strap angle Z can result in buckling of the segment 1510A₃ which can cause laxity between the upper strap 1530A and the crown strap 1532A. Laxity allows rocking of the patient interface 1502 between the user's nose and chin which may cause user discomfort and/or compromise the seal between the patient interface 1502 and the user.

As illustrated in FIGS. 15 and 16, the upper and lower straps 1530A, 1532A are secured using the ends 1534A, 1536A, which comprise hook pads or patches that can be secured to complementary loop surfaces, such as UBL fabric, on the upper and lower straps 1530A, 1532A (e.g., in a hook-in-loop style fastening mechanism). The loop surfaces may be added by placing adhesive loop pads on the surfaces of the upper and lower straps 1530A, 1532A. In other configurations, the loop surfaces may be inherent in the material used for the upper and lower straps 1530A, 1532A. Other suitable fasteners could also be used.

Figure 25:
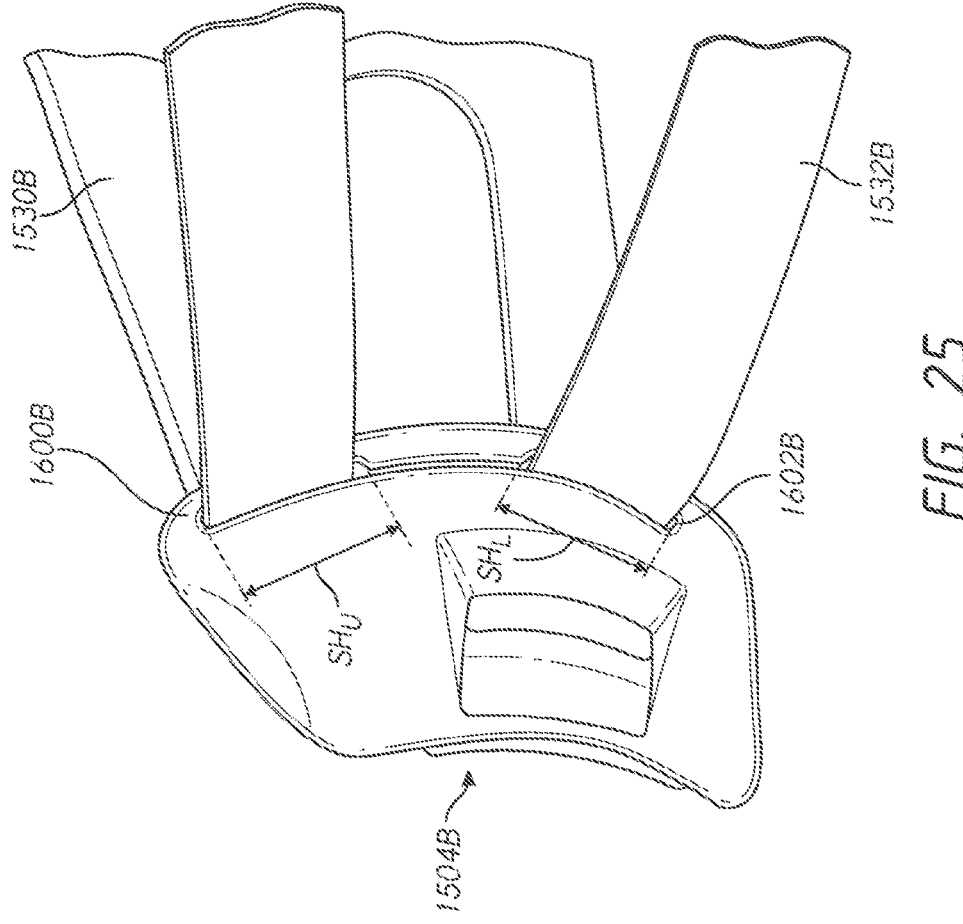
FIG. 25 shows a left plan view of the upper strap and lower strap connected to a headgear connector of the patient interface.
Figure 26:
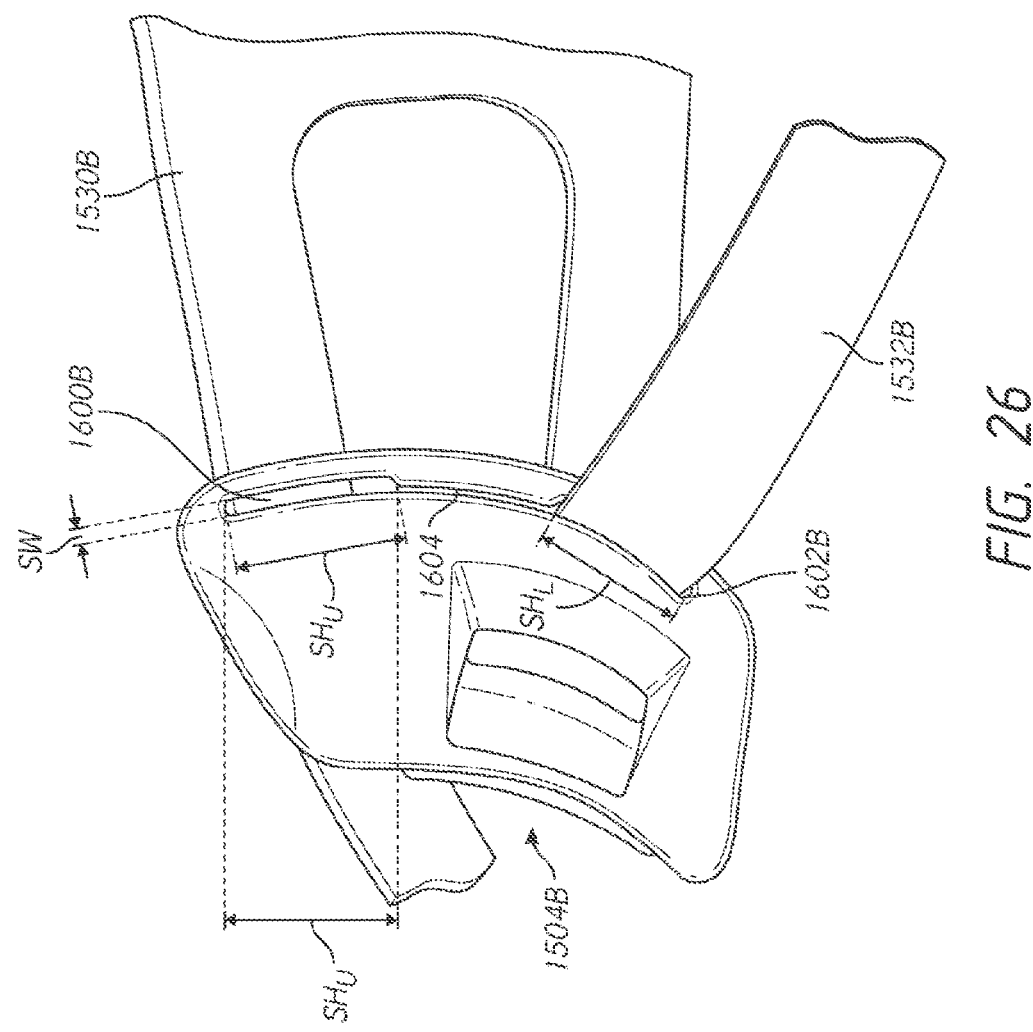
FIG. 26 shows a left plan view of the lower strap connected to the headgear connector of the patient interface. The upper strap is removed to illustrate a connection slot of the headgear connector.

The upper strap 1530A is received by the upper slot 1600A and the lower strap is received by the lower slot 1602A. As illustrated in FIGS. 25 and 26, the upper and lower slots 1600A, 1600B may have slot heights $SH_L$, $SH_U$ that are substantially similar in size to the width of the upper and lower straps 1530A, 1530B. The slot height $SH_U$ of the upper slot 1600A is greater (i.e., taller and greater in distance) than the slot height $SH_L$ of the lower slot 1602A. The greater slot height $SH_U$ of the upper slot 1600A allows the upper strap 1530A to move upward (i.e., substantially vertically) within the slot 1600A as the strap 1530A is tightened. In contrast to the lower strap 1532A, the upper strap 1530A requires a greater range of vertical adjustment as the upper strap 1530A is tightened to resolve an upward force vector provided by the CPAP blow-off force and resolve any moment acting on the mask seal. Resolving the upward force vector allows the upper strap 1530A to maintain the mask seal in its operable position on the user's face to create a seal under the nose. The lower slot 1602A has a shorter slot height $SH_L$ because the lower strap 1532A does not resolve the vertical force on the mask seal, and only resolves a substantially horizontal force to maintain a seal around the mouth. Therefore, a longer upper slot 1600A allows adjustment and adjusting tightness without compromising the under nose seal.

In some configurations, the upper and lower slots 1600A, 1602A of headgear connector 1504A have a slot width SW that is slightly less than the thickness of the upper and lower straps 1530A, 1532A. The slightly smaller slot width of the slots 1600A, 1602A is configured to create an interference fit between the surfaces of the slots 1600A, 1602A and the upper and lower straps 1530A, 1532A. Preferably, the interference fit generates a frictional force between the slots 1600A, 1600B and the upper and lower straps 1530A, 1532A that is greater than the pressure of the CPAP blow-off force. In other words, movement between the straps and clips only occurs if a force greater than the blow-off force is applied by the patient interface 1502. As such, the upper and lower straps 1530A, 1532A will not loosen (i.e., loss of tension in the straps 1530A, 1532A) and the patient interface 1502 will not be pushed away from the user's face when the straps are unfastened or not secured. Accordingly, the user may make small non-incremental adjustments to the upper and lower straps 1530A, 1532A with a single hand without holding and applying force to the patient interface with the opposite hand to prevent the blow-off force from loosening the upper and lower straps 1530A, 1532A. As a result, the upper and lower straps 1530A, 1532A may remain unfastened and the user may make only small adjustments to the upper and lower straps 1530A, 1532A without risk of the upper and lower straps 1530A, 1532A loosening due to the blow-off force. Thus, adjustments can be made without, or with a reduced risk of, losing the initial adjustment position. The slot width SW may vary according to the geometry and construction of the upper and lower straps 1530A, 1532A. In the illustrated configuration, the slots 1600A, 1602A are connected by a channel 1604A. However, in other configurations, the slots 1600A, 1602A may be mutually exclusive. Further, the slots 1600A, 1602A may be angled relative to each other and substantially parallel to the width-wise directions of the upper and lower straps 1530A, 1532A.

Alternate Configurations

Figure 27:
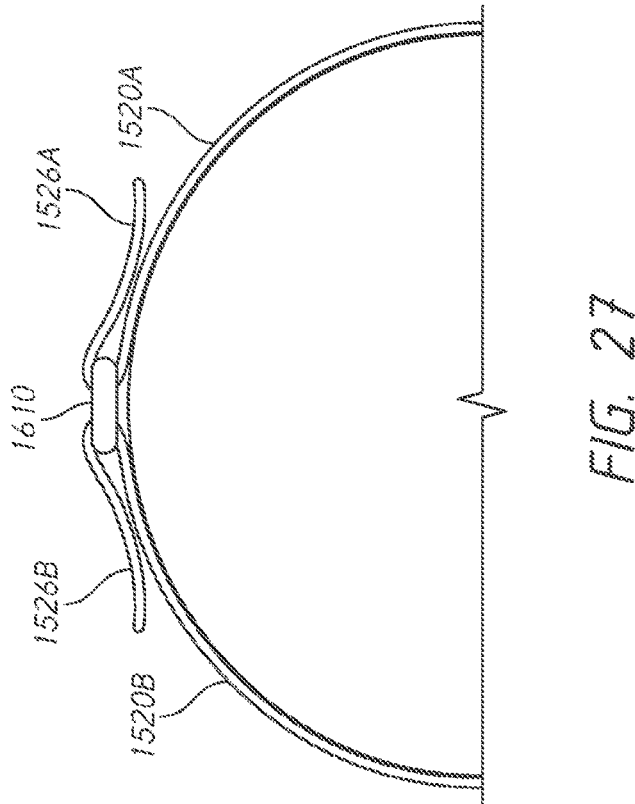
FIG. 27 shows a front plan view of an alternative crown strap attachment arrangement of the present disclosure.

In other configurations, the crown straps 1520A, 1520B may be removably fastened together by a headgear retainer or buckle 1610 (e.g., a strap connector comprising apertures configured to accept the crown straps 1520A, 1520B) to provide infinite adjustment of the crown straps 1520A, 1520B, as shown in FIG. 27. The crown straps 1520A, 1520B are then looped back upon themselves and secured. As shown the crown straps 1520A, 1520B are secured using the crown strap ends 1526A, 1526B, which comprise hook pads or patches that can be secured to complementary loop surfaces on the crown straps 1520A, 1520B (e.g., in a hook-and-loop fastening mechanism). The loop surfaces may be added by securing adhesive loop pads on the surfaces of the crown straps 1520A, 1520B or by selection of a suitable material to function as the loop component.

Figure 28:
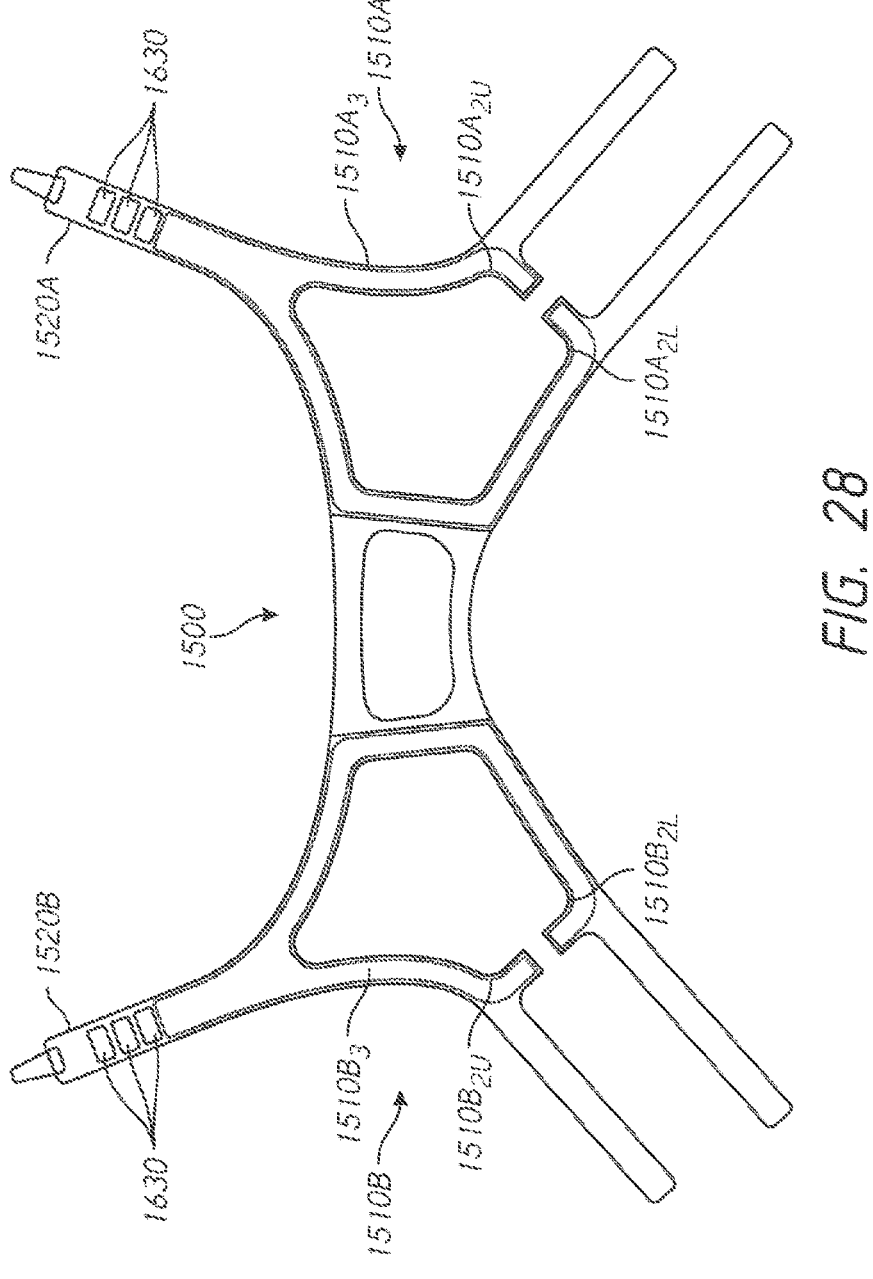
FIG. 28 shows a top view of a headgear assembly according to an alternative embodiment of the present disclosure in a flattened condition.

In other configurations, the crown straps 1520A, 1520B may have rigid incremental spacers 1630 positioned along the length of each crown straps 1520A, 1520B, as illustrated in FIG. 28. The rigid spacers 1630 allow folding of each of the crown straps 1520A, 1520B upon itself or looping over of the crown straps 1520A, 1520B only at positions between the rigid spacers 1630. As such, when the crown straps 1520A, 1520B are fastened together with the headgear retainer 1610 and hook pads, the rigid spacers 1630 allow the crown straps 1520A, 1520B to provide increment length adjustment of the crown straps 1520A, 1520B or vertical adjustment of the ear loops 1510A, 1510B. Further, the rigid spacers 1630 maintain a substantially rigid structure through the crown straps 1520A, 1520B.

In other configurations, the curvature of the segments 1510A$_3$, 1510B$_3$ may transition sharply from the crown straps 1520A, 1520B to ensure that the crown straps 1520A, 1520B and the upper straps 1530A, 1530B are positioned away from the user's eyes, as shown in FIG. 28. Additionally, each of the segments 1510A$_2$, 1510B$_2$ of the ear loops 1510A, 1510B may be divided into separate upper portions 1510A$_{2U}$, 1510B$_{2U}$ and lower portions 1510A$_{2L}$, 1510B$_{2L}$ such that the upper straps 1530A, 1530B and the lower straps 1532A, 1532B are initially disconnected. The respective upper portions 1510A$_{2U}$, 1510B$_{2U}$ and lower portions 1510A$_{2L}$, 1510B$_{2L}$ can be secured to one another by any suitable method to create closed ear loops 151A, 1510B. In some configurations, the upper portions 1510A$_{2U}$, 1510B$_{2U}$ and lower portions 1510A$_{2L}$, 1510B$_{2L}$ are offset from one another in the flattened condition of the headgear assembly 1500. Movement of the upper portions 1510A$_{2U}$, 1510B$_{2U}$ and lower portions 1510A$_{2L}$, 1510B$_{2L}$ towards one another for connection induces a curvature in one or more segments of the ear loops 1510A, 1510B once the upper portions 1510A$_{2U}$, 1510B$_{2U}$ and lower portions 1510A$_{2L}$, 1510B$_{2L}$ are connected. Such an arrangement is one method for creating a non-flat or three-dimensional configuration, such as the above described conic curvature, of at least portions of the ear loops 1510A, 1510B. In other arrangements, the ear loops 1510A, 1510B could define an open loop.

Figure 29:
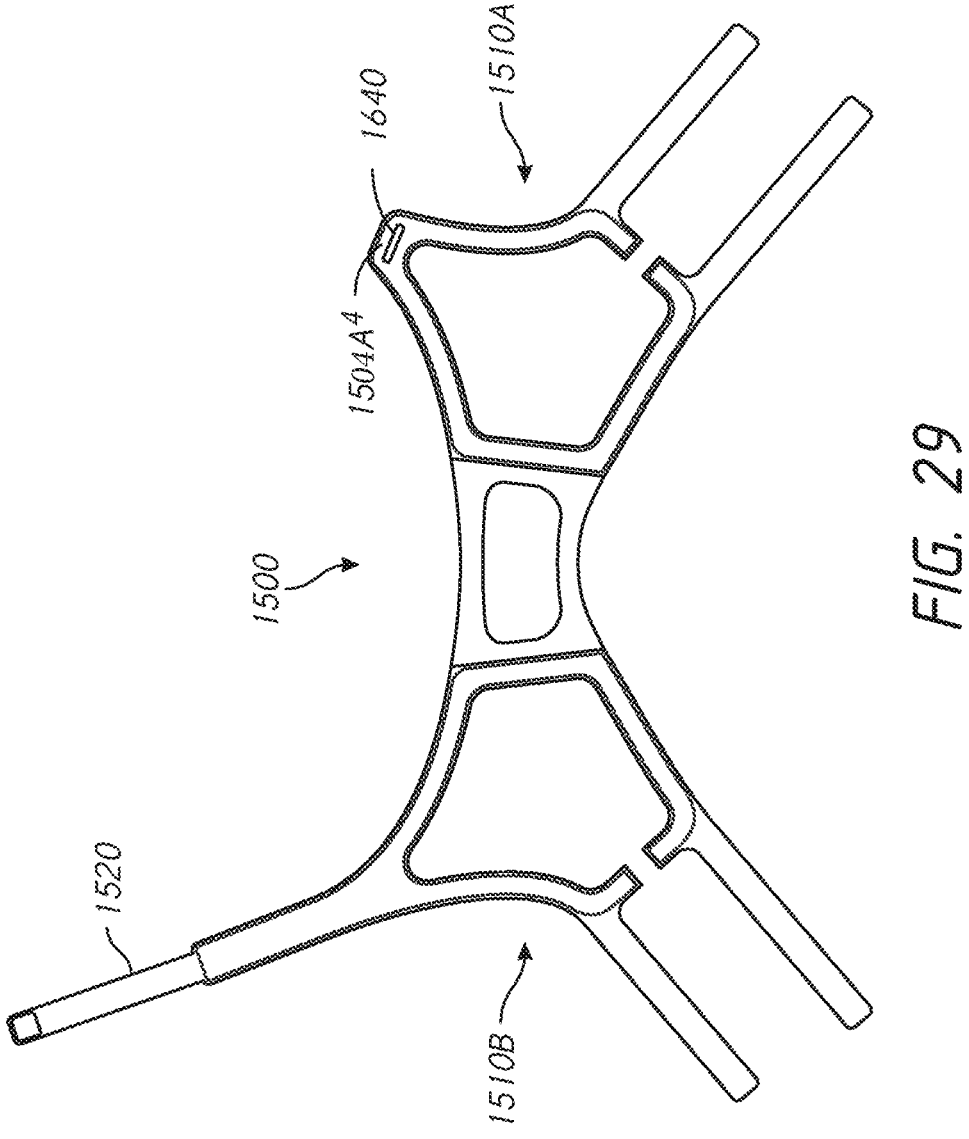
FIG. 29 shows a top view of a headgear assembly according to another alternative embodiment of the present disclosure in a flattened condition.

In other configurations, the headgear assembly 1500 may include a crossover crown strap 1520 extending from one side towards or to the other side. For example, the crown strap 1520 can extend over the head from the ear loop 1510A and be removably fastened directly to the opposite ear loop 1510B. This arrangement could also be reversed. Referring to FIG. 29, the crossover crown strap 1520 extends from the right ear loop 1510A and is removably fastened to an aperture 1640 within the segment 1510A$_4$ of the right ear loop 1510A. The crossover crown strap 1520 is then looped back upon itself and secured. The crossover crown strap 1520 allows the user to make infinite adjustment of the crown portion of the headgear assembly 1500 with a single hand.

Figure 30:
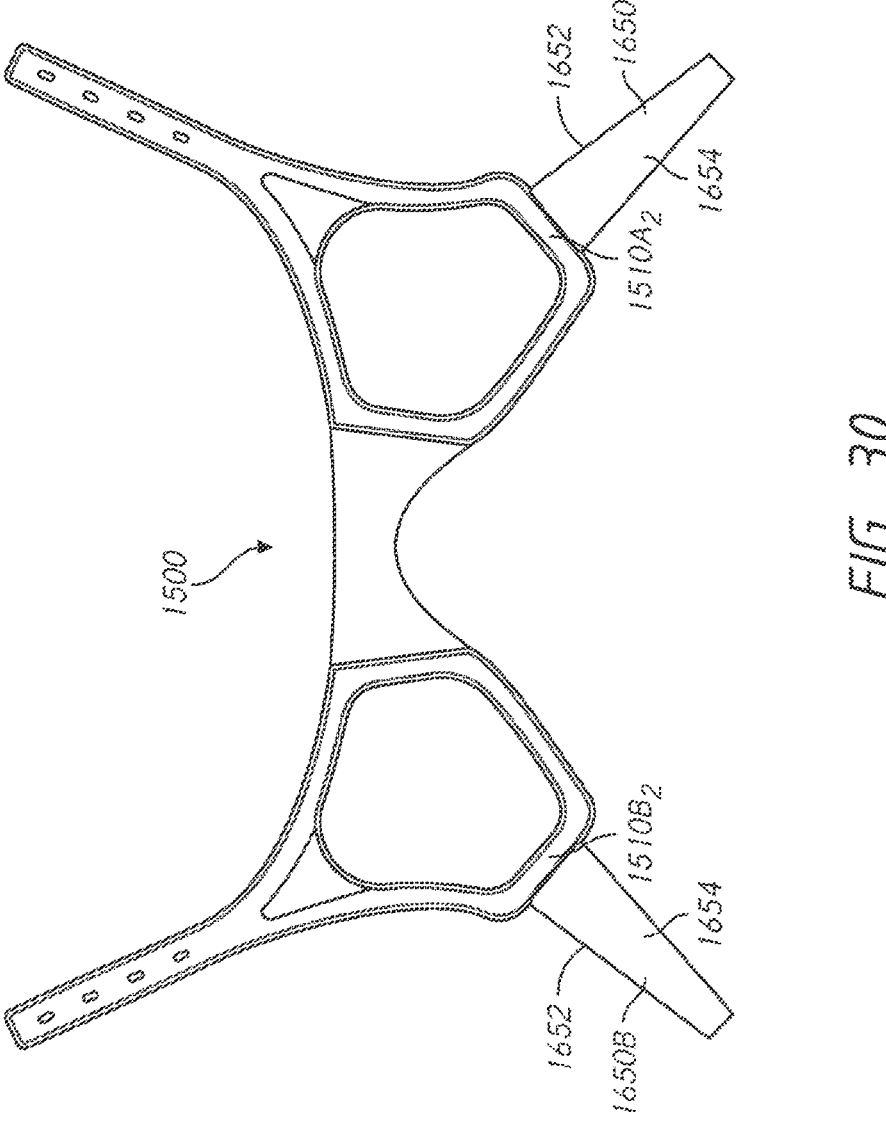
FIG. 30 shows a top view of a headgear assembly according to yet another alternative embodiment of the present disclosure in a flattened condition.

In other configurations, the headgear assembly 1500 may include a single side strap 1650A, 1650B attached to ear loops 1510A, 1510B, as shown in FIG. 30. The single side strap 1650A, 1650B has a substantially rigid structure to maintain stability of the patient interface between the user's chin and nose. The bottom edge 1654 of the single side strap 1650A, 1650B may extend horizontally from the segments 1510A$_2$, 1510B$_2$. The top edge 1652 of the single side strap 1650A, 1650B may be angled relative to the bottom edge 1654 in the lengthwise direction such that the side straps 1650A, 1650B are tapered in a direction from the ear loops 1510A, 1510B towards the free end of the side straps 1650A, 1650B. The tapered shape of the side straps 1650A, 1650B allows the free ends to be positioned at multiple positions along a width of the respective side straps 1650A, 1650B. For example, the free ends could be positioned at the middle of the side straps 1650A, 1650B, toward the top edge 1652 or toward the bottom edge 1654. The changes in positioning changes an angle of the fold in the side straps 1650A, 1650B, which, in turn, changes the angle of the headgear connectors and, thus, the angle of the patient interface.

Figure 31B:
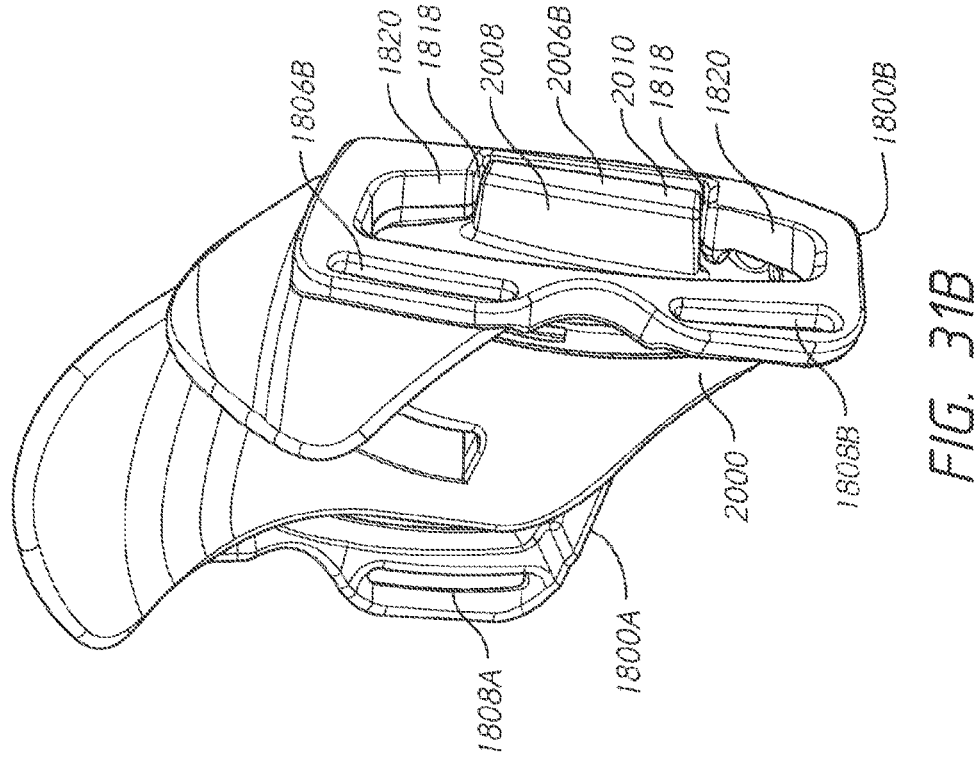
FIG. 31B shows a rear perspective view of the connection element arrangement of FIG. 31A.
Figure 31A:
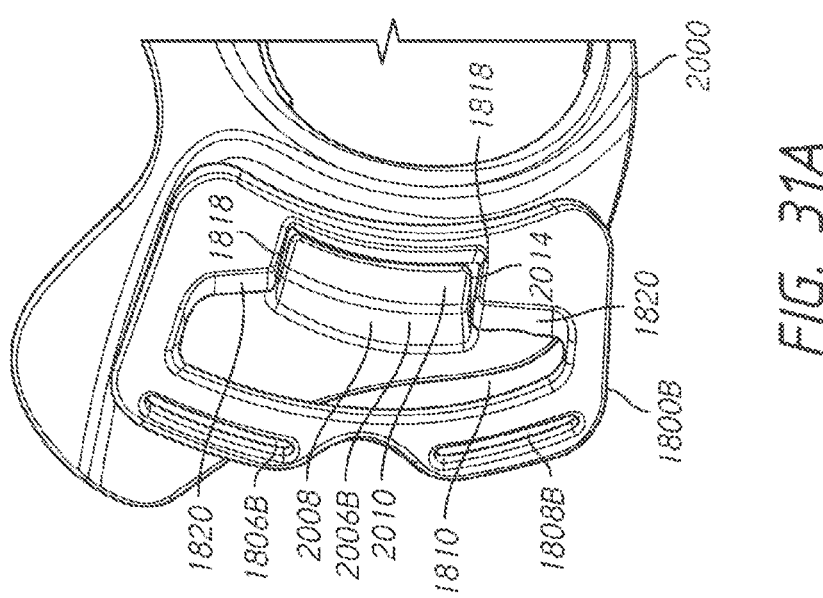
FIG. 31A shows a front perspective view of an alternative non-limiting connection element arrangement.
Figures 32A, 32B, 32C:
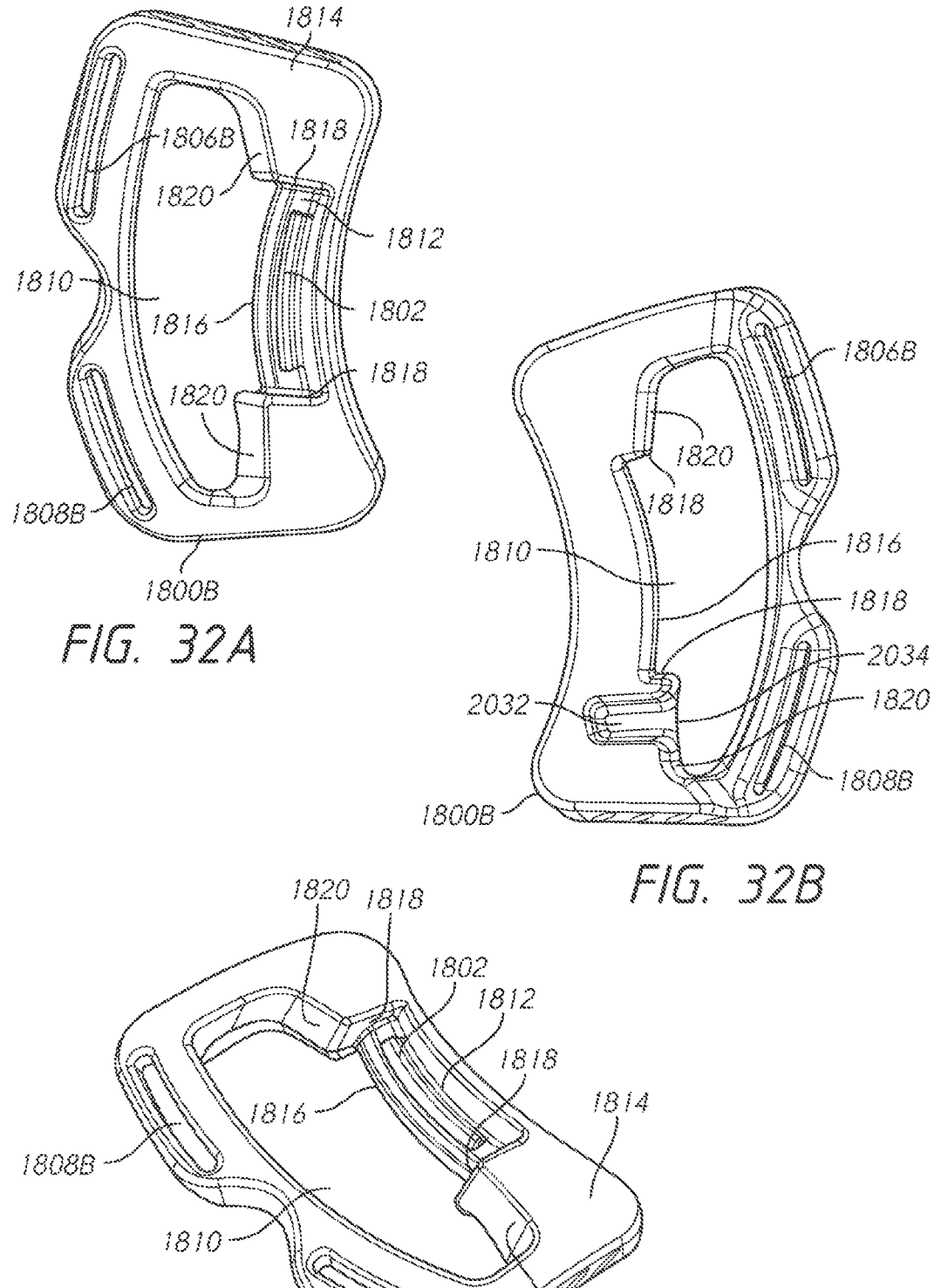
FIG. 32A shows a front plan view of a connection element of the connection element arrangement.
FIG. 32B shows a rear plan view of the connection element of FIG. 31A.
FIG. 32C shows a top perspective view of the connection element of FIG. 31A.

FIGS. 31A to 35D illustrate an alternative non-limiting connection element arrangement 1700 similar to the connection arrangement illustrated in FIGS. 8A to 10F between the frame 1000 and the headgear connection elements 800A, 800B. Similar to the headgear connection elements 800A, 800B, the headgear connection elements 1800A, 1800B are attached to the mask frame 2000 such that the headgear connection elements 1800A, 1800B are angled toward each other (i.e., projected planes of each of the headgear connection elements 1800A, 1800B converge) such that force vectors are transmitted to the headgear (not shown) at an angle to ensure proper sealing and comfort between the cushion module and the user. Further, the headgear connection elements 1800A, 1800B may have a curved concave inner surface that corresponds to the shape of the outer surface of the mask frame 2000 upon which the headgear connection elements 1800A, 1800B are mounted. Similarly, the headgear connection elements 1800A, 1800B may have a curved convex outer surface that follows the aesthetic contours of the mask frame 2000. FIGS. 31A and 31B illustrate a right headgear connection element 1800B attached to a right fixation post 2006B of a mask frame 2000. In the illustrated configuration, the right headgear connection element 1800B is only depicted. However, the left headgear connection element 1800A is a mirror image of the right headgear connection element 1800B, and so the following disclosure will be focused on the right headgear connection element 1800B. As illustrated, the right headgear connection element 1800B has a shape that is taller than wider to provide convenient gripping surfaces such that the user may more easily grip the top and bottom edges of the right headgear connection element 1800B when connecting the right headgear connection element 1800B to the right fixation post 2006B. As shown in FIGS. 32A to 32C, the right headgear connection element 1800B has slots 1806B, 1808B through which ends of the right upper and lower straps (not shown) can extend and be looped upon themselves. Similarly, as shown in FIG. 31B, the left headgear connection element 1800A has slots 1806A, 1808A (view of slot 1806A obstructed in FIG. 31B), through which ends of the right upper and lower straps (not shown) can extend and be looped upon themselves.

Figure 33A:
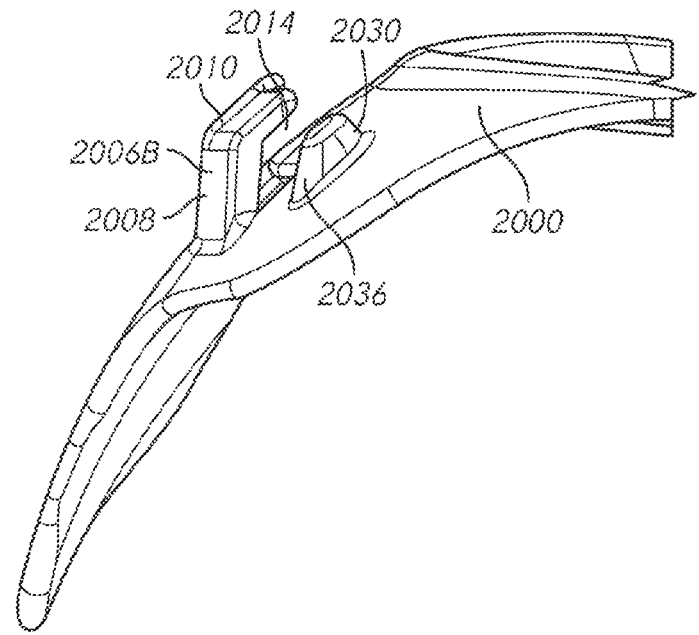
FIG. 33A shows a bottom perspective view of a mask frame and a fixation post of the connection element arrangement of FIG. 31A.
Figure 33B:
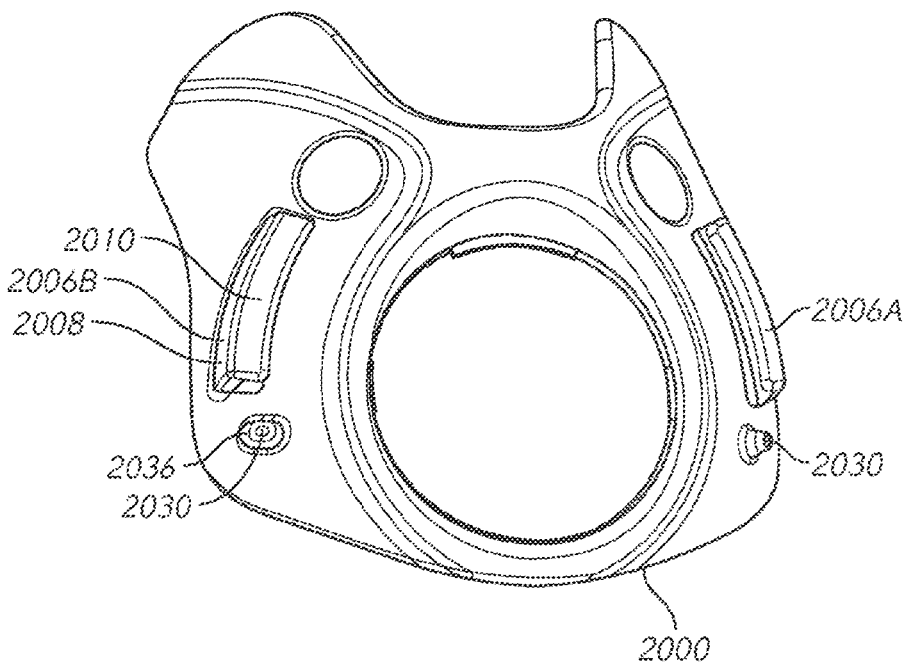
FIG. 33B shows a front perspective view of the mask frame of FIG. 31A.

Similar to the right headgear connection element 800B illustrated in FIGS. 8A to 10F, the right headgear connection element 1800B is removably connected to the right fixation post 2006B such that a headgear (not shown) and an interface (not shown) may be secured to a user. More specifically, the right fixation post 2006B is inserted into an opening 1810 within a middle section of the right headgear connection element 1800B and the right fixation post 2006B engages the right headgear connection element 1800B to connect the mark frame 2000 to the right headgear connection element 1800B. The right fixation post 2006B protrudes substantially outward from a surface of the mask frame 2000, as shown in FIGS. 33A and 33B. However, in contrast to the right fixation ridge 1006B in FIGS. 8A to 10F, the right fixation post 2006B has a latching portion 2010 connected to an extending portion 2008. The extending portion 2008 positions the latching portion 2010 a distance from the surface of the frame mask 2000 to create a gap 2014 (shown in FIGS. 33A and 34). In operation, the right headgear connection element 1800B is positioned within the gap 2014 to connect the right headgear connection element 1800B and the right fixation post 2006B.

Figure 34:
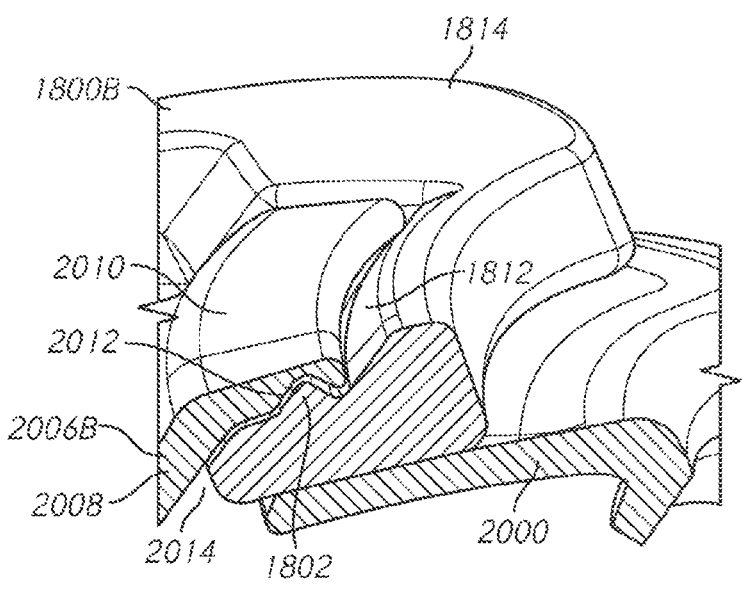
FIG. 34 shows a cross-sectional view of the connection element attached to the mask frame of FIG. 31A.
Figure 35A:
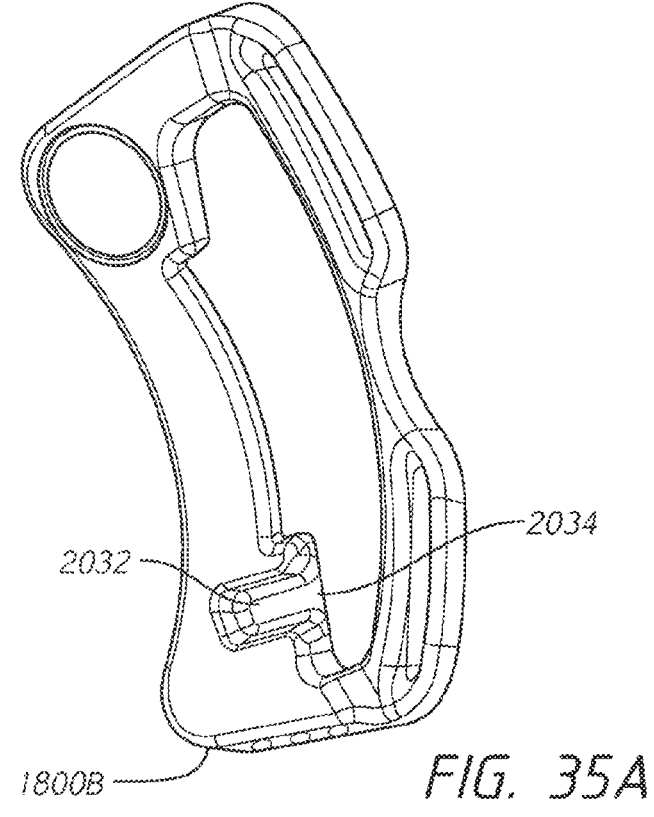
FIG. 35A shows a rear plan view of the connection element of FIG. 31A to illustrate a locator recess on the connection element.

As illustrated in FIG. 34, the connection between the right headgear connection element 1800B and the right fixation post 2006B may be retained by an interference fit between a male connector portion 1802 positioned on the right headgear connection element 1800B and a female connector portion 2012 positioned within the latching portion 2010 of the right fixation post 2006B. The male connection portion 1802 may include an interference bump that protrudes outward (i.e., a direction facing away from the user) from a surface of the right headgear connection element 1800B. The male connection portion 1802 is not limited to a single elongate protrusion of any particular shape. However, the female connector portion 2012 has a corresponding shape and size as the male connection portion 1802. The female connector portion 2012 is recessed inward from a surface of the latching portion 2010 of the right fixation post 2006B that faces the right headgear connection element 1800B. The male connection portion 1802 and the female connector portion 2012 may have a friction or interference fit to maintain the connection between the right headgear connection element 1800B and the right fixation post 2006B. Further, the right headgear connection element 1800B may be sandwiched or wedged between the mask frame 2000 and the right fixation post 2006B to prevent movement of the right headgear connection element 1800B relative to the mask frame 2000. The right fixation post 2006B may be slightly flexible such that the male connection portion 1802 and the female connector portion 2012 may be disengaged and the right headgear connection element 1800B may be separated from the right fixation post 2006B. In other words, when the right headgear connection element 1800B is pulled away from the right fixation post 2006B, at least one of the outwardly extending portion 2008 or the latching portion 2010 may deflect such that the male connection portion 1802 may be disconnected from the female connector portion 2012 and the right headgear connection element 1800B may be disconnected from the mask frame 2000.

In the illustrated embodiment, the male connection portion 1802 may be positioned on a tapered recessed portion 1812 of the right headgear connection element 1800B. The tapered recessed portion 1812 is recessed inward from an outer surface 1814 of the right headgear connection element 1800B and tapers in a direction from the outer surface 1814 toward the opening 1810 such that an edge 1816 of the tapered recessed portion 1812 defines a side of the opening 1810. As shown in FIG. 34, the tapered recessed portion 1812 reduces the thickness of the right headgear connection element 1800B such that the thickness of the right headgear connection element 1800B at the edge 1816 is less than a height of the gap 2014 between the surface of the mask frame 2000 and the latching portion 2010. Accordingly, the right headgear connection element 1800B may be easily inserted into the gap 2014 of the right fixation post 2006B until the male connection portion 1802 and the female connection portion 2012 are engaged. Further, the tapered recessed portion 1812 may have a corresponding size and shape as the gap 2014 such that the tapered recessed portion 1812 fits snugly within the gap 2014. As illustrated in FIGS. 31A and 31B, the tapered recessed portion 1812 includes sidewall or shoulder portions 1818 that are positioned immediately adjacent to the right fixation post 2006B. Accordingly, the sidewall or shoulder portions 1818 which prevent the headgear connection element 1800B from rotating when engaged with the right fixation post 2006B. In other words, the sidewall or shoulder portions 1818 contact the outer walls of the right fixation post 2006B to block and obstruct axial rotation of the headgear connection element 1800B around the right fixation post 2006B.

Figure 10A:
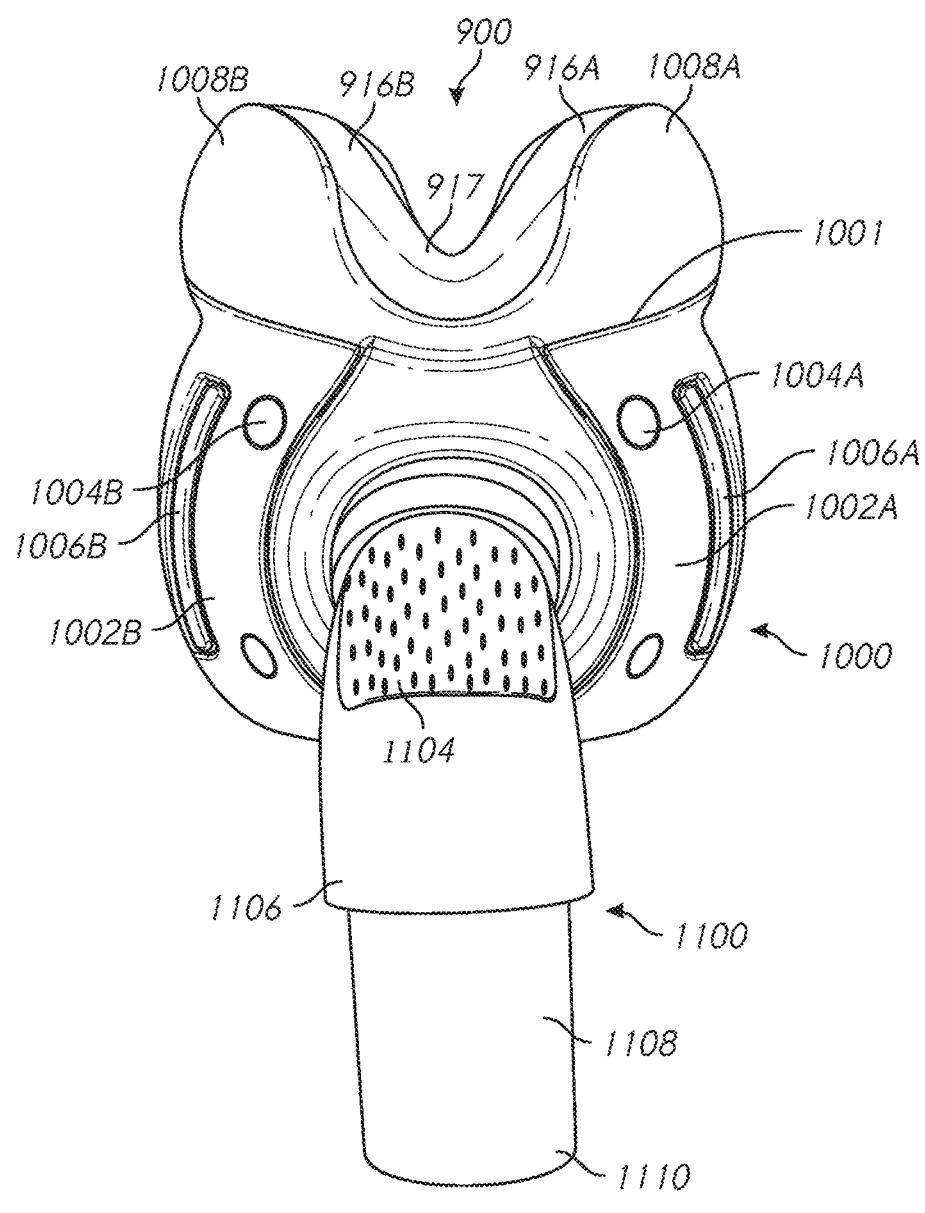
FIG. 10A shows an elevated front plan view of a frame assembly.
Figures 10B, 10C:
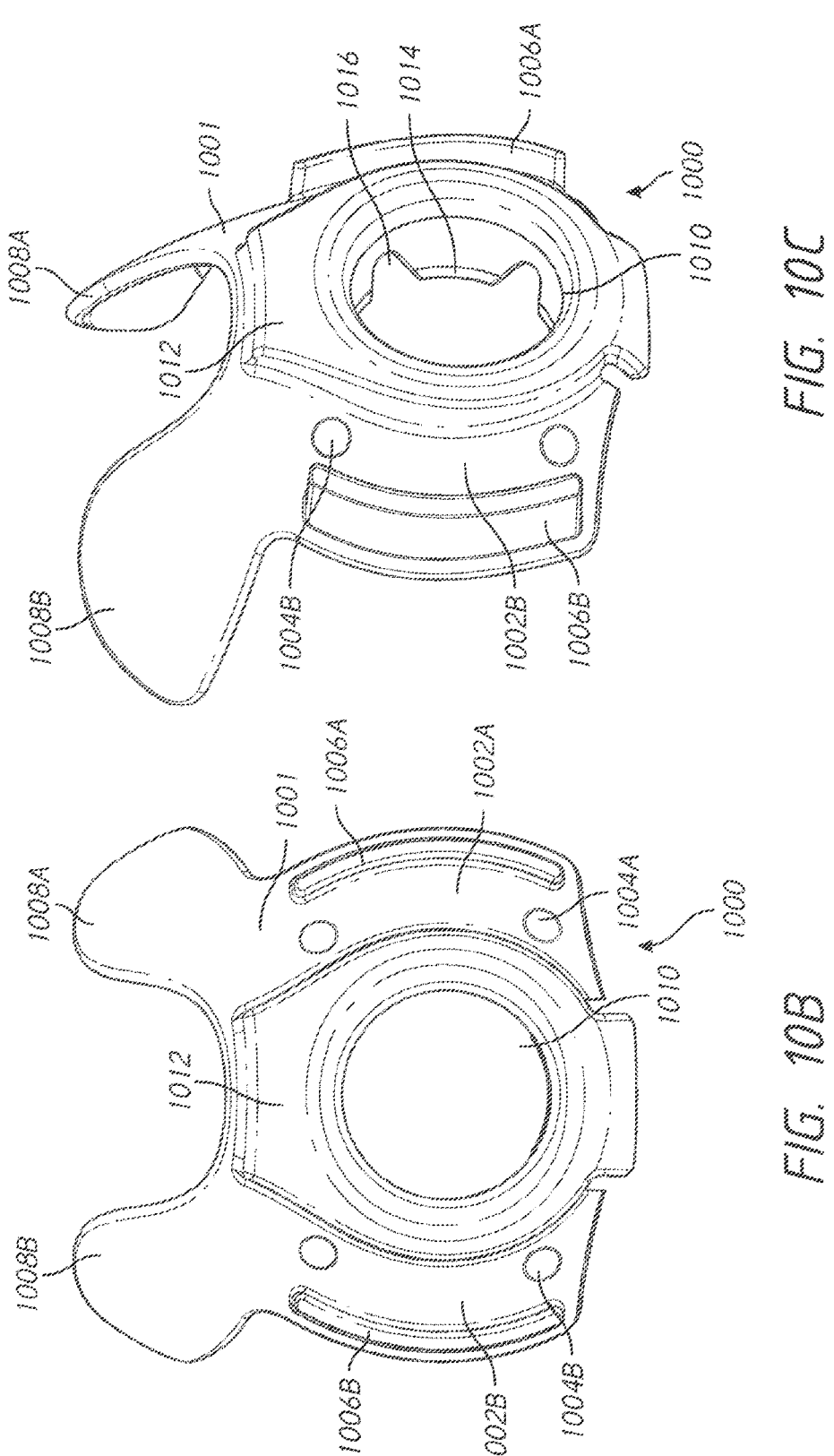
FIG. 10B shows a front plan view of a frame of a patient interface.
FIG. 10C shows a perspective view of the frame of FIG. 10B.
Figure 10D:
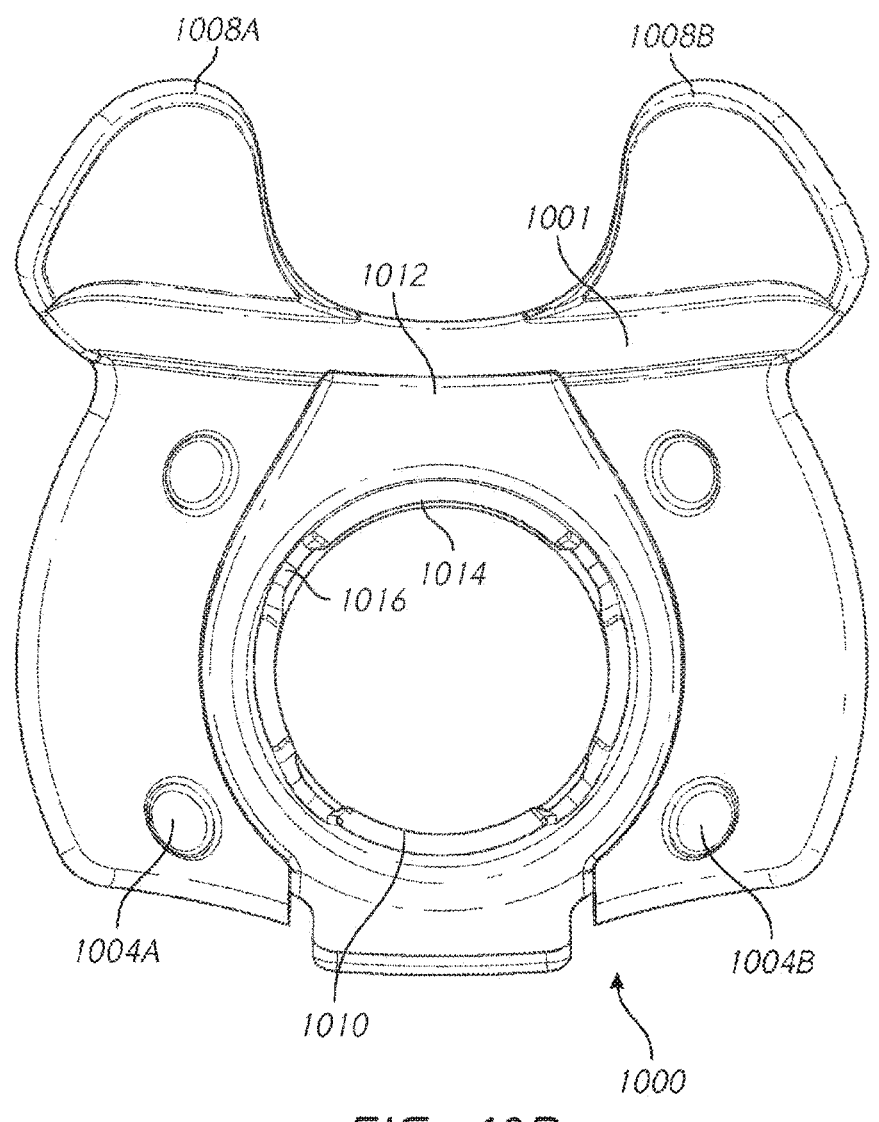
FIG. 10D shows a rear plan view of the frame of FIG. 10B.
Figure 10F:
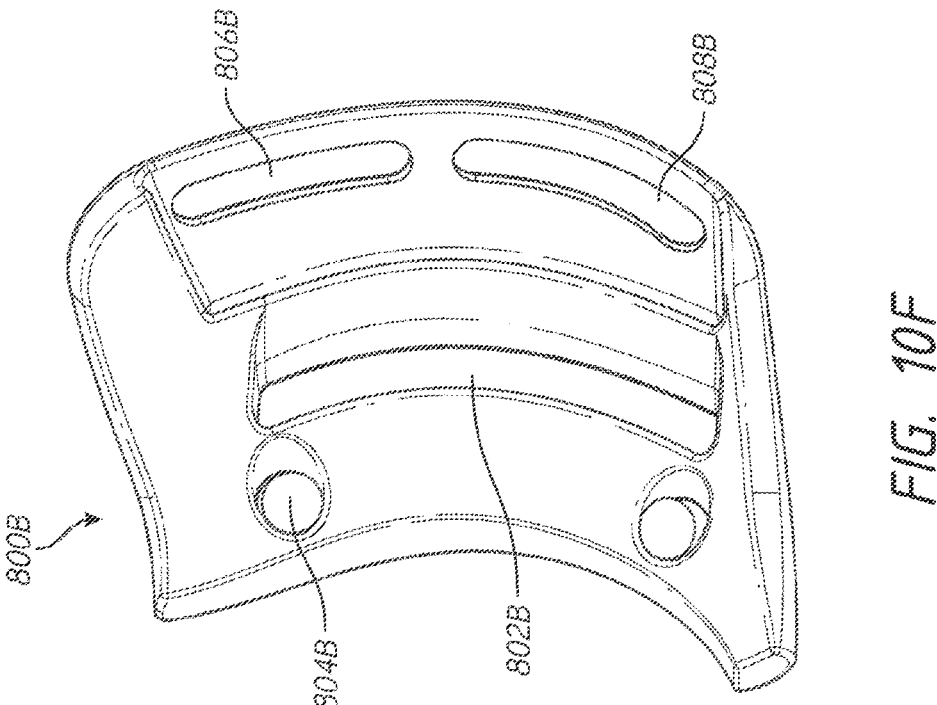
FIG. 10F shows a rear plan view of the connection element of FIG. 10E.
Figure 10E:
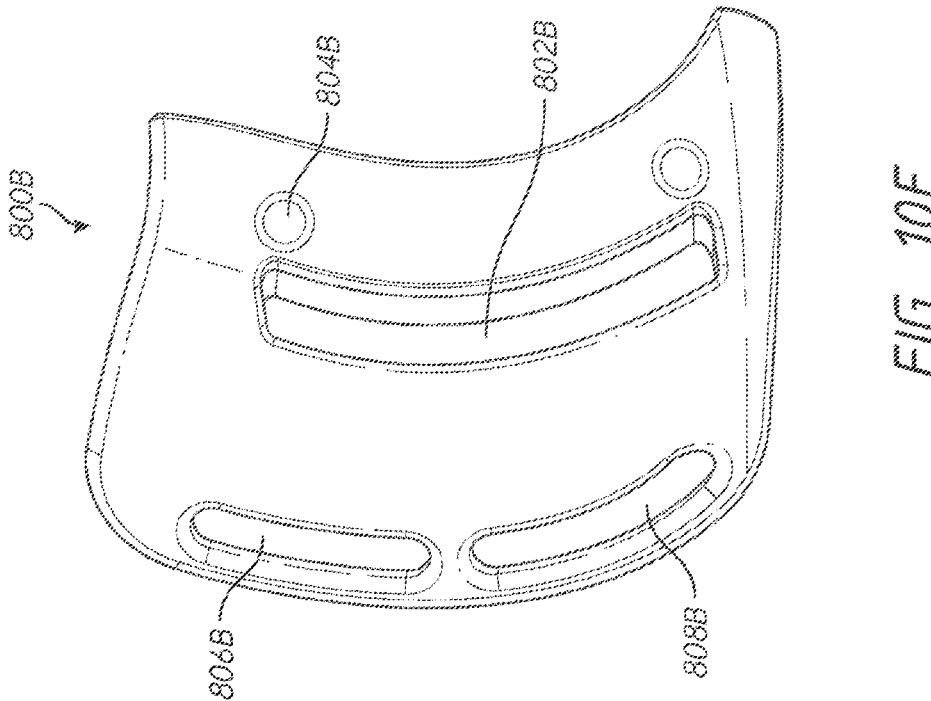
FIG. 10E shows a front plan view of a connection element for use with a frame of a patient interface.

The opening 1810 of the right headgear connection element 1800B is substantially larger than the opening or aperture of the fixation region interfacing section 802B of the right headgear connection element 800B in FIGS. 10E-F. The opening 1810 provides a larger area through which the user may easily insert the right fixation post 2006B through the right headgear connection element 1800B. In addition, the opening 1810 allows the right headgear connection element 1800B to be smaller and lighter by requiring less material to be used to from the right headgear connection element 1800B (i.e., compared to the right headgear connection element 800B, for example), which may improve user comfort. Further, a side of the opening 1810 connected to the tapered recessed portion 1812 may be shaped to facilitate engagement of the right headgear connection element 1800B and the right fixation post 2006B. As illustrated, the opening 1810 may have guide portions 1820 that are adjacent to the tapered recessed portion 1812. The guide portions 1820 may be slightly tapered or angled toward the tapered recessed portion 1812. Accordingly, when the right fixation post 2006B is inserted into the opening 1810, the guide portions 1820 may contact and guide the right fixation post 2006B toward the tapered recessed portion 1812 such that the right headgear connection element 1800B and the right fixation post 2006B may be more easily aligned and engaged.

As illustrated in FIGS. 35A-D, the mask frame 2000 may include a locator guide 2030 to assist in properly aligning the right headgear connection element 1800B with the right fixation post 2006B. The locator guide 2030 also prevents the user from inadvertently fitting the right headgear connection element 1800B to the left fixation post 2006A and vice versa. The locator guide 2030 may be a protrusion that extends outward from the surface of the mask frame 2000. Accordingly, the right headgear connection element 1800B has a locator recess 2032 having a corresponding size and shape to receive the locator guide 2030 when the right headgear connection element 1800B is properly fitted and aligned with the right fixation post 2006B. The locator guide 2030 has a tapered leading surface 2036 such that the locator guide 2030 may be easily aligned with and inserted into the locator recess 2032. Similarly, the locator guide 2030 is depicted as having an ovular cross-sectional shape. The ovular cross-sectional shape provides the locator guide 2030 with rounded edges and surfaces such that the locator guide 2030 may be easily aligned with and inserted into the locator recess 2032. Even further, the locator recess 2032 may have a tapered opening 2034 to provide a wider initial opening to further facilitate alignment with the locator guide 2030.

Figure 36A:
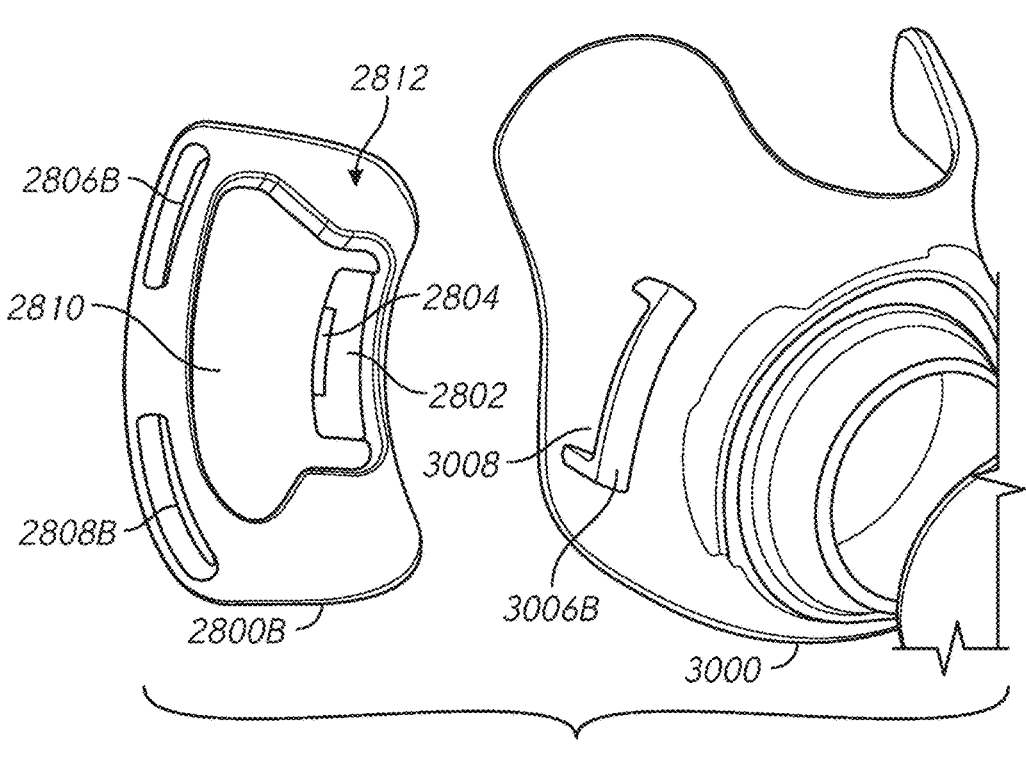
FIG. 36A shows a front perspective view of another alternative non-limiting connection element arrangement illustrating a connection element separate from a mask frame.
Figure 36B:
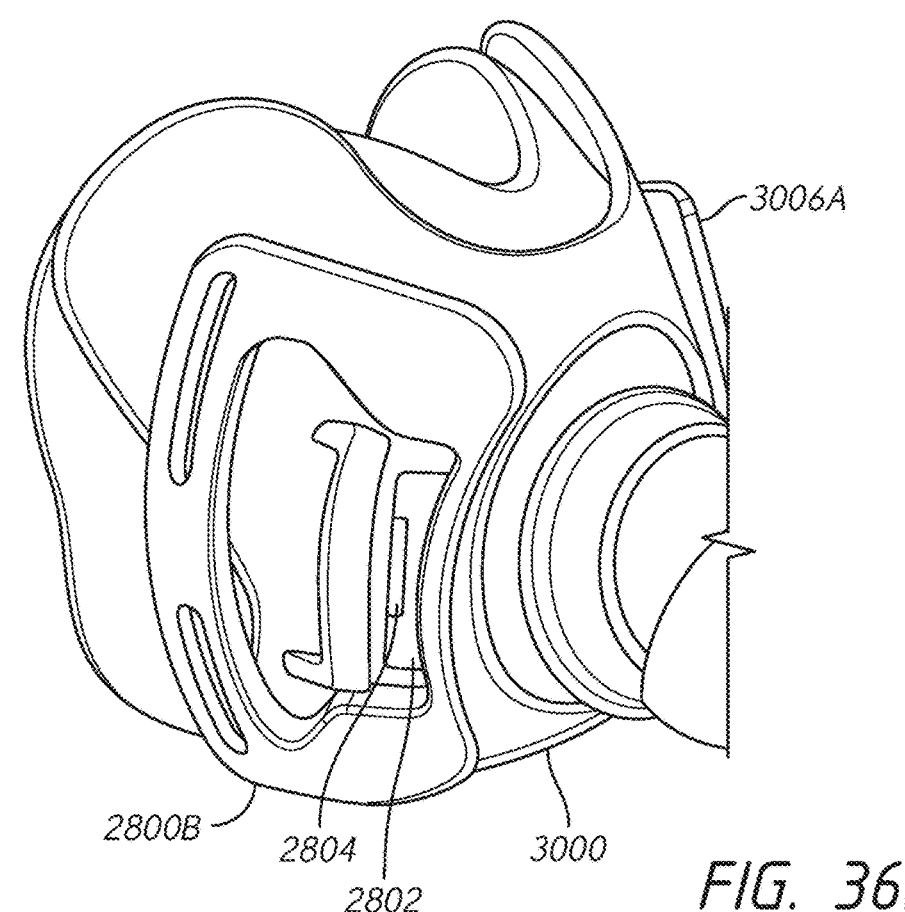
FIG. 36B shows a front perspective view of the connection element aligned with but not inserted into a fixation post of the mask frame of FIG. 36A.
Figure 36C:
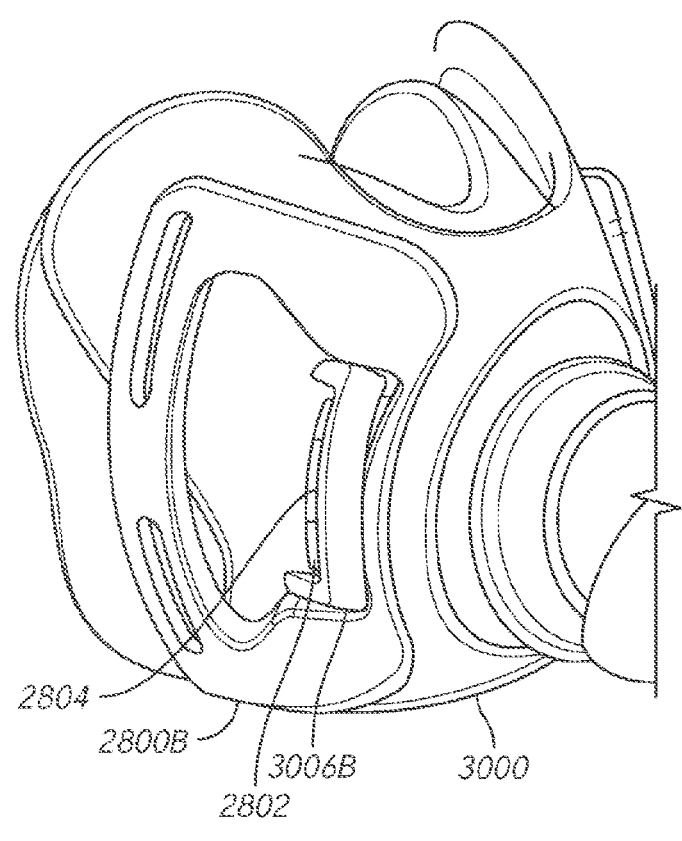
FIG. 36C shows a front perspective view of the connection element inserted into the mask frame of FIG. 36A.
Figure 37A:
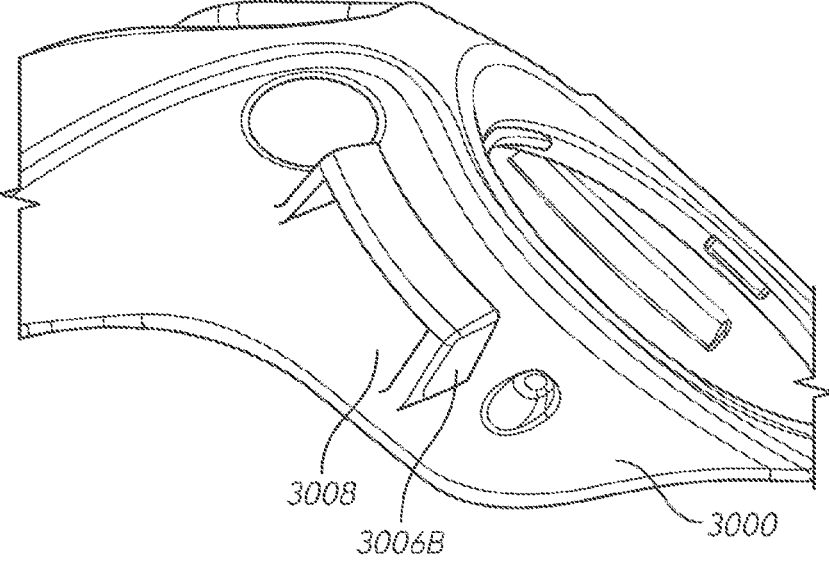
FIG. 37A shows a side perspective view of the mask frame and a fixation post of FIG. 36A.
Figure 37B:
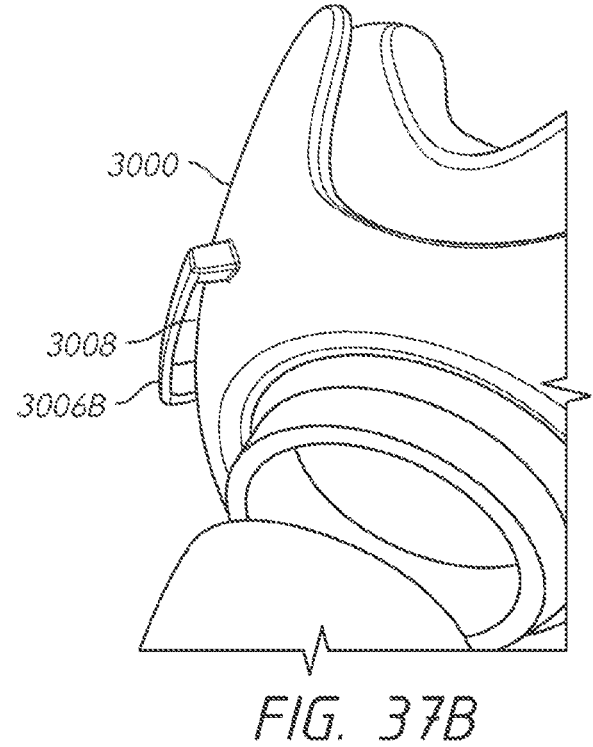
FIG. 37B shows a front perspective view of the mask frame and the fixation post of FIG. 36A.

Another alternative non-limiting connection element arrangement 2700 is disclosed in FIGS. 36A to 41B. FIGS. 36A-C illustrates a right headgear connection element 2800B releasably connected to a right fixation post 3006B of a mask frame 3000. The right headgear connection element 2800B has slots 2806B, 2808B through which ends of the right upper and lower straps (not shown) can extend and be looped upon themselves. Similar to the right headgear connection element 1800B (FIGS. 31A to 35D), the right headgear connection element 2800B is removably connected to the right fixation post 3006B such that a headgear (not shown) and an interface (not shown) may be secured to a user. More specifically, the right headgear connection element 1800B is attached to the right fixation post 3006B by inserting a portion of the right headgear connection element 2800B into the right fixation post 3006B. The right fixation post 3006B protrudes substantially outward from a surface of the mask frame 3000, as shown in FIGS. 37A and 37B. However, in contrast to the right fixation post 2006B of the connection element arrangement 1700 (FIGS. 33A and 33B), the right fixation post 3006B has a through-hole 3008 that extends through the center of the right fixation post 3006B. The right fixation post 3006B and the through-hole 3008 are depicted as having a substantially rectangular cross-sectional shape but it should be understood that the right fixation post 3006B and the through-hole 3008 are not limited to rectangular cross-sectional shapes. Further, the right fixation post 3006B and the through-hole 3008 may also have dissimilar shapes.

Figure 38:
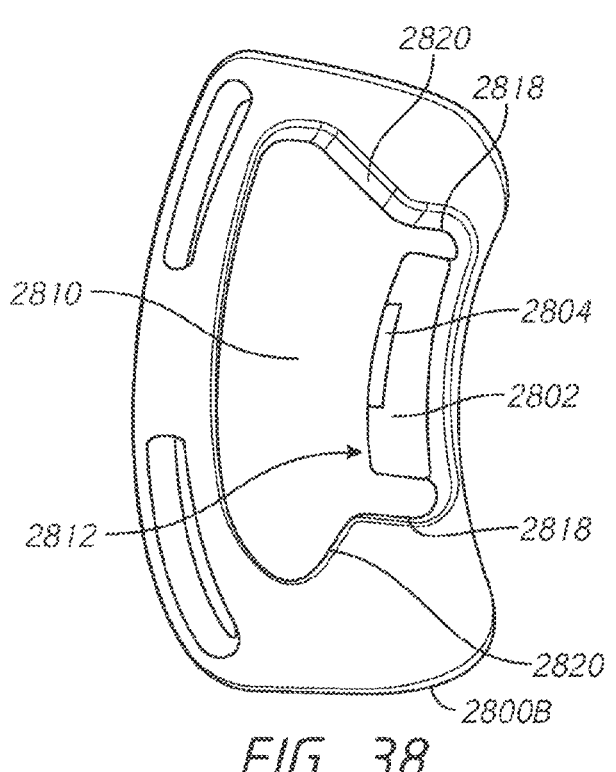
FIG. 38 shows a side view of the connection element of FIG. 36A.
Figure 39:
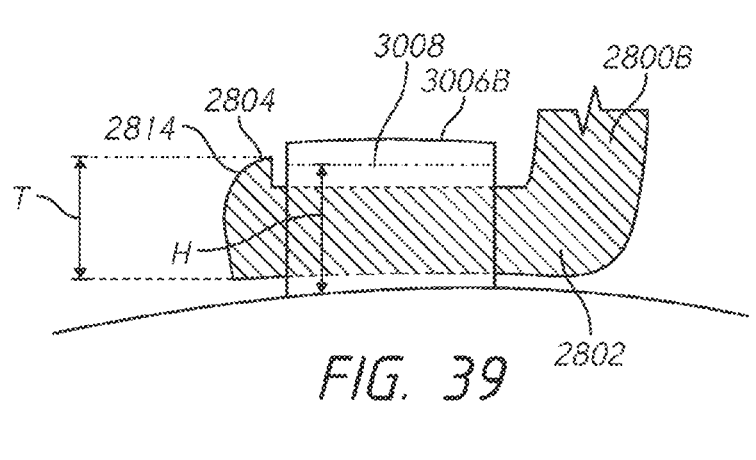
FIG. 39 shows a close-up view of an insertion portion of the connection element of FIG. 36A.

As shown in FIG. 38, the right headgear connection element 2800B has an insertion portion 2802 that extends toward and projects into the opening 2810 of the right headgear connection element 2800B. Put another way, the insertion portion 2802 may be located in a post receiving portion 2812 of the opening 2810. A raised portion 2804 is positioned on the end of the insertion portion 2802 that projects into the opening 2810. The raised portion 2804 protrudes outwardly from a surface of the insertion portion 2802. The raised portion 2804 is depicted as projecting in a direction away from the user but may also project in any outward direction from the insertion portion 2802. The raised portion 2804 protrudes a distance from a surface of the insertion portion 2802 such that the end of the insertion portion 2802 extends beyond the through-hole 3008 when the insertion portion 2802 is fully inserted into the through-hole 3008, as shown in FIG. 39. However, the insertion portion 2802 and the raised portion 2804 have a combined thickness T that is less than a through-hole height H, which allows the insertion portion 2802 and the raised portion 2804 to be inserted into the through-hole 3008.

In operation, the insertion portion 2802 is inserted entirely through the through-hole 3008 such that the raised portion 2804 is located outside of the through-hole 3008, as shown in FIG. 39. The insertion portion 2802 may bend slightly to allow the insertion portion 2802 and the raised portion 2804 to travel through the through-hole 3008. Accordingly, when the insertion portion 2802 is fully inserted into the through-hole 3008 and the insertion portion 2802 is not bent, the raised portion 2804 extends beyond the through-hole 3008 to block and obstruct the insertion portion 2802 from being removed from the through-hole 3008. In other words, the raised portion 2804 contacts a portion of the right fixation post 3006B to prevent the right headgear connection element 2800B from separating from the right fixation post 3006B.

The insertion portion 2802 has a generally elongated shape with a length that is longer than the length of the through-hole 3006 such that both ends of the insertion portion 2802 are outside of the through-hole 3008 when the insertion portion 2802 is fully inserted into the through-hole 3008. Preferably, the insertion portion 2802 has a length such that the right fixation post 3006B is retained between the raised portion 2804 and a wall of the opening 2810 to reduce an amount of free-play between the right headgear connection element 2800B and the right fixation post 3006B. The insertion portion 2802 may also have a rounded leading edge 2814 to ease entry into the through-hole 3008 by facilitating bending of the insertion portion 2802 when the insertion portion 2802 is initially inserted into the through-hole 3008. The insertion portion 2802 is depicted as having a cross-sectional shape that corresponds with the cross-sectional shape of the through-hole 3008. However, in some arrangements, the insertion portion 2802 and through-hole 3008 may have different cross-sectional shapes.

The insertion portion 2802 may be formed from a semi-rigid material that allows the insertion portion 2802 to bend slightly in order to allow the insertion portion 2802 and the raised portion 2804 to be inserted into the through-hole 3008. Accordingly, to remove the insertion portion 2802 from the through-hole 3008, the user may depress the insertion portion 2802 such that the insertion portion 2802 bends and the raised portion 2804 has a height that is less than the height H of the through-hole 3008 such that insertion portion 2802 and the raised portion 2804 may fit within and exit the through-hole 3008.

Figure 40A:
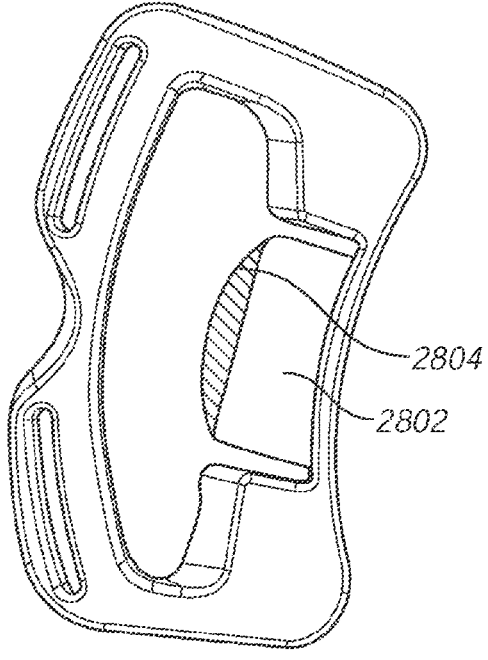
FIG. 40A shows a side view of an alternative embodiment of a connection element having a rounded insertion portion and a raised portion spanning an entire width of the insertion portion.
Figure 40B:
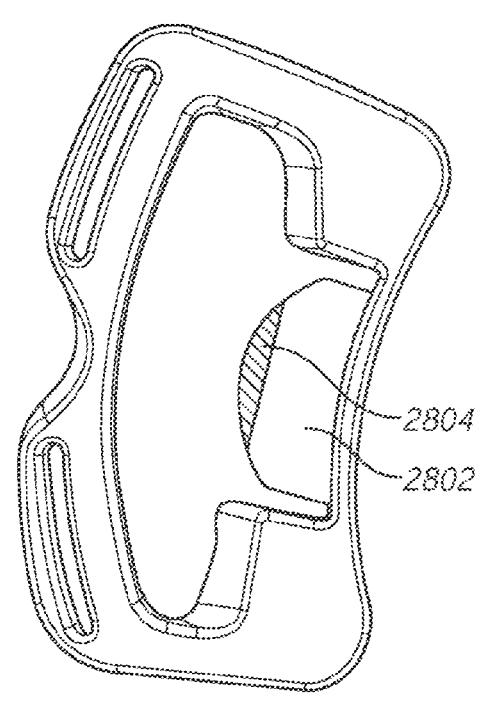
FIG. 40B shows a side view of another alternative embodiment of a connection element having a rounded insertion portion and a raised portion partially spanning a width of the insertion portion.
Figure 40C:
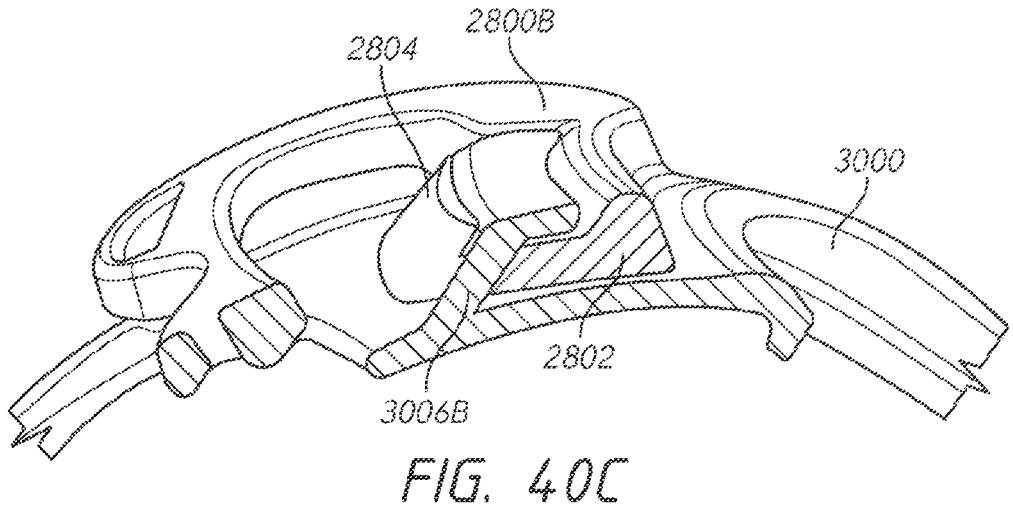
FIG. 40C shows a bottom cross-sectional view of the connection element of FIG. 40A.
Figure 40D:
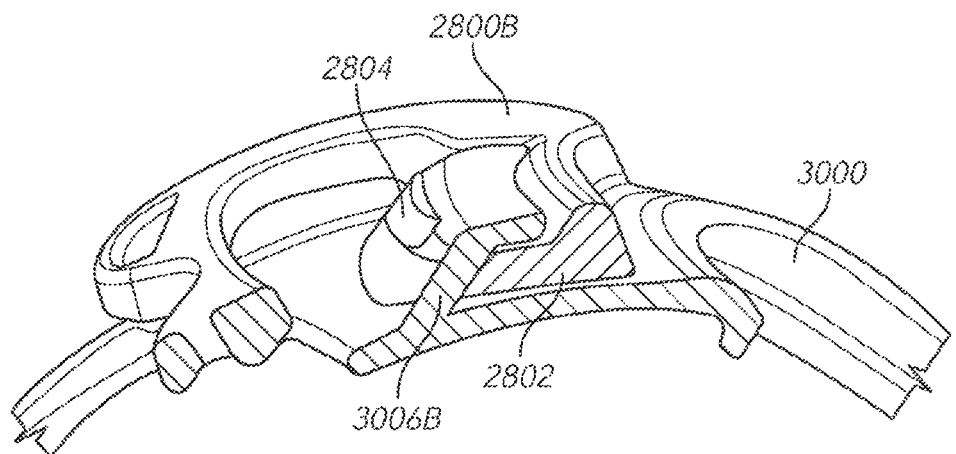
FIG. 40D shows a bottom cross-sectional view of the connection element of FIG. 40B.

The raised portion 2804 is illustrated as a single elongate protrusion that spans a portion of the insertion portion 2802. However, the raised portion 2804 is not limited to any shape or size. As illustrated in FIGS. 40A and 40C, the raised portion 2804 may span an entire width of the insertion portion 2802. Further, to facilitate insertion into the through-hole 3008, the insertion portion 2802 may have a rounded semi-circular shape (as shown in FIGS. 40A to 40D) such that the insertion portion 2802 may be easily aligned with and inserted into the through-hole 3008.

Figure 41B:
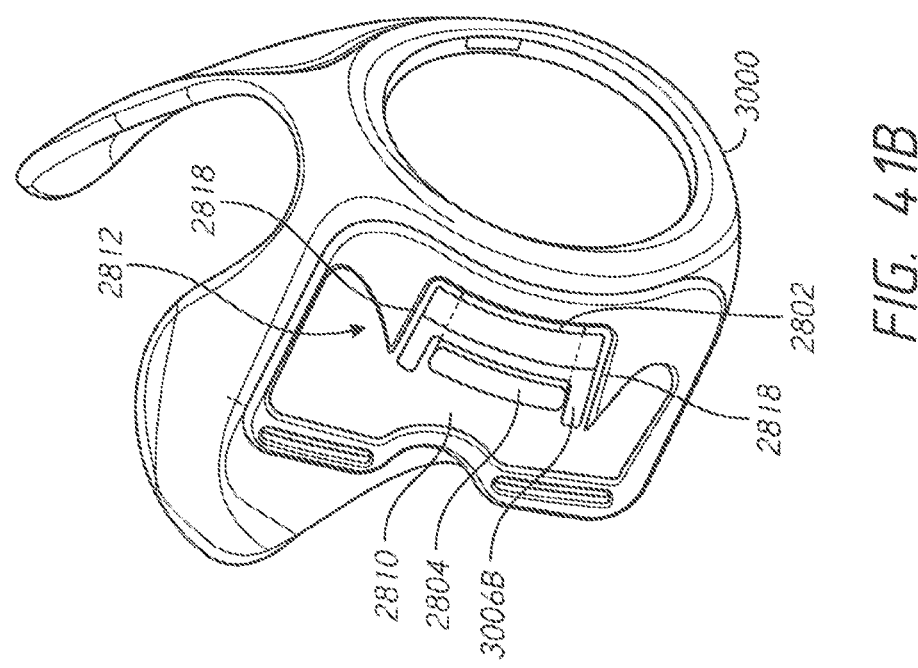
FIG. 41B shows a side perspective view of an alternative embodiment of a connection element having alternative sidewall or shoulder portions.
Figure 41A:
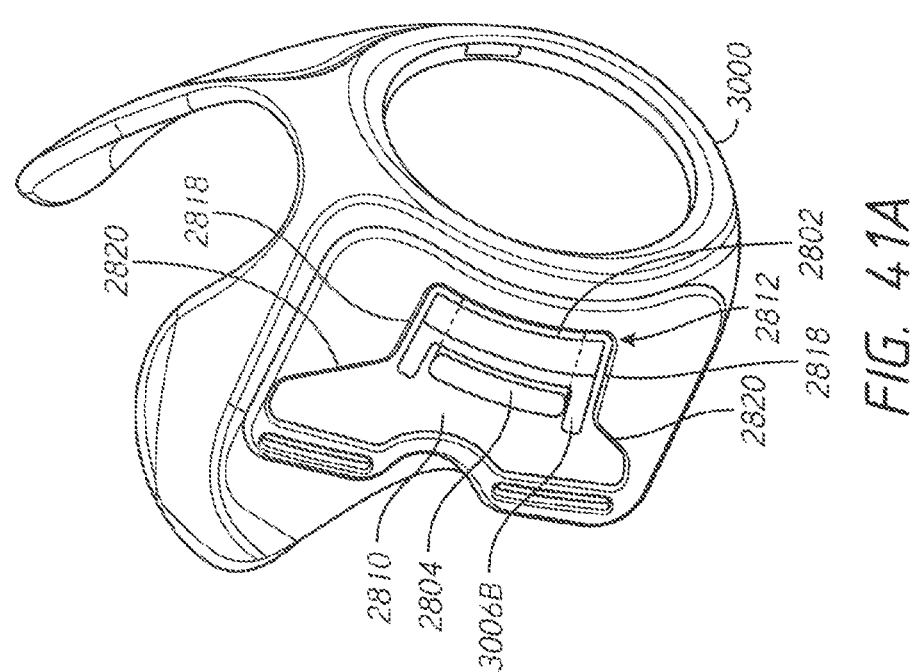
FIG. 41A shows a side perspective view of the connection element of FIG. 36A attached to the fixation post to illustrate sidewall or shoulder portions of the connection element.

As illustrated in FIG. 41A, the opening 2810 may have guide portions 2820 that are adjacent to the post receiving portion 2812 of the opening 2810. The guide portions 2820 are slightly tapered or angled toward the post receiving portion 2812. Accordingly, when the right fixation post 3006B is inserted into the opening 2810, the guide portions 2820 may contact and guide the right fixation post 3006B toward the post receiving portion 2812 such that the right headgear connection element 2800B and the right fixation post 3006B may be more easily aligned and engaged. Further, the post receiving portion 2812 of the opening 2810 includes sidewall or shoulder portions 2818 that are positioned immediately adjacent to the right fixation post 3006B when the right headgear connection element 2800B is connected to the right fixation post 3006B. Accordingly, the sidewall or shoulder portions 2818 prevent the headgear connection element 2800B from rotating when engaged with the right fixation post 3006B. In other words, the sidewall or shoulder portions 2818 contact the outer walls of the right fixation post 3006B to block and obstruct rotation of the headgear connection element 2800B axially around the right fixation post 3006B. FIG. 41B illustrates an alternative arrangement having a larger opening 2810 and sidewall or shoulder portions 2818 but without the guide portions 2820 in FIG. 41A.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Reference to any prior art in this specification is not, and should not be taken as, an acknowledgment or any form of suggestion that that prior art forms part of the common general knowledge in the field of endeavour in any country in the world.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A headgear connection element for a patient interface for use with respiratory therapy, the headgear connection element comprising:
    a first end adapted to interface with a headgear;
    a second end adapted to interface with a frame of the patient interface; and
    a body extending between the first end and the second end substantially along a first axis;
    wherein the second end comprises a body portion connected to the body and a projection comprising a first portion extending from the body portion of the second end along a second axis substantially transverse to the first axis and a second portion laterally offset from the body portion of the second end, the second portion extending from the first portion in a direction substantially parallel to the first axis, the second portion is wider than the first portion, and the projection adapted to protrude through the frame of the patient interface such that the body portion is located on a first side surface of the frame and the second portion of the projection is located on a second side surface of the frame opposite the first side surface.

2. The headgear connection element of claim 1, wherein the body is substantially rigid.

3. The headgear connection element of claim 2, wherein the first end comprises a headgear retainer defined by a slot.

4. The headgear connection element of claim 2, wherein the body is substantially arcuate.

5. The headgear connection element of claim 2, wherein the body has a curved shape that is configured to extend substantially horizontally from the second end and then substantially upwardly and horizontally along a user's face from about halfway along the body to the first end.

6. The headgear connection element of claim 2, wherein the projection is substantially rigid.

7. The headgear connection element of claim 1, wherein a first section of the second portion extends from first portion back towards a middle of the body and a second section of the second portion extends from the first portion away from the middle of the body.

8. A frame for a patient interface for use in a respiratory therapy system, the frame comprising:

a frame body, a gases aperture in the frame body, a first pair of left and right connection slots in the frame body, and a pair of headgear connection elements according to claim 1, each connected to a respective one of the first pair of left and right connection slots.

9. The frame of claim 8 further comprising a second pair of left and right connection slots in the frame body, wherein:

the first pair of left and right connection slots comprises left and right upper connection slots, and the second pair of left and right connection slots comprises left and right lower connection slots.

10. The frame of claim 9, wherein the pair of headgear connection elements curve inwardly in a direction towards the frame body.

11. The frame of claim 9, wherein the pair of headgear connection elements are symmetrical with respect to each other.

12. The frame of claim 9, wherein portions of a wall of the frame that define the first pair of left and right connection slots each includes a recess adapted to hold the second portion of each one of the pair of headgear connection elements.

13. The frame of claim 12, wherein the second portion of the projection of each one of the pair of headgear connection elements is forced through the respective one of the pair of left and right connection slots such that it rests in the recess.

14. The frame of claim 13, wherein the pair of headgear connection elements are fixed to the frame by ultrasonic welding or high-frequency welding.

15. The frame of claim 13, wherein the pair of headgear connection elements are fixed to the frame by a mechanical fastening or interlocking arrangement.

16. The frame of claim 13, wherein the pair of headgear connection elements are rigidly connected to the frame.

17. The frame of claim 9, wherein the pair of headgear connection elements are flexibly connected to the frame.

18. A patient interface for use in a respiratory therapy system, the patient interface comprising:

the frame of claim 9, and a cushion module which engages with the frame, the cushion module comprising:

a pliable cushion member configured to engage with a user's face; and a shell which is relatively more rigid than the pliable cushion member and adapted to help reinforce and maintain a shape of the pliable cushion member when the cushion module is linked to the frame, wherein the shell is integral with or in a form of a single piece with the pliable cushion member.

19. The patient interface of claim 18 further comprising a venting area, the venting area comprising vent apertures that permit a leak flow to escape the patient interface, wherein the vent apertures are covered by a media adapted to diffuse sound generated by the leak flow passing through the vent apertures and/or to diffuse the leak flow passing through the vent apertures by scattering or distributing the leak flow in a number of directions.

20. The patient interface of claim 19, wherein the venting area is provided on the frame.

21. The patient interface of claim 19 further comprising an elbow component, wherein the gases aperture is adapted to receive the elbow component, the elbow component adapted to swivel or rotate relative to the frame, and the venting area is provided on the elbow component.

22. The patient interface of claim 19, wherein an outer wall of the frame defines the gases aperture, an inner wall of the shell defines a brace aperture, and the outer wall and the inner wall are removably connectable by a snap-fit, interference fit or interlocking arrangement to mechanically interlock the frame with the cushion module.

23. The patient interface of claim 19, wherein the pliable cushion member comprises:

a nasal gases passageway, nasal recess and left and right upper cushion ridges configured such that an under-the-nose seal is attained, and an opening, left and right side portions and a bottom portion configured such that an around-the-mouth seal is attained.

24. The patient interface of claim 19, further comprising the headgear which interfaces with the frame in a four-point connection using the first pair of left and right connection slots and the second pair of connection slots to retain the patient interface on a head of the user, wherein the headgear interfaces with the first pair of left and right connection slots through the pair of headgear connection elements.

25. The patient interface of claim 24, wherein the headgear comprises:

a back panel adapted to rest at a back of the head, over an occiput and/or trapezius of the head, a crown strap portion adapted to generally extend from the back panel upwardly along the head, over a sternocleidomastoideoularis posterior, aricularis superior and/or temporalis, behind ears of the user to a top of the head, a left top strap and a right top strap adapted to generally extend along respective sides of the head, over the aricularis anterior, *auricularis* superior and/or temporal fascia, towards the back of the head over the ears of the user, a left bottom strap and a right bottom strap adapted to generally extend along the respective sides of the head, over the user's sternocleidomastoideoma, risorius and/or buccinator, towards the back of the head under the ears of the user.

26. The patient interface of claim 25, wherein:

the left top strap and the right top strap are secured to the frame using the respective first ends of the pair of headgear connection elements, and the left bottom strap and the right bottom strap are secured to the second pair of left and right connection slots using hooks, resealable adhesives or mechanical fastener arrangements.

27. The patient interface of claim 25, wherein the pair of headgear connection elements are configured to decrease vertical forces exerted by the left top strap and the right top strap upon the frame.

28. The frame of claim 8, wherein each of the first pair of left and right connection slots is located in a rearwardly-projecting wall portion of the frame, wherein at least a portion of the rearwardly-projecting wall portion of the frame is captured between the second portion of the projection and the body portion of the second end.

29. The headgear connection element of claim 1, wherein the second portion is wider than the first portion in the direction substantially parallel to the first axis.

30. The headgear connection element of claim 1, wherein the second portion is formed by a polygonal shape having a perimeter that defines an area, wherein an area of intersection between the first portion and the second portion is less than the area of the second portion.

31. The headgear connection element of claim 7, wherein the first section and the second section of the second portion define different lengths in the direction substantially parallel to the first axis.

* * * * *